(12) United States Patent
Wangh et al.

(10) Patent No.: US 10,240,178 B2
(45) Date of Patent: Mar. 26, 2019

(54) MISPRIMING PREVENTION REAGENTS

(71) Applicant: Brandeis University, Waltham, MA (US)

(72) Inventors: Lawrence J. Wangh, Auburndale, MA (US); Kenneth E. Pierce, Natick, MA (US); Jesus A. Sanchez, Framingham, MA (US); John E. Rice, Natick, MA (US); Alexandra Isabel King Over, Waltham, MA (US); Adam E. Osborne, Waltham, MA (US)

(73) Assignee: Brandeis University, Waltham, MA (US)

( * ) Notice: Subject to any disclaimer, the term of this patent is extended or adjusted under 35 U.S.C. 154(b) by 439 days.

(21) Appl. No.: 14/969,869

(22) Filed: Dec. 15, 2015

(65) Prior Publication Data

US 2016/0265014 A1   Sep. 15, 2016

Related U.S. Application Data

(60) Provisional application No. 62/136,048, filed on Mar. 20, 2015, provisional application No. 62/094,597, filed on Dec. 19, 2014.

(51) Int. Cl.
| | |
|---|---|
| *C12P 19/34* | (2006.01) |
| *C12Q 1/6848* | (2018.01) |
| *C12Q 1/686* | (2018.01) |
| *C07H 21/00* | (2006.01) |

(52) U.S. Cl.
CPC ............ *C12P 19/34* (2013.01); *C07H 21/00* (2013.01); *C12Q 1/686* (2013.01); *C12Q 1/6848* (2013.01)

(58) Field of Classification Search
CPC .............................. C12P 19/34; C12Q 1/6848
USPC ........................................................ 435/6.12
See application file for complete search history.

(56) References Cited

FOREIGN PATENT DOCUMENTS

| | | |
|---|---|---|
| WO | WO-2006/044994 A2 | 4/2006 |
| WO | WO-2006/044995 A1 | 4/2006 |
| WO | WO-2007/041201 A2 | 4/2007 |
| WO | WO-2010/105074 A1 | 9/2010 |
| WO | WO-2016/014921 A1 | 1/2016 |

OTHER PUBLICATIONS

International Search Report for Application No. PCT/US2015/065807, dated Dec. 15, 2015.
Rice, et al., "Monoplex/multiplex linear-after-the-exponential-PCR assays combined with PrimeSafe and Dilute-"n"-Go sequencing," Nat Protoc, 2(10): 2429-2438 (2007).

*Primary Examiner* — Jezia Riley
(74) *Attorney, Agent, or Firm* — Foley Hong LLP; Dana M. Gordon; Brendan T. Jones

(57) ABSTRACT

Provided herein are mispriming prevention reagents, compositions and kits comprising such reagents and methods of use thereof.

24 Claims, 66 Drawing Sheets
Specification includes a Sequence Listing.

| Experiment | Experiment | Target Gene |
|---|---|---|
| Mispriming suppression by TSDBB (Figure 4) | Symmetric PCR | Tay-Sachs Gene |
| TSDBB amplification compared to PSL (Figure 5) | Symmetric PCR | ATP6V1C1 |
| Enhanced amplification efficiency with TSDBB (Figure 6, MCHR1 target) | Symmetric PCR | MCHR1 |
| Enhanced amplification efficiency with TSDBB (Figure 6, ATP6V1C1 target) | Symmetric PCR | ATP6V1C1 |
| Enhanced amplification efficiency with TSDBB (Figure 6, ELF5 target) | Symmetric PCR | ELF5 |
| Delay of Primer-dimer amplification by TSC47D and TSDBB (Figure 7) | Symmetric PCR | N/A |
| NTC amplification (Figure 8) | Symmetric PCR | ATP6V1C1 |
| NTC amplification (Figure 9) | Symmetric PCR | ATP6V1C1 |
| NTC amplification (Figure 10) | Symmetric PCR | ATP6V1C1 |
| Valley Tms for different reagents (Figure 11) | Symmetric PCR | Tay-Sachs Gene |
| Depth of valley with increasing TSDBB concentration (Figure 12) | Symmetric PCR | ATP6V1C1 |
| Method for determining the optimal reagent concentration (Figure 13) | Symmetric PCR | N/A |
| Valley Tms for different reagents (Figure 14) | Symmetric PCR | Tay-Sachs Gene |
| Probe detection (Figure 15) | Symmetric PCR | N/A |
| Gel showing TSDBB (Figure 16) | Symmetric PCR | N/A |
| Effect of dissolving TSDBB in Water vs Tris (Figure 17) | Symmetric PCR | MCHR1 |
| Effect of premixing TSDBB with polymerase-NTC samples (Figure 18) | Symmetric PCR | Cystic Fibrosis gene |
| Effect of premixing TSDBB with polymerase-DNA samples (Figure 19) | Symmetric PCR | Cystic Fibrosis gene |
| Suppression of type 2 mispriming by TSDBB and PSL (Figure 20) | Symmetric PCR | ATP6V1C1 |

Figure 22

| Experiment | Upper primer Sequence | Lower primer Sequence |
|---|---|---|
| Mispriming suppression by TSDBB (Figure 4) | 5'CCCTTCTCTCTGCCCCCTGGT 3' | 5'AGGGGTTCCACTACGTAGA'3 |
| TSDBB amplification compared to PSL (Figure 5) | 5'-CTGTTTGAGAGTTAAATGATGTC-3' | 5'-ACACCTCAGCATATAACAA-3' |
| Enhanced amplification efficiency with TSDBB (Figure 6, MCHR1 target) | 5'-GGGCACCCTACTATGTG-3' | 5'-GCCGCATTGTATAAGTAGA-3 |
| Enhanced amplification efficiency with TSDBB (Figure 6, ATP6V1C1 target) | 5'-CTGTTTGAGAGTTAAATGATGTC-3' | 5'-ACACCTCAGCATATAACAA-3' |
| Enhanced amplification efficiency with TSDBB (Figure 6, ELF5 target) | 5'-CACTCCCTGAAAGAGGA-3' | 5'-CCCAAGCTCCTTCTTCT-3' |
| NTC amplification (Figure 8) | 5'-CTGTTTGAGAGTTAAATGATGTC-3' | 5'-ACACCTCAGCATATAACAA-3' |
| NTC amplification (Figure 9) | 5'-CTGTTTGAGAGTTAAATGATGTC-3' | 5'-ACACCTCAGCATATAACAA-3' |
| NTC amplification (Figure 10) | 5'-CTGTTTGAGAGTTAAATGATGTC-3' | 5'-ACACCTCAGCATATAACAA-3' |
| Valley Tms for different reagents (Figure 11) | 5'CCCTTCTCTCTGCCCCCTGGT 3' | 5'AGGGGTTCCACTACGTAGA'3 |
| Depth of valley with increasing TSDBB concentration (Figure 12) | 5'-CTGTTTGAGAGTTAAATGATGTC-3' | 5'-ACACCTCAGCATATAACAA-3' |
| Valley Tms for different reagents (Figure 14) | 5'CCCTTCTCTCTGCCCCCTGGT 3' | 5'AGGGGTTCCACTACGTAGA'3 |
| Effect of dissolving TSDBB in Water vs Tris (Figure 17) | 5'-GGGCACCCTACTATGTG-3' | 5'-GCCGCATTGTATAAGTAGA-3 |
| Effect of premixing TSDBB with polymerase-NTC samples (Figure 18) | 5'-GGATTATGCCTGGCACCAT-3' | CF460 A24 |
| Effect of premixing TSDBB with polymerase-DNA samples (Figure 19) | 5'-GGATTATGCCTGGCACCAT-3' | CF460 A24 |
| Suppression of type 2 mispriming by TSDBB and PSL. (Figure 20) | 5'-CTGTTTGAGAGTTAAATGATGTC-3' | 5'-ACACCTCAGCATATAACAA-3' |

Figure 23
All Experiments performed as 25 μM reactions in 1x GoTaq Flexi Buffer

| Experiment | Upper primer | Lower primer | DNA | MgCl2 | dNTPs | Polymerase | Hot Start Additive |
|---|---|---|---|---|---|---|---|
| Mispriming suppression by TSDBB (Figure 4) | 300 nM | 300 nM | 17.5 copies/ul of GeneScript HumanGenomic DNA | 3 mM | 250 μ | Flexi GoTaq | 600nM TSDBB |
| TSDBB amplification compared to PSL (Figure 5) | 300 nM | 300 nM | 17.5 copies/ul of GeneScript Human Genomic DNA | 3 mM | 250 μM | Flexi GoTaq | 650nM TSDBB or 650nM PSL |
| Enhanced amplification efficiency with TSDBB (Figure 6, MCHR1 target) | 300 nM | 300 nM | 17.5 copies/ul of GeneScript Human Genomic DNA | 3 mM | 250 μM | Flexi GoTaq or Hot Start GoTaq | 650nM TSDBB or GoTaq Antibody |
| Enhanced amplification efficiency with TSDBB (Figure 6, ATP6V1C1 target) | 300 nM | 300 nM | 17.5 copies/ul of GeneScript Human Genomic DNA | 3 mM | 250 μM | Flexi GoTaq or Hot Start GoTaq | 650nM TSDBB or GoTaq Antibody |
| Enhanced amplification efficiency with TSDBB (Figure 6, ELF5 target) | 300 nM | 300 nM | 17.5 copies/ul of GeneScript Human Genomic DNA | 3 mM | 250 μM | Flexi GoTaq or Hot Start GoTaq | 650nM TSDBB or GoTaq Antibody |
| Delay of Primer-dimer amplification by TSC47D and TSDBB (Figure 7) | 500 nM | 500 nM | Synthetic Target | 5 mM | 200 μM | Flexi GoTaq | 650nM TSDBB or 650nM TSC47D |
| NTC amplification (Figure 8) | 300 nM | 300 nM | none | 3 mM | 250 μM | Flexi GoTaq or Hot Start GoTaq | 650nM TSDBB or GoTaq Antibody |
| NTC amplification (Figure 9) | 300 nM | 300 nM | none | 3 mM | 250 μM | Flexi GoTaq or Hot Start GoTaq | 650nM TSDBB or GoTaq Antibody |
| NTC amplification (Figure 10) | 300 nM | 300 nM | none | 3 mM | 250 μM | Flexi GoTaq or Hot Start GoTaq | 650nM TSDBB or GoTaq Antibody |
| Valley Tms for different reagents (Figure 11) | 300 nM | 300 nM | 17.5 copies/μl of GeneScript Human Genomic DNA | 3 mM | 250 μM | Flexi GoTaq | 650nM TSDBB, 650nM TSC39D, or TSC47D |

Figure 23 (Continued)

| Experiment | Upper primer | Lower primer | DNA | MgCl2 | dNTPs | Polymerase | Hot Start Additive |
|---|---|---|---|---|---|---|---|
| Depth of valley with increasing TSDBB concentration (Figure 12) | 300 nM | 300 nM | 17.5 copies/μl of GeneScript Human Genomic DNA | 3 mM | 250 μM | Flexi GoTaq | 200nM TSDBB or 200nM PSL |
| Method for determining the optimal reagent concentration (Figure 13) | 300 nM | 300 nM | 17.5 copies/μμl of GeneScript Human Genomic DNA | 3 mM | 250 μM | Flexi GoTaq | 650 nM TSDBB, 650 nM TSC39D, or 650 nM TSC47D |
| Valley Tms for different reagents (Figure 14) | 500 nM | 500 nM | Synthetic Target | 5 mM | 200 μM | Flexi GoTaq | 650 nM, 1300 nM TSDBB |
| Probe detection (Figure 15) | 500 nM | 500 nM | Synthetic Target | 5 mM | 200 μM | Flexi GoTaq | 650 nM, 1300nM TSDBB |
| Gel showing TSDBB (Figure 16) | 500 nM | 500 nM | Synthetic Target | 5 mM | 200 μM | Flexi GoTaq | 2000 nM TSDBB |
| Effect of dissolving TSDBB in Water vs Tris (Figure 17) | 300 nM | 300 nM | 17.5 copies/μl of GeneScript Human Genomic DNA | 3 mM | 250 μM | Flexi GoTaq or Hot Start GoTaq | 650nM TSDBB or GoTaq Antibody |
| Effect of premixing TSDBB with polymerase-NTC samples (Figure 18) | 300 nM | 300 nM | 17.5 copies/μl of GeneScript Human Genomic DNA | 3 mM | 250 μM | Flexi GoTaq or Hot Start GoTaq | 650nM TSDBB or GoTaq Antibody |
| Effect of premixing TSDBB with polymerase-DNA samples (Figure 19) | 300 nM | 300 nM | 17.5 copies/μl of GeneScript Human Genomic DNA | 3 mM | 250 μM | Flexi GoTaq or Hot Start GoTaq | 650nM TSDBB or GoTaq Antibody |
| Suppression of type 2 mispriming by TSDBB and PSL (Figure 20) | 300 nM | 300 nM | 17.5 copies/μl of GeneScript Human Genomic DNA | 3 mM | 250 μM | Flexi GoTaq | 200nM TSDBB or 200nM PSL |

Figure 24

| Experiment | Room Temp | Simulat. RT | Ab Denat. | PCR Denat. | PCR Anneal | PCR Exten. | Cycles | Melt Curve |
|---|---|---|---|---|---|---|---|---|
| Mispriming suppression by TSDBB (Figure 4) | 30 min | none | 3 min 95°C | 10 sec 95°C | 30 sec 62°C | 33 sec 72°C | 60 | 40°C to 98°C,58 33 sec cycles, 3 readings/cycle |
| TSDBB amplification compared to PSL (Figure 5) | 30 min | none | 3 min 95°C | 10 sec 95°C | 30 sec 60°C | none | 60 | 35°C to 95°C, 60 30 sec cycles, 3 readings/cycle |
| Enhanced amplification efficiency with TSDBB (Figure 6, MCHR1 target) | 30 min | none | 3 min 95°C | 10 sec 95°C | 30 sec 60°C | none | 60 | N/A |
| Enhanced amplification efficiency with TSDBB (Figure 6, ATP6V1C1 target) | 30 min | none | 3 min 95°C | 10 sec 95°C | 30 sec 60°C | none | 60 | 35°C to 95°C, 60 30 sec cycles, 3 readings/cycle |
| Enhanced amplification efficiency with TSDBB (Figure 6, ELF5 target) | 30 min | none | 3 min 95°C | 10 sec 95°C | 30 sec 60°C | none | 60 | 35°C to 95°C, 60 30 sec cycles, 3 readings/cycle |
| Delay of Primer-dimer amplification by TSC47D and TSDBB (Figure 7) | 1 hr | 10 min 47°C | 10 min 95°C | 20 sec 95°C | 1 min 60°C | none | 45 | 35°C to 95°C, 60 30 sec cycles, 3 readings/cycle |
| NTC amplification (Figure 8) | 30 min | none | 3 min 95°C | 10 sec 95°C | 30 sec 60°C | none | 60 | 35°C to 95°C, 60 30 sec cycles, 3 readings/cycle |
| NTC amplification (Figure 9) | 30 min | none | 3 min 95°C | 10 sec 95°C | 30 sec 60°C | none | 60 | 35°C to 95°C, 60 30 sec cycles, 3 readings/cycle |
| NTC amplification (Figure 10) | 30 min | none | 3 min 95°C | 10 sec 95°C | 30 sec 60°C | none | 60 | 35°C to 95°C, 60 30 sec cycles, 3 readings/cycle |
| Valley Tms for different reagents (Figure 11) | 30 min | none | 3 min 95°C | 10 sec 95°C | 30 sec 62°C | 33 sec 72°C | 60 | 40°C to 98°C,58 33 sec cycles, 3 readings/cycle |
| Depth of valley with increasing TSDBB concentration (Figure 12) | 30 min | none | 3 min 95°C | 10 sec 95°C | 30 sec 60°C | none | 60 | 35°C to 95°C, 60 30 sec cycles, 3 readings/cycle |
| Method for determining the optimal reagent concentration (Figure 13) | 1 hr | 10 min 47°C | 10 min 95°C | 20 sec 95°C | 1 min 60°C | none | 45 | 35°C to 95°C, 60 33 sec cycles, 3 readings/cycle |
| Valley Tms for different reagents (Figure 14) | 30 min | none | 3 min 95°C | 10 sec 95°C | 30 sec 62°C | 33 sec 72°C | 60 | 40°C to 98°C,58 33 sec cycles, 3 readings/cycle |
| Probe detection (Figure 15) | 1 hr | 10 min 47°C | 10 min 95°C | 20 sec 95°C | 1 min 60°C | none | 45 | 35°C to 95°C, 60 33 sec cycles, 3 readings/cycle |
| Gel showing TSDBB (Figure 16) | 1 hr | 10 min 47°C | 10 min 95°C | 20 sec 95°C | 1 min 60°C | none | 45 | 35°C to 95°C, 60 33 sec cycles, 3 readings/cycle |

Figure 24 (Continued)

| Experiment | Room Temp | Simulat. RT | Ab Denat | PCR Denat | PCR Anneal | PCR Exten | Cycles | Melt Curve |
|---|---|---|---|---|---|---|---|---|
| Effect of dissolving TSDBB in Water vs Tris (Figure 17) | 30 min | none | 3 min 95°C | 10 sec 95°C | 30 sec 60°C | none | 60 | 35°C to 95°C, 60 33 sec cycles, 3 readings/cycle |
| Effect of premixing TSDBB with polymerase-NTC samples (Figure 18) | 30 min | none | 3 min 95°C | 10 sec 95°C | 15 sec 64°C | 33 sec 72°C | 60 | 35°C to 95°C, 60 33 sec cycles, 3 readings/cycle |
| Effect of premixing TSDBB with polymerase-DNA samples (Figure 19) | 30 min | none | 3 min 95°C | 10 sec 95°C | 15 sec 64°C | 33 sec 72°C | 60 | 35°C to 95°C, 60 33 sec cycles, 3 readings/cycle |
| Suppression of type 2 mispriming by TSDBB and PSL (Figure 20) | 30 min | none | 3 min 95°C | 10 sec 95°C | 30 sec 60°C | none | 60 | 35°C to 95°C, 60 30 sec cycles, 3 readings/cycle |

Figure 36

| TSD-BB | ● 5' Dabcyl | |
| --- | --- | --- |
| TSBQ0-BB | ◉ 5' Black Hole Quencher 0 | |
| TSBQ1-BB | ◉ 5' Black Hole Quencher 1 | |
| TSBQ2-BB | ◉ 5' Black Hole Quencher 2 | |

Exemplary Double-Stranded Mispriming Prevention Reagent Sequence:

Upper Strand:
Carbon Spacer- 5' GAGCAGACTCGCACTGAGGTA 3' - Biosearch Blue

Lower Strand:
Black Hole Quencher 2- 5' TACCTCAGTGCGAGTCTGCTC 3' – Biosearch Blue Figure 40
A
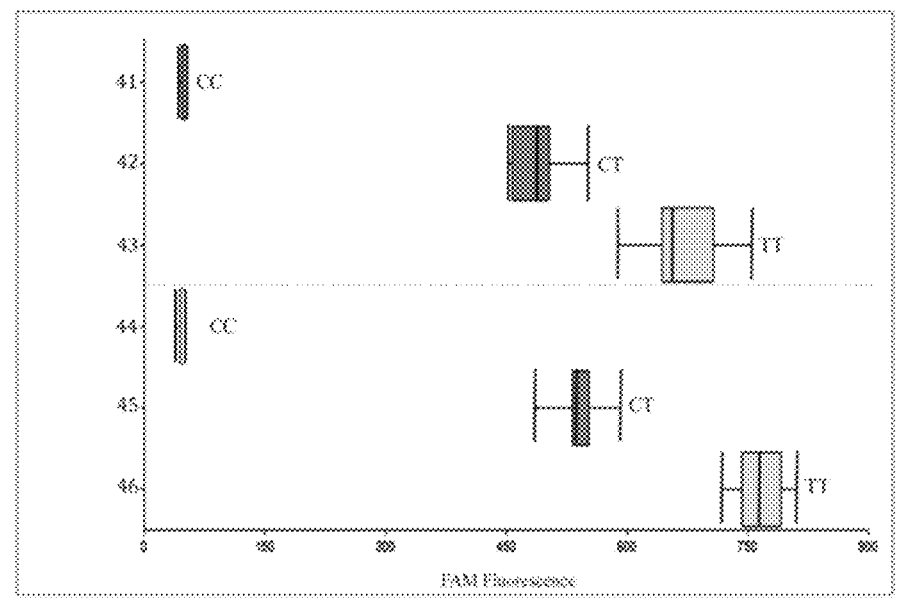
B
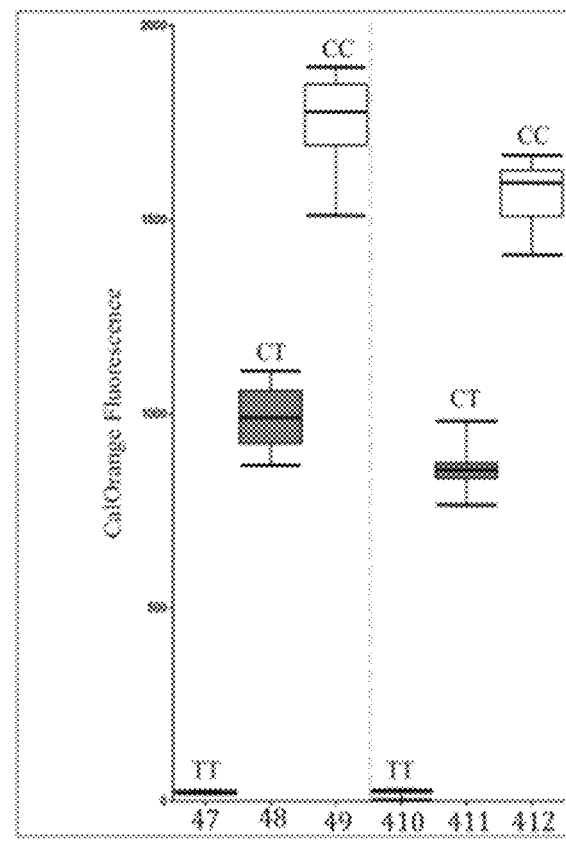

Figure 41
A
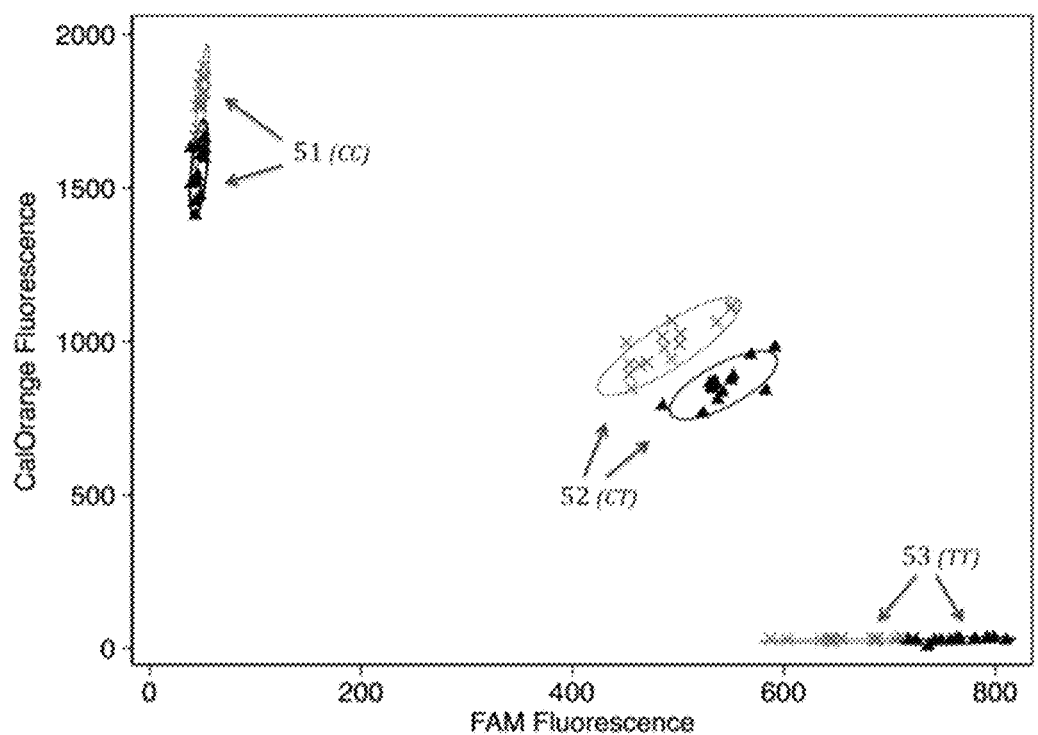
B
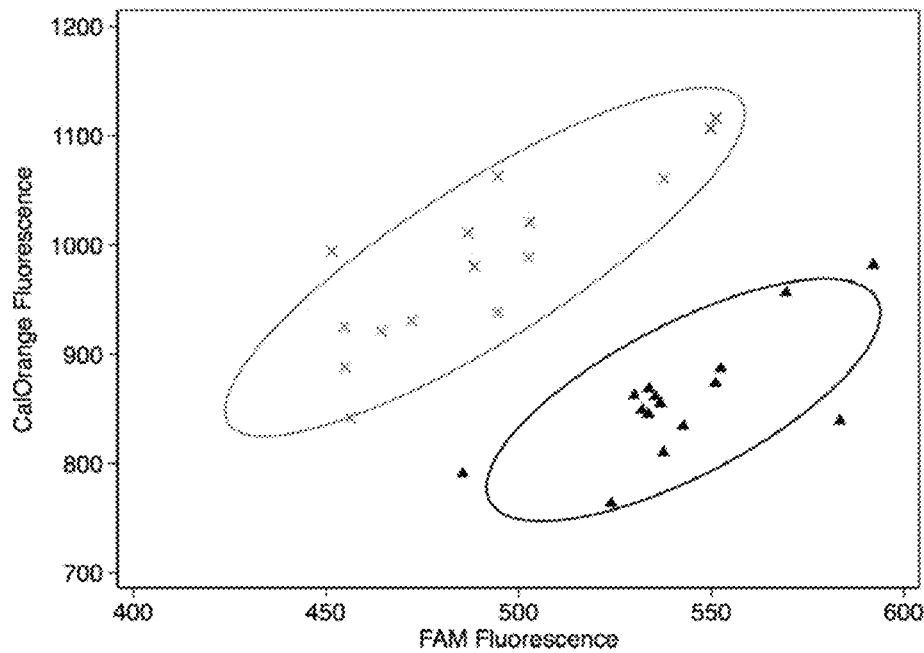

Figure 42

| Squared Mahalanobis Distances between Genotypic Groups | Group 51 to 52 Homozygous CC to Heterozygous TC | | | Group 52 to 53 Heterozygous TC to homozygous TT | | | Group 51 to 53 Homozygous TT to Homozygous CC | | |
|---|---|---|---|---|---|---|---|---|---|
| | Squared Mahalanobis Distance | F Value | P Value | Squared Mahalanobis Distance | F Value | P Value | Squared Mahalanobis Distance | F Value | P Value |
| Without Multi-stranded mispriming Prevention Reagent | 163.2919 | 1224.689 | 1.06E-32 | 107.6839 | 807.6292 | 4.71E-29 | 536.1844 | 4021.383 | 2.46E-43 |
| With 400nM Multi-stranded mispriming Prevention Reagent | 223.6764 | 1677.573 | 1.73E-35 | 159.9265 | 1199.448 | 1.62E-32 | 761.8715 | 5714.036 | 1.64E-46 |
| Δ Distance | 37.0% increase | | | 48.5% increase | | | 42.1% increase | | |

Figure 45
A
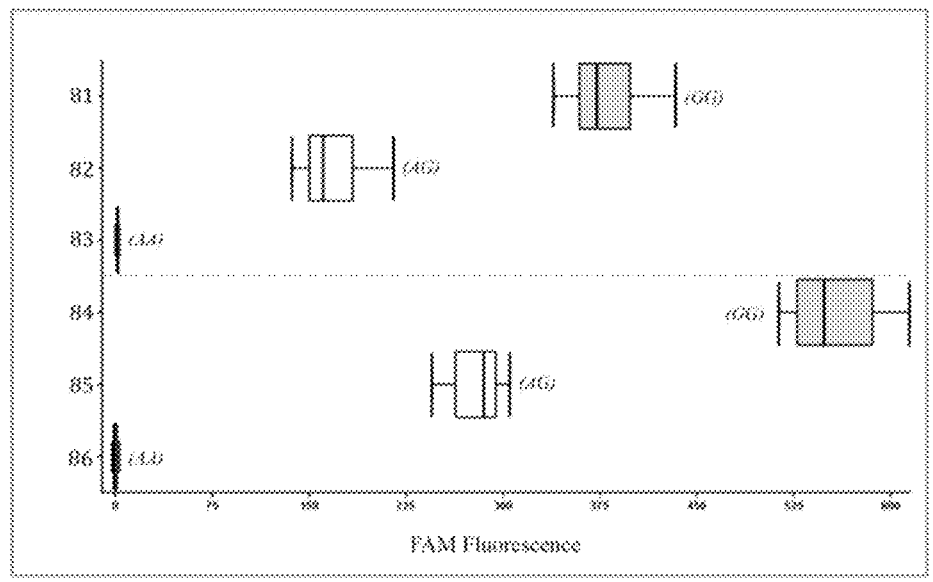
B
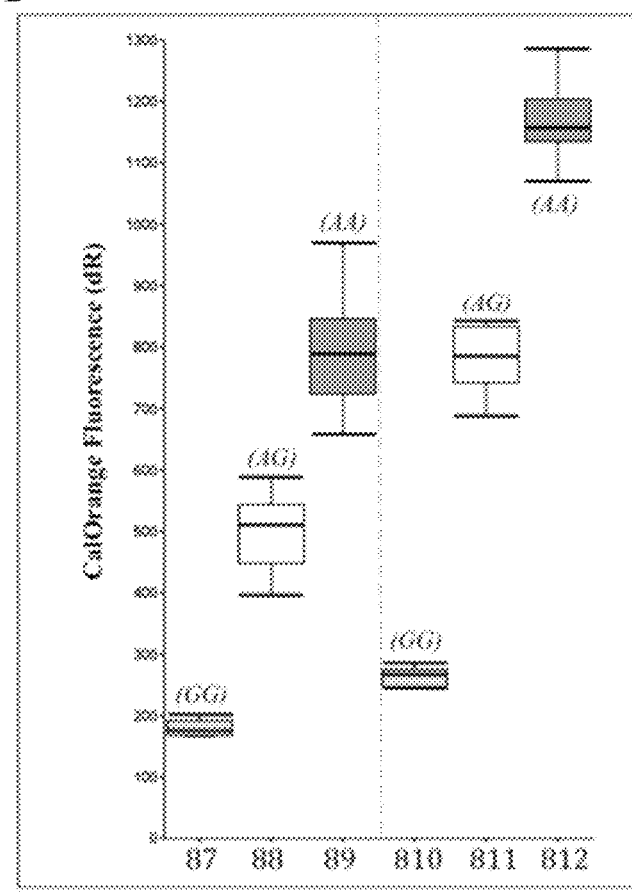

Figure 47
A

| Squared Mahalanobis Distances between Genotypic Groups | Group 91 to 92 Homozygous AA to Heterozygous AG ||| Group 92 to 93 Heterozygous AG to homozygous GG ||| Group 91 to 93 Homozygous GG to Homozygous AA |||
|---|---|---|---|---|---|---|---|---|---|
| | Squared Mahalanobis Distance | F Value | P Value | Squared Mahalanobis Distance | F Value | P Value | Squared Mahalanobis Distance | F Value | P Value |
| Without Multi-stranded mispriming Prevention Reagent | 117.8584 | 942.8673 | 7.93e-32 | 71.70785 | 573.6628 | 3.01e-27 | 373.429 | 2987.432 | 8.57e-43 |
| With 400nM Multi-stranded mispriming Prevention Reagent | 176.9623 | 1032.28 | 4.22e-28 | 181.4176 | 1313.714 | 6.24e-30 | 716.732 | 4300.392 | 4.65e-39 |
| Δ Distance | 50.1% increase | | | 153.0% increase | | | 91.9% increase | | |

| | Regression Analysis of Amplification Curve Shape | | | | | |
|---|---|---|---|---|---|---|
| | Linear Regression Coefficient (1) | Linear Regression t statistic (2) | Linear Regression R-squared Value (3) | Quadratic Regression Coefficient (4) | Quadratic Regression t statistic (5) | Quadratic Regression R-squared Value (6) |
| Without Multi-stranded mispriming Prevention Reagent (Fig_A) | 45.77 | 41.98 | 0.910 | -2.61 | 7.75 | 0.933 |
| With 400 nM Multi-stranded mispriming Prevention Reagent (Fig_B) | 100.48 | 105.08 | 0.9855 | -0.789 | 2.34 | 0.9859 |

Figure 50 (continued)
F

| Chi-squared Test Values for Decreased Scatter at Endpoint |||||| 
|---|---|---|---|---|---|
| Reagent Added | Figure Number | Standard Deviation | Chi-squared Test Value | P-value | Significantly Less Variation? |
| none | 50A | 165.03 | N/A | N/A | N/A |
| 300nM multi-stranded reagent without Terminal Modifiers | 50E | 159.91 | 8.45 | 0.49 | no |
| 50 nM Multi-stranded Mispriming Prevention Reagent | 50B | 44.72 | 0.73 | 4.10E-05 | yes |
| 100 nM Multi-stranded Mispriming Prevention Reagent | 50C | 71.02 | 1.85 | 2.64E-03 | yes |
| 300 nM Multi-stranded Mispriming Prevention Reagent | 50D | 66.18 | 1.45 | 2.48E-03 | yes |

Figure 52

| Chi-squared Test Values for Decreased Scatter at Endpoint ||||
|---|---|---|---|---|
| Reagent Added | Standard Deviation | Chi-Squared Test Value | P-value | Significantly less variation? |
| none | 467.33 | N/A | N/A | N/A |
| 1200nM upper strand of multi-stranded mispriming prevention reagent | 351.92 | 8.50 | 0.90 | no |
| 1200nM lower strand of multi-stranded mispriming prevention reagent | 353.61 | 8.59 | 0.89 | no |

Figure 56

| Experiment | Experiment | Target Gene |
|---|---|---|
| Multi-stranded mispriming prevention reagent: decrease in scatter at endpoint (Figure 39) | Symmetric PCR | BRCA1 |
| Multi-stranded mispriming prevention reagent: increase in fluorescent signal (Figure 44) | Symmetric PCR | XRCC1 |
| Multi-stranded mispriming prevention reagent: concentration dependent decrease in scatter (Figure 49) | Symmetric PCR | TSD |
| Multi-stranded mispriming prevention reagent: necessity of terminal modifiers (Figure 50) | Symmetric PCR | TSD |
| Multi-stranded mispriming prevention reagent: Empirical Tm (Figure 51) | Symmetric PCR | TSD |
| Multi-stranded mispriming prevention reagent: single strands versus double strands (Figure 52) | Symmetric PCR | TSD |

Figure 57

| Experiment | Upper primer Sequence | Lower primer Sequence |
|---|---|---|
| Multi-stranded mispriming prevention reagent: concentration dependent decrease in scatter (Figure 49) | 5'-CCTTCTCTCTGCCCCCTGGT-3' | 5'-AGGGGTTCCACTACGTAGA-3' |
| Multi-stranded mispriming prevention reagent: necessity of terminal modifiers (Figure 50) | 5'-CCTTCTCTCTGCCCCCTGGT-3' | 5'-AGGGGTTCCACTACGTAGA-3' |
| Multi-stranded mispriming prevention reagent: Empirical Tm (Figure 51) | 5'-CCTTCTCTCTGCCCCCTGGT-3' | 5'-AGGGGTTCCACTACGTAGA-3' |
| Multi-stranded mispriming prevention reagent: single strands versus double strands (Figure 52) | 5'-CCTTCTCTCTGCCCCCTGGT-3' | 5'-AGGGGTTCCACTACGTAGA-3' |

Figure 58

| Experiment | Upper primer | Lower primer | DNA | MgCl2 | dNTPs | Polymerase | Hot Start Additive |
|---|---|---|---|---|---|---|---|
| Multi-stranded mispriming prevention reagent: decrease in scatter at endpoint (Figure 39) | | | 1000 copies of Coriele Human Genomic DNA | | | 1X KlearKall Hot-Start Mix | |
| Multi-stranded mispriming prevention reagent: increase in fluorescent signal (Figure 44) | | | 1000 copies of Coriele Human Genomic DNA | | | 1X KlearKall Hot-Start Mix | |
| Multi-stranded mispriming prevention reagent: concentration dependent decrease in scatter (Figure 49) | 300 nM | 300 nM | 1000 copies of Coriele Human Genomic DNA | | | 1X KlearKall Hot-Start Mix | |
| Multi-stranded mispriming prevention reagent: necessity of terminal modifiers (Figure 50) | 300 nM | 300 nM | 1000 copies of Coriele Human Genomic DNA | 3 mM | 250 μM | Flexi GoTaq | 1200nM TSDBB |
| Multi-stranded mispriming prevention reagent: Epirical Tm (Figure 51) | 300 nM | 300 nM | 1000 copies/μl of Coriele Human Genomic DNA | 3 mM | 250 μM | Flexi GoTaq | 1200nM TSDBB |
| Multi-stranded mispriming prevention reagent: single strands versus double strands (Figure 52) | 300 nM | 300 nM | 1000 copies/μl of Coriele Human Genomic DNA | 3 mM | 250 μM | Flexi GoTaq | 1200nM TSDBB |

Figure 59

| Experiment | Ab Denat. | First PCR Segment | Second PCR Segment | Melt Curve | Fluorescent Acquisition |
|---|---|---|---|---|---|
| Multi-stranded mispriming prevention reagent: decrease in scatter at endpoint (Figure 39) | 15 min 95°C | For 60 cycles, 20 seconds at 95°C, 60 seconds at 60°C | None | N/A | 3 fluorescent readings during the extension step |
| Multi-stranded mispriming prevention reagent: increase in fluorescent signal (Figure 44) | 15 min 95°C | For 60 cycles, 20 seconds at 95°C, 60 seconds at 60°C | None | N/A | 3 fluorescent readings during the extension step |
| Multi-stranded mispriming prevention reagent: concentration dependent decrease in scatter (Figure 49) | 3 min 95°C | For 10 cycles, 10 seconds at 95°C, 30 seconds at 62°C, 15 seconds at 72°C | For 50 cycles, 60 seconds at 95°C, 30 seconds at 55°C, 30 seconds at 72°C | N/A | 3 fluorescent endpoint readings during the 2nd Segment extension step |
| Multi-stranded mispriming prevention reagent: necessity of terminal modifiers (Figure 50) | 3 min 95°C | For 10 cycles, 10 seconds at 95°C, 30 seconds at 62°C, 15 seconds at 72°C | For 50 cycles, 60 seconds at 95°C, 30 seconds at 55°C, 30 seconds at 72°C | N/A | 3 fluorescent endpoint readings during the 2nd Segment extension step |
| Multi-stranded mispriming prevention reagent: Empirical Tm (Figure 51) | 3 min 95°C | For 10 cycles, 10 seconds at 95°C, 30 seconds at 62°C, 15 seconds at 72°C | For 50 cycles, 60 seconds at 95°C, 30 seconds at 55°C, 30 seconds at 72°C | Melt from 35°C to 95°C at a rate of 1 degree per second | 3 fluorescent endpoint readings during the 2nd Segment extension step and every cycle of the Melt step |
| Multi-stranded mispriming prevention reagent: single strands versus double strands (Figure 52) | 3 min 95°C | For 10 cycles, 10 seconds at 95°C, 30 seconds at 62°C, 15 seconds at 72°C | For 50 cycles, 60 seconds at 95°C, 30 seconds at 55°C, 30 seconds at 72°C | Melt from 35°C to 95°C at a rate of 1 degree per second | 3 fluorescent endpoint readings during the 2nd Segment extension step and every cycle of the Melt step |

MISPRIMING PREVENTION REAGENTS

RELATED APPLICATIONS

This application claims priority to U.S. Provisional Application No. 62/136,048, filed Mar. 20, 2015, and 62/094,597, filed Dec. 19, 2014, each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Mar 16, 2016, is named BUG-069.01_SL.txt and is 14,065 bytes in size.

BACKGROUND

Mispriming is a significant problem faced when performing primer-dependent amplification processes, such as polymerase chain reaction (PCR). Mispriming is manifest in at least four types: Type 1 mispriming, which occurs during the preparation of reaction mixtures or the execution of other enzymatic manipulations (e.g., reverse transcription in the case of one-step RT-PCR) prior to the start of amplification; Type 2 mispriming, which occurs during an amplification if cycle temperatures include any temperature significantly below the primer annealing temperature, as may occur during the performance of an asymmetric PCR amplifications, such as Linear-After-The-Exponential PCR (LATE-PCR), during which the incubation temperature may be dropped to allow probes with low melting temperatures to bind their target or at the end of an amplification reaction when the sample is cooled down and removed from the thermal cycler prior to a subsequent process such as DNA sequencing; Type 3 mispriming occurs during amplification at cycles having a temperature at or above the primer annealing temperature of the reaction; and Type 4 mispriming, which occurs in the late stages of a amplification after a high concentration of amplicon has been made. Thus, Type 1 and Type 2 mispriming occur below the primer annealing temperature of the amplification reaction, while Type 3 and 4 mispriming occur at or above the primer annealing temperature of the reaction.

One manifestation of Type 1 and Type 2 mispriming is formation of primer-dimers, which occurs when one primer hybridizes to the other primer or to itself and then undergoes extension of the 3' end to generate a small, double-stranded amplicon. This amplicon can then undergo further amplification and/or can form an even larger oligomer. Primer-dimer formation can occur even in the absence of a target nucleic acid sequence. Among the approaches that have been applied to address Type 1 mispriming is the use of an antibody that binds to the DNA polymerase and inhibit the polymerase activity until the reaction is heated to a high temperature, such as 95° C., at which point the antibody is irreversibly denatured and can no longer bind to the polymerase.

Type 1 and Type 2 mispriming can be measured by various methods, including through the use of real-time PCR amplification monitored with fluorescent dyes that interact with double stranded DNA (e.g., SYBR Green 1). For example, for reactions containing targets, mispriming can result in threshold cycle (Ct) values that are lower than the Ct predicted for the number of starting targets and the efficiency of amplification. For reactions with no targets, mispriming can be observed as the presence of real-time amplification signals; the earlier the Ct value of these signals, the greater the incidence of mispriming. Type 1 and Type 2 mispriming can also be measured by first derivative melting curve analysis, where mispriming can be observed as the formation of melting peaks different from the melting peak of the intended amplification product, as shoulders on either side of melting peak of the intended amplification product, or as an increase in the width of the melting peak of the intended amplification product. Type 1 and Type 2 mispriming can also be detected using gel electrophoresis, in which case mispriming can be observed as bands other than the band corresponding to the predicted length of the intended specific amplification product or as higher molecular weight or lower molecular weight smears. Prevention of mispriming results in more efficient use of primers, which is manifest as an increase in the amplification of the intended product.

SUMMARY

In certain aspects, provided herein are mispriming prevention reagents. In some embodiments, the mispriming prevention reagents described herein reduce or prevent Type 1 and/or Type 2 mispriming. In some embodiments, the mispriming prevention reagents reduce or prevent the formation of non-specific products during reverse transcription reactions. In some embodiments, the mispriming prevention reagent provided herein reversibly acquires a principally stem-loop hairpin conformation at a first temperature but not at a second, higher temperature. In some embodiments, the first temperature is a temperature that is below an annealing temperature of an amplification reaction and the second temperature is a temperature that is above the annealing temperature of an amplification reaction. In certain embodiments, the stem-loop hairpin confirmation of the mispriming prevention reagent inhibits the activity and/or increases the specificity of a thermostable DNA polymerase (e.g., Taq polymerase) and or a reverse transcriptase. In some embodiments, the mispriming prevention region comprises non-identical moieties attached to its 5' and 3' termini (not including linkers, if present). In some embodiments, the terminal moieties are cyclic or polycyclic planar moieties that do not have a bulky portion (not including the linker, if present), such as a dabcyl moiety, a Black Hole Quencher moiety (e.g., a Black Hole Quencher 2 or Black Hole Quencher 3 moiety) or a coumarin moiety (e.g., Coumarin 39, Coumarin 47 or Biosearch Blue). In some embodiments, the mispriming prevention reagent contains a loop nucleic acid sequence made up of a single nucleotide repeat sequence (e.g., a poly-cytosine repeat). Thus, in some embodiments, the mispriming prevention reagent is able to act as both a "hot-start" reagent and a "cold-stop" reagent during the performance of a primer-based nucleic acid amplification process.

In certain aspects, provided herein is a multi-stranded mispriming prevention reagent comprising at least two non-identical 5' or 3' terminal moieties (not including linkers, if present). In some embodiments, the multi-stranded mispriming prevention reagent inhibits or prevents Type 3 and/or Type 4 mispriming. In some embodiments, the multi-stranded mispriming prevention reagent comprises a first nucleic acid strand and a second nucleic acid strand that collectively comprise at least two non-identical 5' or 3' terminal moieties. In some embodiments, the at least two non-identical moieties are selected from dabcyl moieties, Black Hole Quencher moieties (e.g., Black Hole Quencher 2 moieties or Black Hole Quencher 3 moieties) and coumarin moieties (e.g., Coumarin 39, Coumarin 47 and Biosearch Blue).

In certain aspects, provided herein is a reaction mixture or a kit comprising a mispriming prevention reagent described herein (e.g., a reaction mixture or a kit for performing an amplification and/or a sequencing reaction). In some embodiments, the reaction mixture or kit further comprises a first nucleic acid primer, a second nucleic acid primer, a thermostable DNA polymerase, a reverse transcriptase, a source of magnesium, amplification buffer and/or dNTPs. In some embodiments, the reaction mixture or kit further comprises a target nucleic acid molecule. In some embodiments, the reaction mixture further comprises a second mispriming prevention reagent (e.g., a multi-stranded mispriming prevention reagent described herein).

In some aspects, provided herein is a method of reducing or preventing mispriming in a nucleic acid amplification reaction, a reverse transcription reaction and/or a nucleic acid sequencing reaction using a mispriming prevention reagent described herein. In certain embodiments, provided herein is a method of creating an amplification product (i.e., an amplicon), wherein the method includes incubating a reaction mixture described herein under conditions such that a primer-based nucleic acid amplification reaction is performed (e.g., a PCR reaction, such as a LATE-PCR reaction, a LEL-PCR reaction or a RT-PCR reaction). In certain embodiments, provided herein is a method of creating a cDNA, wherein the method includes incubating a reaction mixture described herein under conditions such that a reverse transcriptase reaction is performed. In certain embodiments, provided herein is a method of sequencing a target nucleic acid molecule, wherein the method includes incubating a reaction mixture described herein under conditions such a sequencing reaction is performed. In some embodiments, the method further comprises forming the reaction mixture. In some embodiments, the method further comprises incubation of the reaction mixture for various lengths of time and at various temperatures prior to the start of the amplification process. In some embodiments, the method further comprises stopping amplification by lowering the temperature of the reaction and then resuming amplification by warming up the reaction. In some embodiments, the method further comprises detecting the formation of the amplification product. In some embodiments, the method further comprises storing the amplification products for extended periods of time (e.g., for more than 1, 2, 3, 4, 5, 6 or 7 days, and/or for more than 1, 2, 3, 4, 5, 6, 7 or 8 weeks).

BRIEF DESCRIPTION OF FIGURES

FIG. 3 shows the structure of various exemplary single-stranded mispriming prevention reagents described herein.

FIG. 21 is a table providing additional information on certain experiments described herein.

FIG. 22 is a table providing primer sequences used in certain experiments described herein. Upper primer sequences disclosed as SEQ ID NOS 36-38, 37, 39, 37, 37, 37, 36, 37, 36, 38, 40, 40, and 37, respectively, in order of appearance. Lower primer sequences disclosed as SEQ ID NOS 41-43, 42, 44, 42, 42, 42, 41, 42, 41, 43, and 42, respectively, in order of appearance FIG. 23 is a table providing the composition of reaction mixtures used in certain experiments described herein.

FIG. 24 is a table providing PCR and melt curve conditions used in certain experiments described herein.

FIG. 36 shows the structure of an exemplary single-stranded mispriming prevention reagents described herein.

FIG. 40 shows box and whisker plots of the end-point data sets from FIG. 39. The box and whisker plot in FIG. 40 panel A was generated from the end-point data from FIG. 39 panel B and FIG. 39 panel C. The box and whisker plot in FIG. 40 panel B was generated from the end-point data from FIG. 39 panel D and FIG. 39 panel E.

FIG. 41 shows scatter plots of end-point data sets from FIG. 39 with 95% confidence ellipses. The vertical axis is fluorescence detected from probes labeled with Cal Fluor Orange 560. The horizontal axis is fluorescence detected from probes labeled with FAM. Gray points indicate reactions without an exemplary multi-stranded mispriming prevention reagent, Black points indicate reactions with 400 nM of an exemplary multi-stranded mispriming prevention reagent.

FIG. 42 shows a table of statistical distances between genotypic groups in data sets from FIG. 39 panels B-E

FIG. 45 shows box and whisker plots of the end-point data sets from FIG. 44. The box and whisker plot in FIG. 45 panel A was generated from the end-point data from FIG. 44 panel A and FIG. 44 panel B. The box and whisker plot in FIG. 45 panel B was generated from the end-point data from FIG. 44 panel C and 44 panel D.

FIG. 50 panel F shows a table of statistical tests for significant change in endpoint variation in the data from FIG. 50 panels A-E.

FIG. 52 shows a table of statistical tests for significant change in endpoint variation after symmetric amplification of the same assay used in FIGS. 50 and 51, with each strand of the exemplary multi-stranded mispriming prevention reagent added separately at 1200 nM.

FIG. 56 is a table providing additional information on certain experiments described herein.

FIG. 57 is a table providing primer sequences used in certain experiments described herein. Upper primer sequences all disclosed as SEQ ID NO: 36. Lower primer sequences all disclosed as SEQ ID NO: 41.

FIG. 58 is a table providing the composition of reaction mixtures used in certain experiments described herein.

FIG. 59 is a table providing PCR and melt curve conditions used in certain experiments described herein.

DETAILED DESCRIPTION

General

In certain aspects, provided herein are compositions and methods for the prevention of one or more manifestation of misprinting and/or the promotion of the amplification of an intended target nucleic acid sequence during primer-dependent DNA amplification procedures. In certain embodiments, such compositions and methods also reduce or eliminate amplification of un-intended products, including in amplification reactions in which a target nucleic acid sequence is not present. In aspects, provided herein are compositions and methods for reducing or preventing the formation of non-specific products during reverse transcription reactions.

In some embodiments, a mispriming prevention reagent is provided herein that principally has a stem-loop hairpin conformation that inhibits the activity and/or increases the specificity of a thermostable DNA polymerase at a first temperature (e.g., a temperature below an annealing temperature in a nucleic acid amplification procedure) but is principally in a non-hairpin conformation at a second, higher temperature (e.g., a temperature above an annealing temperature in a nucleic acid amplification procedure). Thus, in some embodiments, the mispriming prevention reagent is able to act as both a "hot-start" reagent (inhibiting mispriming before the first time the temperature of the reaction is raised above the annealing temperature) and a "cold-stop" reagent (inhibiting mispriming whenever the temperature is reduced below the annealing temperature).

Figure 1:
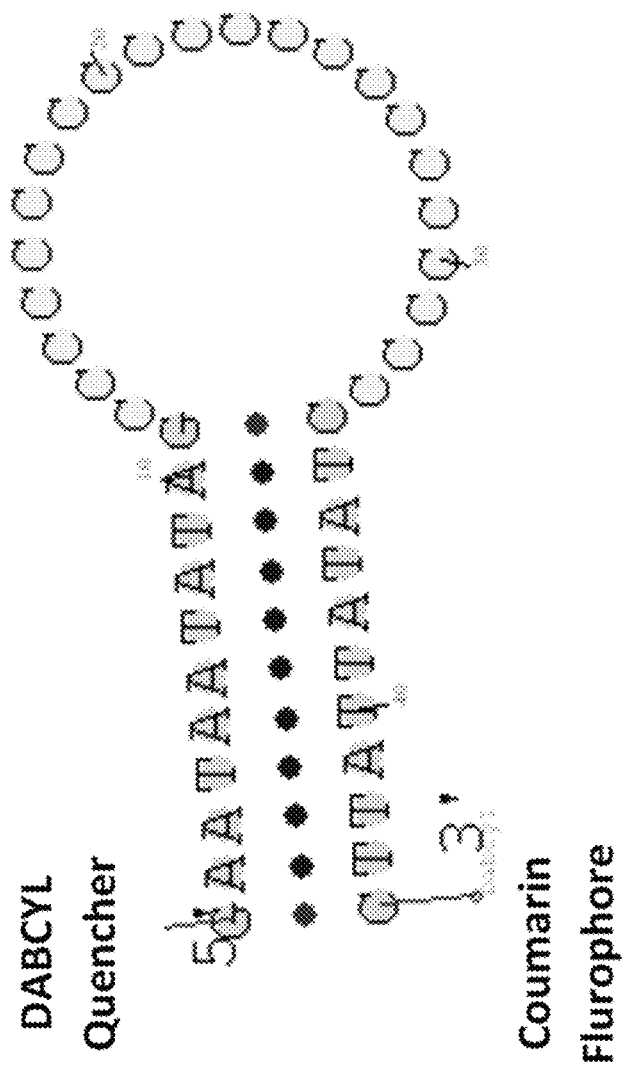
FIG. 1 shows the structure of an exemplary single-stranded mispriming prevention reagent described herein (SEQ ID NO: 45).

FIG. 1 depicts structural features of an exemplary mispriming prevention reagent in the close-hairpin conformation in which it is functionally active. In some embodiments, the mispriming prevention reagents may include one or more of the following features: 1) a loop comprised of only cytosine nucleotides; 2) a stem whose length is at least six base-pairs long; 3) the 3' and 5' terminal base-pair of the stem sequence and/or the base-pair of the stem sequence closest to the loop are either GC or CG, or are comprised of one or more non-natural nucleotides which as a pair have higher melting temperatures than that of an TA or AT pair; 4) the 3' and the 5' ends of the stem are linked to non-identical moieties chosen from the group of cyclic and polycyclic planar moieties that do not have bulky portions, one of which moieties is a quencher of electromagnetic energy including light energy such as fluorescent light emitted from a fluorescent dye bound to the stem.

In some embodiments, provided herein are reaction mixtures and kits comprising the mispriming prevention reagent provided herein and methods of performing an amplification procedure using the mispriming prevention reagent described herein. In some embodiments, also provided herein are multi-stranded mispriming prevention reagents, reagent mixtures and kits comprising such reagents and methods of using such reagents.

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

The terms "hot-start" and "cold-stop" describe the state of a reaction in which the DNA synthetic activity (as distinct from the exonuclease activity) of a DNA polymerase used in an amplification reaction is inhibited by an interaction with a temperature-dependent reagent, antibody and/or alkylating agent or some other means. Hot-start refers to activation of the polymerase by raising the temperature of the reaction above the annealing temperature for first time and holding the high temperature long enough to render the polymerase capable of DNA synthesis. Certain polymerase inhibitor reagents (e.g., certain reagents described herein) are able to be reactivated once the temperature of the reaction is reduced below the annealing temperature. Such reagents are referred to as "cold-stop" reagents.

As used herein, the terms "hybridize" or "hybridization" refer to the hydrogen bonding of complementary DNA and/or RNA sequences to form a duplex molecule. As used herein, hybridization generally takes place under conditions that can be adjusted to a level of stringency that reduces or even prevents base-pairing between a first oligonucleotide primer or oligonucleotide probe and a target sequence, if the complementary sequences are mismatched by as little as one base-pair. In a closed tube reaction, the level of stringency can be adjusted by changing temperature and, as a result, the hybridization of a primer or a probe to a target can occur or not occur depending on temperature. Thus, for example, a probe or a primer that is mismatched to a target can be caused to hybridize to the target by sufficiently lowering the temperature of the solution.

As used herein, the term "Linear-After-The Exponential PCR" or "LATE-PCR" refers to a non-symmetric PCR method that utilizes unequal concentrations of primers and yields single-stranded primer-extension products (referred to herein as amplification products or amplicons). LATE-PCR is described, for example, in U.S. Pat. Nos. 7,198,897 and 8,367,325, each of which is incorporated by reference in its entirety.

As used herein, the term "Linear-Expo-Linear PCR" or "LEL-PCR" refers to a PCR method in which a target nucleic acid sequence undergoes an initial linear amplification process producing an amplification product that is then selectively subjected to LATE-PCR. In LEL-PCR, a sample containing a target nucleic acid is subjected to amplification conditions such that the target nucleic acid sequence first undergoes one or more rounds (e.g., 1-10 rounds) of a linear amplification process to produce a single-stranded amplification product containing a sequence complementary to the target nucleic acid sequence. The sample is then subject to amplification conditions such that the linear amplification products undergo one round of amplification to produce double-stranded amplification products containing a sequence complementary to the target nucleic acid sequence. The sample is then subjected to conditions such that the double-stranded amplification product is subjected to one or more rounds of an exponential amplification process to produce a double-stranded amplification product in which a first strand contains a sequence complementary to the target nucleic acid sequence and a second strand contains a sequence corresponding to the target nucleic acid sequence and complementary to the sequence of the first amplification product strand. Following exponential amplification, the double-stranded amplification product is then subject to a linear amplification process in which a second single-stranded amplification product is generated.

As used herein, Low-Tm probes and Superlow-Tm probes are fluorescently tagged, electrically tagged or quencher tagged oligonucleotides that have a Tm of at least 5° C. below the primer annealing temperature during exponential amplification of a LATE-PCR amplification. In some embodiments sets of signaling and quencher Low-Tm and Superlow-Tm probes are included in LATE-PCR amplification mixtures prior to the start of amplification. There are many possible designs of Low-Tm and Superlow-Tm probes. Molecular beacons, for example, can be designed to be Low-Tm probes by designing them with shorter stems and loops compared standard molecular beacons that hybridize to target strands at or above the primer annealing temperature of the reaction.

As used herein, the term "Lights-On/Lights-Off probes" refers to a probe set that hybridize to adjacent nucleic acid sequences on the single-stranded DNA target to be detected Lights-On/Lights-Off probe technology is more fully described in PCT application No. PCT/US10/53569, hereby incorporated by reference in its entirety.

As used herein, Lights-Off Only probes are probes labeled with a non-fluorescent quencher moiety (e.g., a Black Hole Quencher) that hybridize to a single-stranded DNA target to be detected. Lights-Off Only probes are used in combination with a fluorescent dye that binds preferentially to double-stranded DNA (e.g., SYBR® Green dye) to detect single-stranded amplification products (e.g., single-stranded DNA products produced by LATE-PCR). This is done by subjecting an amplified sample containing the fluorescent ds-DNA dye and the Lights-Off Only probe at multiple temperatures that are below the melting temperature of the probe to excitation at a wavelength appropriate for stimulating the dye and detecting emission at a wavelength appropriate for detecting emission from the dsDNA-dye. Lights-Off Only probe technology is more fully described in U.S. Provisional Application No. 61/702,019, hereby incorporated by reference in its entirety.

The terms "polynucleotide" and "nucleic acid" are used herein interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, synthetic polynucleotides, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified, such as by conjugation with a labeling component.

As used herein, the term "primer annealing temperature" refers to the temperature used for primer binding during the majority of the thermal cycles in a PCR amplification reaction. This definition recognizes the possibility that the annealing temperature during certain thermal cycles, either at the beginning, soon after the beginning, during, or near the end of an amplification reaction can be deliberately chosen to be above, or below, the annealing temperature chosen for the majority of thermal cycles.

As used herein, the Tm or melting temperature of two oligonucleotides is the temperature at which 50% of the oligonucleotide/targets are bound and 50% of the oligonucleotide target molecules are not bound. Tm values of two oligonucleotides are oligonucleotide concentration dependent and are affected by the concentration of monovalent, divalent cations in a reaction mixture. Tm can be determined empirically or calculated using the nearest neighbor formula, as described in Santa Lucia, J. PNAS (USA) 95:1460-1465 (1998), which is hereby incorporated by reference. Tm of a single oligonucleotide that folds on itself to form a hairpin is not dependent on oligonucleotide concentration but is dependent on length and base composition of the sequences that form a stem, as well as on the concentration of the monovalent and divalent cations in the reaction mixture. Generally, the Tm of the mispriming prevention reagents described herein are determined empirically.

Single-Stranded Mispriming Prevention Reagents

In certain aspects, provided herein are single-stranded mispriming prevention reagents. In some embodiments, the reagents described here fall into a class of reagents that, when added to a primer-based amplification reaction, such as PCR assays or other primer-dependent DNA amplification reactions at a functional temperature-dependent concentration relative to the concentration of DNA polymerase in the reaction, is effective in preventing at least one manifestation of mispriming, including amplification of primer-dimers, increasing polymerase selectivity against 3' terminal mismatches, reducing scatter among replicates, and lower than maximal yield of amplification of one or more reaction products.

In certain embodiments, mispriming prevention reagents described herein are capable of preventing or inhibit one or more manifestations of mispriming in at least some PCR amplification reactions and/or reverse transcription reactions. As used herein, "prevent a manifestation of mispriming" refers to the elimination or the reduction of the formation of one or more products of mispriming in a nucleic acid amplification reaction containing a reagent described herein compared to in an otherwise identical nucleic acid amplification reaction in which the reagent was omitted.

In certain embodiments, the reagents described herein comprise a single-stranded oligonucleotide that can be in an open configuration or a closed-hairpin configuration depending on whether six or more complementary nucleotides at or near the 3' terminus and the 5' terminus of the oligonucleotide are hybridized to each other in a temperature-dependent manner. The reagent is active (i.e., inhibits mispriming) in the closed stem-loop hairpin conformation. In this conformation it binds to and increases the specificity of the DNA polymerase, including by greatly reducing the rate of DNA synthesis.

Thus, in certain embodiments the mispriming prevention reagents described herein reduce or prevent Type 1 and/or Type 2 mispriming. In some embodiments, the mispriming prevention reagent provided herein reversibly acquires a principally stem-loop hairpin conformation at a first temperature but not at a second, higher temperature. In some embodiments, the first temperature is a temperature that is below an annealing temperature of an amplification reaction and the second temperature is a temperature that is above the annealing temperature of an amplification reaction. In certain embodiments, the stem-loop hairpin confirmation of the mispriming prevention reagent reduces the activity of a thermostable DNA polymerase (e.g., Taq polymerase). Thus, in some embodiments, the mispriming prevention reagent is able to act as both a "hot-start" reagent and a "cold-stop" reagent during the performance of a primer-based nucleic acid amplification process.

As described herein, the melting temperature, Tm, of a hairpin reagent having a stem of fixed sequence can be adjusted by increasing or decreasing the number of cytosine nucleotides in the loop. However, while hairpin Tm decreases as a function of increasing loop length, the relationship between loop length and hairpin Tm is not linear. Moreover, the empirically observed hairpin Tm differs from the in silico calculated Tm due the presence of the chemical moieties linked to the 3' and 5' ends of the stem. In general, paired identical moieties stabilize the closed stem structure to a greater extent than paired non-identical moieties. In some embodiment, the reagent described herein comprises non-identical 3' and 5' paired moieties.

In some embodiments, the mispriming prevention reagent oligonucleotide described herein comprises, in 5' to 3' order, a first condition-dependent "stem" region, a condition-dependent "loop" region and a second condition-dependent "stem" region, wherein the first stem region hybridizes to the second stem region in a temperature dependent manner to acquire a stem-loop hairpin conformation (e.g., a stem-loop hairpin with a 3' or 5' overhang or a blunt-ended stem-loop hairpin). In some embodiments, the first stem region is linked to a first moiety and the second stem region is linked to a second, non-identical moiety. In some embodiments, the first moiety and the second moiety are cyclic or polycyclic planar moieties that do not have a bulky portion (e.g., a dabcyl moiety, a Black Hole Quencher moiety, such as a Black Hole Quencher 2 moiety or a coumarin moiety).

In some embodiments, the first stem region comprises a first stem nucleic acid sequence (e.g., a nucleic acid sequence of at least 6, 7, 8, 9 or 10 nucleotides in length). In some embodiments, the first stem nucleic acid sequence is no more than 20, 19, 18, 17, 16, 15, 14, 12 or 11 nucleotides in length. In some embodiments, the first stem nucleic acid sequence is 10 nucleotides in length. In some embodiments, the first stem region comprises a 5' terminal moiety. In some embodiments, the 5' terminal moiety is linked (either directly or indirectly) to the most 5' nucleotide of the first stem region. In some embodiments, the 5' terminal moiety is linked (either directly or indirectly) to one of the 2, 3, 4, or 5 most 5' nucleotides of the first stem region. In some embodiments, the 5' terminal moiety comprises a cyclic or polycyclic planar moiety that does not have a bulky portion (not including the linker, if present). In some embodiments, the 5' terminal moiety is a dabcyl moiety. In some embodiments, the 5' terminal moiety is a coumarin moiety (e.g., Coumarin 39, Coumarin 47 or Bioseach Blue).

In some embodiments, the loop region comprises a loop nucleic acid sequence (e.g., a nucleic acid sequence of at least 3, 4, 5, 6, 7, 8, 9, 10, 11, 12, 13, 14, 15, 16, 17, 18, 19, 20, 21, 22, 23, 24 or 25 nucleotides in length). In some embodiments, the loop nucleic acid sequence is between 25 and 40 nucleotides in length. In some embodiments, the loop nucleic acid sequence is a single nucleotide repeat sequence (e.g., a poly-cytosine, a poly-guanine, a poly-thymine, a poly-adenine or a poly-uracil sequence). Use of a single nucleotide sequence, particularly cytosines, for the loop reduces the possibility of the loop sequence base-pairing within the loop or with naturally occurring nucleic acid sequences that may be present in an amplification reaction. In some embodiments, the single nucleotide repeat sequence is a poly-cytosine sequence.

In some embodiments, the second stem region comprises a second stem nucleic acid sequence (e.g., a nucleic acid sequence of at least 6, 7 or 8 nucleotides in length). In some embodiments, the second stem nucleic acid sequence is no more than 20, 19, 18, 17, 16, 15, 14, 12 or 11 nucleotides in length. In some embodiments, the second stem nucleic acid sequence is 10 nucleotides in length. In some embodiments, the second stem nucleic acid sequence is complementary to the second stem nucleic acid sequence. In some embodiments, the second stem region comprises a 3' terminal moiety. In some embodiments, the 3' terminal moiety is linked (either directly or indirectly) to the most 3' nucleotide of the second stem region. In some embodiments, the 3' terminal moiety is linked (either directly or indirectly) to one of the 2, 3, 4, or 5 most 3' nucleotides of the second stem region. In some embodiments, the 3' terminal moiety comprises a cyclic or polycyclic planar moiety that does not have a bulky portion (not including the linker, if present). In some embodiments, the 3' terminal moiety is a dabcyl moiety. In some embodiments, the 3' terminal moiety is a coumarin moiety (e.g., Coumarin 39, Coumarin 47 or Biosearch Blue). In some embodiments, the 3' terminal moiety is non-identical to the 5' terminal moiety. In some embodiments, the 3' terminus of the second stem region is non-extendable by a DNA polymerase.

In some embodiments, the first stem region hybridizes to the second stem region in a temperature dependent manner to acquire a stem-loop hairpin conformation. In some embodiments, the stem-loop conformation comprises a 3' or 5' overhang of 0, 1, 2, 3, 4 or 5 nucleotides. In some embodiments, the first stem region hybridizes to the second stem region with a melting temperature that is at least 30° C., 31° C., 32° C., 33° C., 34° C., 35° C., 36° C., 37° C., 38° C., 39° C., 40° C., 41° C., 42° C., 43° C., 44° C. or 45° C. In some embodiments, the first stem region hybridizes to the second stem region with a melting temperature that is no greater than 71° C., 70° C., 69° C., 68° C., 67° C., 66° C., 65° C., 64° C., 63° C., 62° C., 61° C., 60° C., 59° C., 58° C., 57° C., 56° C., 55° C., 54° C., 53° C., 52° C., 51° C. or 50° C. In some embodiments, the first stem region hybridizes to the second stem region with a melting temperature that is between 40° C. and 71° C., between 40° C. and 55° C. or between 45° C. and 55° C. In some embodiments, the first stem region hybridizes to the second stem region with a melting temperature that is less than the annealing temperature of a nucleic acid amplification reaction (e.g., between 0 and 10° C. less than the annealing temperature, between 0 and 9° C. less than the annealing temperature, between 0 and 8° C. less than the annealing temperature, between 0 and 7° C. less than the annealing temperature, between 0 and 6° C. less than the annealing temperature or between 0 and 5° C. less than the annealing temperature).

In some embodiments, the mispriming prevention reagents described herein include a G/C clamp at one or both ends of the stem regions. In some embodiments, the most 3' nucleic acid of the first stem nucleic acid sequence is cytosine and the most 5' nucleic acid of the second stem nucleic acid sequence is guanine. In some embodiments, the most 3' nucleic acid of the first stem nucleic acid sequence is guanine and the most 5' nucleic acid of the second stem nucleic acid sequence is a cytosine. In some embodiments, the most 5' nucleic acid of the first stem nucleic acid sequence is cytosine and the most 3' nucleic acid of the second stem nucleic acid sequence is guanine. In some embodiments, the most 5' nucleic acid of the first stem nucleic acid sequence is guanine and the most 3' nucleic acid of the second stem nucleic acid sequence is a cytosine.

In some embodiments, the reagent does not fluoresce when present in an amplification reaction. In some embodiments, the reagent does not fluoresce because is not stimulated with an appropriate excitation wavelength. In some embodiments, the reagent does not fluoresce because it does not comprise a fluorescent moiety. In some embodiments, the 3' terminal moiety and/or the 5' terminal moiety is a quencher of electromagnetic energy, including fluorescent light released from a fluorescent DNA-binding dye, such as SYBR Green, that intercalates into the stem of the closed-hairpin.

Multi-Stranded Mispriming Prevention Reagents

Figure 35:
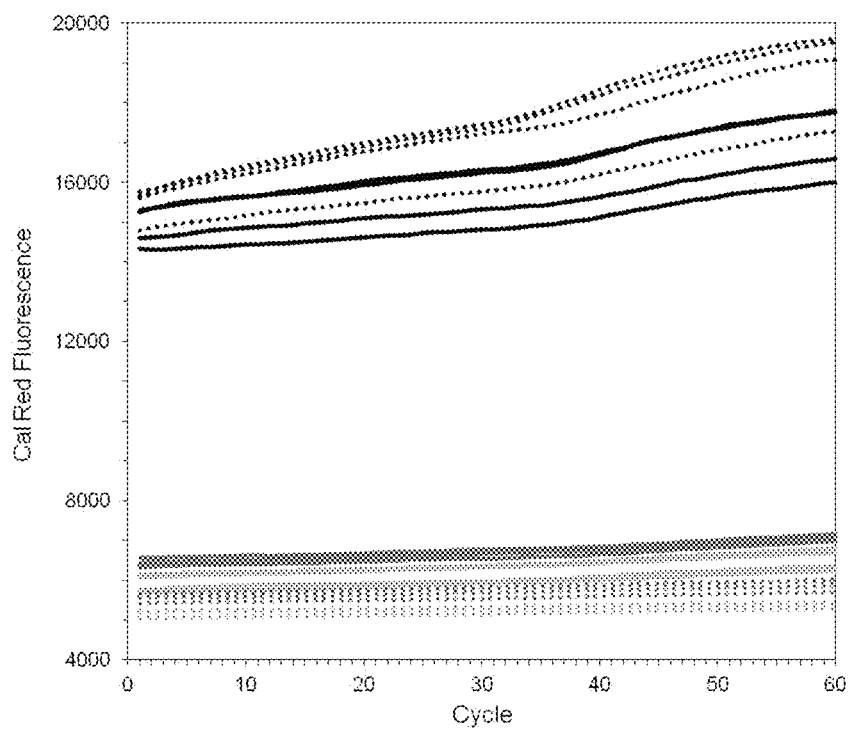
FIG. 35 shows raw Cal Red fluorescence during the symmetric PCR phase of one-step RT-PCR in samples containing SuperScript III and AmpliTaq Gold and either no additives (black lines), PSL (medium gray), or BHQ2BB (light gray). Samples containing HCV AR are indicated by the solid lines; samples without template are indicated by the dotted lines.

In certain aspects, provided herein is a multi-stranded mispriming prevention reagent comprising at least two non-identical 5' or 3' terminal moieties. In some embodiments, the multi-stranded mispriming prevention reagent is a double-stranded mispriming prevention reagent. In some embodiments, the multi-stranded mispriming prevention reagent inhibits or prevents Type 3 and/or Type 4 mispriming. The structure and sequence of an exemplary multi-stranded mispriming prevention reagent according to some embodiments is depicted in FIG. 35.

In some embodiments, the multi-stranded mispriming prevention reagent comprises a first nucleic acid strand of and a second nucleic acid strand. In some embodiments, the first and/or second nucleic acid strand of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides in length. In some embodiments, the first and/or second nucleic acid strand is between 18 and 24 nucleotides in length. In some embodiments, the first and/or second nucleic acid strand is between 20 and 22 nucleotides in length. In some embodiments, the first and/or second nucleic acid strand is 21 nucleotides in length. In some embodiments, the first and second strand are the same length. In some embodiments, the first and second strand are different lengths. In some embodiments, the first nucleic acid strand hybridizes to the second nucleic acid strand with a melting temperature that is no less than 25° C., 30° C., 32° C., 35° C., 40° C., 41° C., 42° C., 43° C., 44° C., 45° C., 46° C., 47° C., 48° C., 49° C. or 50° C. In some embodiments, the first nucleic acid strand hybridizes to the second nucleic acid strand with a melting temperature that is no greater than 77° C., 76° C., 75° C., 74° C., 73° C., 72° C., 71° C., 70° C., 69° C., 68° C., 67° C., 66° C., 65° C., 64° C., 63° C., 62° C., 61° C. or 60° C.

In some embodiments, first and second nucleic acid strand collectively comprise at least two non-identical 5' or 3' terminal moieties (e.g., 2, 3 or 4 terminal moieties). In some embodiments, the at least two non-identical moieties are selected from dabcyl moieties, Black Hole Quencher moieties and coumarin moieties. In some embodiments, the at least two non-identical moieties comprise a dabcyl moiety and a coumarin moiety (e.g., Coumarin 39, Coumarin 47 and Biosearch Blue). In some embodiments, one of the non-identical moieties is located at the 5' terminus of the first nucleic acid strand and one of the non-identical moieties is located at the 3' terminus of the second nucleic acid strand. In some embodiments, one of the non-identical moieties is located at the 3' terminus of the first nucleic acid strand and one of the non-identical moieties is located at the 5' terminus of the second nucleic acid strand. In some embodiments, a dabcyl moiety is located at the 5' terminus of the first nucleic acid strand and a Biosearch Blue moiety is located at the 3' terminus of the second nucleic acid strand. In some embodiments, a Biosearch Blue moiety is located at the 5' terminus of the first nucleic acid strand and a dabcyl moiety is located at the 3' terminus of the second nucleic acid strand. In some embodiments, a coumarin moiety is located at the 3' terminus of the first strand and the 3' terminus of the second strand and a Biosearch Blue moiety is located at the 5' terminus of the second strand. In some embodiments, a carbon spacer is located at the 5' terminus of the first strand. In some embodiments, the non-identical terminal moieties are linked (either directly or indirectly) to the most 3' or the most 5' nucleotide of the first or second nucleic acid strand. In some embodiments, the non-identical terminal moieties are linked (either directly or indirectly) to one of the 2, 3, 4, or 5 most 3' or most 5' nucleotides of the first or second nucleic acid strand.

Reaction Mixtures

In certain aspects, provided herein is a reaction mixture comprising a mispriming prevention reagent described herein. In some embodiments, the mispriming prevention reagent is present in the reaction mixture at a concentration sufficient to reduce or inhibit mispriming in an amplification reaction performed in the reaction mixture and/or to improve the fidelity of a reverse transcription reaction. In some embodiments, the mispriming prevention reagent is present at a concentration of at least 50 nM, 100 nM, 200 nM, 300 nM, 400 mM, 450 nM, 500 nM, 550 nM, 600 nM, 650 nM 800 nM, 900 nM, 1000 nM, 1,200 nM or even up to 2,400 nM. The appropriate concentration for use in a reaction depends on both the number of units of the DNA polymerase and/or reverse transcriptase and the temperature at which the reaction is incubated.

In some embodiments, the reaction mixture further comprises a first nucleic acid primer that hybridizes to a 3' region of a target nucleic acid sequence with a first melting temperature. In some embodiments, the reaction mixture further comprises a second nucleic acid primer that hybridizes to a 3' region of the complement of the target nucleic acid sequence with a second primer melting temperature. In some embodiments, the first and second primer are designed to amplify the target nucleic acid sequence in a PCR amplification reaction. In some embodiments, the first and second primer are present in the reaction mixture at concentrations sufficient for the performance of a PCR amplification reaction (e.g., at least 25 nM, 50 nM, 75 nM, 100 nM, 150 nM, 200 nM, 250 nM, 300 nM, 350 nM, 400 nM, 450 nM.500 nM or 1000 nM). In some embodiments, the first primer is present in the reaction mixture at a concentration that is at least 2-fold higher, at least 3-fold higher, at least 4-fold higher or at least 5 fold higher, than the concentration of the second primer. In some embodiments, the second primer is present in the reaction mixture at a concentration that is at least 2-fold higher, at least 3-fold higher, at least 4-fold higher or at least 5 fold higher, than the concentration of the first primer. Reaction mixtures having uneven primer concentrations can be used, for example, for performing LATE-PCR or LEL-PCR reactions.

In some embodiments, the reaction mixture further comprises a thermostable DNA polymerase. In some embodiments the thermostable DNA polymerase is Taq DNA polymerase, TFI DNA polymerase, Pfu DNA polymerase, Bst DNA polymerase, Vent$_R$ DNA polymerase or Deep Vent$_R$ DNA polymerase. In some embodiments, the thermostable DNA polymerase is Taq DNA polymerase, including, Klear-Kall polymerase from LGC Biosearch, Taq polymerase from Hain Lifescience. In some embodiments, the thermostable DNA polymerase is present in the reaction mixture at a concentration sufficient for the performance of a PCR amplification reaction (e.g., at least 0.5 mM, 1 mM, 1.5 mM or 2 mM). In some embodiments, the reaction mixture comprises a reverse transcriptase.

In some embodiments, the reaction mixture further comprises dNTPs (e.g., dATP, dCTP, dGTP, dTTP, and/or dUTP). In some embodiments, the dNTPs are present in the reaction mixture at a concentration sufficient for the performance of a PCR amplification reaction (e.g., at least 50 µM, 75 µM, 100 µM, 150 µM, 200 µM, 300 µM, 400 µM or 500 µM).

In some embodiments, the reaction mixture further comprises a target nucleic acid molecule comprising the target nucleic acid sequence. In some embodiments, the mispriming prevention reagent does not hybridize to the target nucleic acid molecule with a melting temperature of greater than the stem melting temperature. In some embodiments, the mispriming prevention reagent does not hybridize to the target nucleic acid molecule with a melting temperature of greater than 25° C., 30° C., 32° C., 35° C., 40° C., 41° C., 42° C., 43° C., 44° C., 45° C., 46° C., 47° C., 48° C. or 49° C. In some embodiments, the mispriming prevention reagent does not hybridize to any other target nucleic acid molecule with a melting temperature of greater than the stem melting temperature. In some embodiments, the mispriming prevention reagent does not hybridize to any other nucleic acid molecule in the reaction mixture with a melting temperature of greater than 25° C., 30° C., 32° C., 35° C., 40° C., 41° C., 42° C., 43° C., 44° C., 45° C., 46° C., 47° C., 48° C. or 49° C.

In some embodiments, the first stem region of the mispriming prevention reagent hybridizes to the second stem region with a stem melting temperature that is no greater than the first primer melting temperature and/or the second primer melting temperature (e.g., between 0 and 10° C. less, between 0 and 9° C. less, between 0 and 8° C. less, between 0 and 7° C. less, between 0 and 6° C. or between 0 and 5° C. less than the first primer melting temperature and/or the second primer melting temperature).

In some embodiments, the reaction mixture further comprises a second mispriming prevention reagent. In some embodiments, the second mispriming prevention reagent is a multi-stranded mispriming prevention reagent described herein. In some embodiments, the second mispriming prevention reagent inhibits or prevents Type 3 and/or Type 4 mispriming. In some embodiments, the multi-stranded mispriming prevention reagent is a reagent described in U.S. Pat. Pub. Nos. 2012/0088275 and 2014/0206564, each of which is hereby incorporated by reference in its entirety.

In some embodiments, the second mispriming prevention reagent of the reaction mixture comprises a first nucleic acid strand of and a second nucleic acid strand. In some embodiments, the first and/or second nucleic acid strand of at least 6 nucleotides in length. In some embodiments, the first nucleic acid strand hybridizes to the second nucleic acid strand with a melting temperature that is no less than 25° C., 30° C., 32° C., 35° C., 40° C., 41° C., 42° C., 43° C., 44° C., 45° C., 46° C., 47° C., 48° C., 49° C. or 50° C. In some embodiments, the first nucleic acid strand hybridizes to the second nucleic acid strand with a melting temperature that no greater than 77° C., 76° C., 75° C., 74° C., 73° C., 72° C., 71° C., 70° C., 69° C., 68° C., 67° C., 66° C., 65° C., 64° C., 63° C., 62° C., 61° C. or 60° C.

In some embodiments, the first and second nucleic acid strands collectively comprise at least one 5' or 3' terminal moiety. In some embodiments, the terminal moiety comprises a cyclic or polycyclic planar moiety that does not have a bulky portion (not including the linker, if present). In some embodiments, the terminal moiety is a dabcyl moiety. In some embodiments, the terminal moiety is a coumarin moiety (e.g., Coumarin 39, Coumarin 47 or Biosearch Blue). In some embodiments, the terminal moiety is linked (either directly or indirectly) to the most 3' or the most 5' nucleotide of the first or second nucleic acid strand. In some embodiments, the terminal moiety is linked (either directly or indirectly) to one of the 2, 3, 4, or 5 most 3' or most 5' nucleotides of the first or second nucleic acid strand.

In some embodiments, the first and second nucleic acid strands of the second mispriming prevention reagent collectively comprise at least two 5' or 3' terminal moieties (e.g., 2, 3 or 4 terminal moieties). In some embodiments, the at least two terminal moieties are cyclic or polycyclic planar moieties that do not have a bulky portion (not including the linker, if present). In some embodiments, the at least two terminal moieties are selected from dabcyl moieties and coumarin moieties. In some embodiments, the at least two terminal moieties are dabcyl moieties. In some embodiments, the terminal moieties are coumarin moieties (e.g., Coumarin 39, Coumarin 47 or Biosearch Blue). In some embodiments, the terminal moieties are linked (either directly or indirectly) to the most 3' or the most 5' nucleotide of the first or second nucleic acid strand. In some embodiments, the terminal moieties are linked (either directly or indirectly) to one of the 2, 3, 4, or 5 most 3' or most 5' nucleotides of the first or second nucleic acid strand. In some embodiments, the second mispriming prevention reagent comprises at least two non-identical 5' or 3' terminal moieties. In some embodiments, the at least two non-identical moieties are selected from dabcyl moieties, Black Hole Quencher moieties and coumarin moieties. In some embodiments, the at least two non-identical moieties comprise a dabcyl moiety and a coumarin moiety (e.g., Coumarin 39, Coumarin 47 and Biosearch Blue). In some embodiments, one of the non-identical moieties is located at the 5' terminus of the first nucleic acid strand and one of the non-identical moieties is located at the 3' terminus of the second nucleic acid strand. In some embodiments, one of the non-identical moieties is located at the 3' terminus of the first nucleic acid strand and one of the non-identical moieties is located at the 5' terminus of the second nucleic acid strand. In some embodiments, the non-identical terminal moieties are linked (either directly or indirectly) to the most 3' or the most 5' nucleotide of the first or second nucleic acid strand. In some embodiments, the non-identical terminal moieties are linked (either directly or indirectly) to one of the 2, 3, 4, or 5 most 3' or most 5' nucleotides of the first or second nucleic acid strand.

Kits

In certain aspects, provided herein is a kit comprising a mispriming prevention reagent described herein. In some embodiments, the reaction mixture further comprises a first nucleic acid primer that hybridizes to a 3' region of a target nucleic acid sequence with a first melting temperature. In some embodiments, the reaction mixture further comprises a second nucleic acid primer that hybridizes to a 3' region of the complement of the target nucleic acid sequence with a second primer melting temperature. In some embodiments, the kit further comprises a thermostable DNA polymerase (e.g., Taq DNA polymerase, TFI DNA polymerase, Pfu DNA polymerase, Bst DNA polymerase, $Vent_R$ DNA polymerase Deep $Vent_R$ DNA polymerase, KlearKall polymerase from LGC Biosearch, Taq polymerase from Hain Lifescience). In some embodiments, the kit comprises a reverse transcriptase. In some embodiments, the kit further comprises dNTPs (e.g., dATP, dCTP, dGTP, dTTP, and/or dUTP). In certain embodiments, the kit further comprises instructions for using the mispriming prevention reagent in an amplification reaction. In certain embodiments, the kit further comprises instructions for using the mispriming prevention reagent in a reverse transcription reaction.

In some embodiments, the kit further comprises a target nucleic acid molecule comprising the target nucleic acid sequence. In some embodiments, the mispriming prevention reagent does not hybridize to the target nucleic acid molecule with a melting temperature of greater than the stem melting temperature. In some embodiments, the mispriming prevention reagent does not hybridize to the target nucleic acid molecule with a melting temperature of greater than 25° C., 30° C., 32° C., 35° C., 40° C., 41° C., 42° C., 43° C., 44° C., 45° C., 46° C., 47° C., 48° C. or 49° C. In some embodiments, the mispriming prevention reagent does not hybridize to any other target nucleic acid molecule with a melting temperature of greater than the stem melting temperature. In some embodiments, the mispriming prevention reagent does not hybridize to any other nucleic acid molecule in the reaction mixture with a melting temperature of greater than 25° C., 30° C., 32° C., 35° C., 40° C., 41° C., 42° C., 43° C., 44° C., 45° C., 46° C., 47° C., 48° C. or 49° C.

In some embodiments, the first stem region of the mispriming prevention reagent hybridizes to the second stem region with a stem melting temperature that is no greater than the first primer melting temperature and/or the second primer melting temperature (e.g., between 0 and 10° C. less, between 0 and 9° C. less, between 0 and 8° C. less, between 0 and 7° C. less, between 0 and 6° C. or between 0 and 5° C. less than the first primer melting temperature and/or the second primer melting temperature).

In some embodiments, the kit further comprises a second mispriming prevention reagent. In some embodiments, the second mispriming prevention reagent is a multi-stranded mispriming prevention reagent described herein. In some embodiments, the second mispriming prevention reagent inhibits or prevents Type 2 and/or Type 3 mispriming.

In some embodiments, the second mispriming prevention reagent of the kit comprises a first nucleic acid strand of and a second nucleic acid strand. In some embodiments, the first and/or second nucleic acid strand of at least 6 nucleotides in length. In some embodiments, the first nucleic acid strand hybridizes to the second nucleic acid strand with a melting temperature that is no less than 25° C., 30° C., 32° C., 35° C., 40° C., 41° C., 42° C., 43° C., 44° C., 45° C., 46° C., 47° C., 48° C., 49° C. or 50° C. In some embodiments, the first nucleic acid strand hybridizes to the second nucleic acid strand with a melting temperature that no greater than 77° C., 76° C., 75° C., 74° C., 73° C., 72° C., 71° C., 70° C., 69° C., 68° C., 67° C., 66° C., 65° C., 64° C., 63° C., 62° C., 61° C. or 60° C.

In some embodiments, the first and second nucleic acid strands collectively comprise at least one 5' or 3' terminal moiety. In some embodiments, the terminal moiety comprises a cyclic or polycyclic planar moiety that does not have a bulky portion (not including the linker, if present). In some embodiments, the terminal moiety is a dabcyl moiety. In some embodiments, the terminal moiety is a coumarin moiety (e.g., coumarin 39, coumarin 47 or Biosearch Blue). In some embodiments, the terminal moiety is linked (either directly or indirectly) to the most 3' or the most 5' nucleotide of the first or second nucleic acid strand. In some embodiments, the terminal moiety is linked (either directly or indirectly) to one of the 2, 3, 4, or 5 most 3' or most 5' nucleotides of the first or second nucleic acid strand.

In some embodiments, the first and second nucleic acid strands of the second mispriming prevention reagent collectively comprise at least two 5' or 3' terminal moieties (e.g., 2, 3 or 4 terminal moieties). In some embodiments, the at least two terminal moieties are cyclic or polycyclic planar moieties that do not have a bulky portion (not including the linker, if present). In some embodiments, the at least two terminal moieties are selected from dabcyl moieties, Black Hole Quencher moieties (e.g., Black Hole Quencher 2 moieties) and coumarin moieties. In some embodiments, the at least two terminal moieties are dabcyl moieties. In some embodiments, the terminal moieties are coumarin moieties (e.g., coumarin 39, coumarin 47 or Biosearch Blue). In some embodiments, the terminal moieties are linked (either directly or indirectly) to the most 3' or the most 5' nucleotide of the first or second nucleic acid strand. In some embodiments, the terminal moieties are linked (either directly or indirectly) to one of the 2, 3, 4, or 5 most 3' or most 5' nucleotides of the first or second nucleic acid strand. In some embodiments, the second mispriming prevention reagent comprises at least two non-identical 5' or 3' terminal moieties. In some embodiments, the at least two non-identical moieties are selected from dabcyl moieties, Black Hole Quencher moieties and coumarin moieties. In some embodiments, the at least two non-identical moieties comprise a dabcyl moiety and a coumarin moiety (e.g., coumarin 39, coumarin 47 and Biosearch Blue). In some embodiments, one of the non-identical moieties is located at the 5' terminus of the first nucleic acid strand and one of the non-identical moieties is located at the 3' terminus of the second nucleic acid strand. In some embodiments, one of the non-identical moieties is located at the 3' terminus of the first nucleic acid strand and one of the non-identical moieties is located at the 5' terminus of the second nucleic acid strand. In some embodiments, the non-identical terminal moieties are linked (either directly or indirectly) to the most 3' or the most 5' nucleotide of the first or second nucleic acid strand. In some embodiments, the non-identical terminal moieties are linked (either directly or indirectly) to one of the 2, 3, 4, or 5 most 3' or most 5' nucleotides of the first or second nucleic acid strand.

Visualizing Certain Mispriming Prevention Reagents

In some embodiments, the mispriming prevention reagent comprises a quencher moiety (e.g., a dabcyl moiety or Black Hole Quencher moiety, such as a Black Hole Quencher 2 moiety). In a closed-tube system containing double-stranded DNA that is longer than the stem of the reagent and using SYBR Green concentrations typically used in amplification reactions, the majority of SYBR Green molecules are intercalated into the double-stranded DNA. Consequently, the remaining dye bound to the double-stranded stem does not exceed the capacity of a covalently linked quencher moiety (if present) to quench the light emitted by the SYBR Green intercalated into the stem of the reagent. In this case, the total fluorescence of a closed-tube system decreases because only a fraction of the total SBR is available for binding to the longer double-stranded DNA, with the remainder being quenched by the reagent. In contrast, in a closed-tube system containing no double-stranded DNA other than the stem of the reagent, the fluorescence of SYBR Green intercalated into the stem exceeds the capacity of the covalently linked quencher moiety to quench the light emitted by the intercalated dye. In this case, the total fluorescence of the closed-tube system increases despite the presence of the quencher moiety. In either case, the decreased or increased fluorescence of the system occurs in a temperature-dependent quantitative manner, meaning that it is only observed over the range of temperatures in which the double-stranded stem is present and its intensity is in proportion to the absolute number of closed-hairpin molecules present at a given temperature. These increases or decreases in system fluorescence are most readily observed by calculating the negative first derivative (rate of change) of the fluorescence of the system at to the emission spectrum of SYBR Green, as a function of temperature.

First derivative temperature-dependent, quantitative increases or decreases in the SYBR Green fluorescence of a closed-tube system are plotted as −dF/dT on the Y-axis. These values change due to the presence of the reagent in the closed (hairpin) configuration and these changes in the first derivative are informative in several circumstances, including:

1) In no-template-control (NTC) amplification reactions the fluorescent signal due to the presence of the closed configuration of the reagent appears to increase, i.e. form a small hill, when plotted with −dF/dT on the Y-axis. This positive signal provides an empirical measure of the melting temperature, Tm, of the reagent in this closed-tube reaction and the temperature dependent shape of the signal provides a measure of the percentage of reagent molecules that are closed-hairpins at a given temperature. This information is useful in combination with specific thermal features of the system, including: a) the temperature(s) and time(s) at which the reaction is incubated prior to the first melting cycle of the amplification reaction; b) the primer annealing and extension temperatures used in the majority of thermal cycles; c) the temperature(s) of 1-10 unusual thermal cycles introduced at any cycle into the overall amplification reaction to achieve particular features of product amplification or detection. In addition, the percent hairpin molecules can be converted to the absolute concentration of hairpin molecules, in nanomolar, nM, when the total number of molecules added to the closed-tube reaction is known. This information, in turn, can be calculated as the nM per units of DNA polymerase present in the close-tube reaction.

2) The positive signal of the reagent in an NTC sample is extremely sensitive to amplification of even a small amount of non-intended product, including primer dimer. The positive (hill) signal disappears when even a low level of such a product is detected.

3) In reactions which amplify one or more double-stranded DNA products, the −dF/dT value of the SYBR Green bound to the stem of the reagent appears as a valley when plotted against increasing temperature. This is because the quencher moieties on the 5' and 3' ends of the hairpin quench the SYBR Green fluorescence that would otherwise emanate from the dye bound to an unmodified closed stem of a hairpin. As the temperature is increased the hairpin gradually opens and the bound SYBR Green gradually is released and rebinds to the longer double-stranded DNA product. This valley provides an empirical measure of the melting temperature, Tm, of the stem of the reagent in this closed-tube reaction. Fifty percent of reagent molecules are in the closed-hairpin conformation and 50% of the reagent molecules are in the open conformation at the lowest point in the valley observed on the plot of −dt/dT vs temperature. The percentage of molecules in the closed or open conformation can be judge for each temperature over the span of the valley. This information is useful in combination with specific thermal features of the system, including: a) the temperature(s) and time(s) at which the reaction is incubated prior to the first melting cycle of the amplification reaction; b) the primer annealing and extension temperatures used in the majority of thermal cycles; c) the temperature(s) of 1-10 unusual thermal cycles introduced at any cycle into the overall amplification reaction to achieve particular features of product amplification or detection; d) the length and composition of the loop of the hairpin. In addition, the percent hairpin molecules can be converted to the absolute concentration of hairpin molecules, in nanomolar, nM, when the number of molecules added to the closed-tube reaction is known. This information, in turn, can be calculated as the nM per units of DNA polymerase present in the close-tube reaction.

Use of Exemplary Mispriming Prevention Reagents

In some aspects, provided herein are methods of inhibiting mispriming during performance of an amplification reaction and/or a sequencing reaction using a mispriming prevention reagent described herein.

In some aspects, provided herein is a method of creating an amplification product (i.e., an amplicon) comprising a target nucleic acid sequence or complement thereof. In some embodiments, the method includes incubating a reaction mixture described herein under conditions such that a primer-based nucleic acid amplification reaction is performed (e.g., a PCR reaction, such as a LATE-PCR reaction, a LEL-PCR reaction and/or a RT-PCR reaction). In some embodiments, the method further comprises forming the reaction mixture. In some embodiments, the method further comprises detecting the formation of the amplification product.

In some aspects, provided herein is a method of sequencing a target nucleic acid. In some embodiments, the method includes incubating a reaction mixture described herein under conditions such that a sequencing reaction is performed. Nucleic acid sequencing reactions include, but are not limited to, chain termination sequencing, sequencing by ligation, sequencing by synthesis, pyrosequencing, ion semiconductor sequencing, single-molecule real-time sequencing, 454 sequencing, and/or Dilute-'N'-Go sequencing. In some embodiments, the method further comprises forming the reaction mixture.

In some aspects, provided herein is a method of creating cDNA. In some embodiments, the method includes incubating a reaction mixture described herein (e.g., comprising a reverse transcriptase) under conditions such that mRNA in the reaction mixture is reverse transcribed to cDNA. In some embodiments, the method further comprises forming the reaction mixture. In some embodiments, the method further comprises performing an amplification reaction (e.g., an amplification reaction described herein) on the cDNA.

In some embodiments, the method comprises forming a reaction mixture comprising a mispriming prevention reagent described herein (e.g., a reaction mixture described herein above). In some embodiments, the reaction mixture comprises a target nucleic acid molecule (e.g., a target nucleic acid molecule comprising a target nucleic acid sequence). In some embodiments, the reaction mixture comprises a first nucleic acid primer that hybridizes to a 3' region of the target nucleic acid sequence with a first primer melting temperature. In some embodiments, the reaction mixture comprises a second nucleic acid primer that hybridizes to a 3' region of the complement of the target nucleic acid sequence with a second primer melting temperature. In some embodiments, the reaction mixture comprises a thermostable DNA polymerase (e.g., Taq DNA polymerase, Tfi DNA polymerase, Pfu DNA polymerase, Bst DNA polymerase, Vent$_R$ DNA polymerase Deep Vent$_R$ DNA polymerase, KlearKall polymerase from LGC Biosearch, and Taq polymerase from Hain Lifescience). In some embodiments, the reaction mixture comprises dNTPs (e.g., dATP, dCTP, dGTP, dTTP, and/or dUTP). In some embodiments, the reaction mixture comprises a reverse transcriptase. In some embodiments, the first primer is present in the reaction mixture at a concentration that is at least 2-fold higher, at least 3-fold higher, at least 4-fold higher or at least 5 fold higher, than the concentration of the second primer. In some embodiments, the second primer is present in the reaction mixture at a concentration that is at least 2-fold higher, at least 3-fold higher, at least 4-fold higher or at least 5 fold higher, than the concentration of the first primer. In some embodiments, the reaction mixture further comprises a second mispriming prevention reagent (e.g., a multi-stranded mispriming prevention reagent described herein). In some embodiments, the mispriming prevention reagent is combined with the thermostable DNA polymerase before the thermostable DNA polymerase or mispriming prevention reagent is combined with the primers. In some embodiments, the mispriming prevention reagent is diluted in a Tris buffered solution.

In some embodiments of the method described herein, the reaction mixture further comprises a detection reagent for detecting the formation of the amplification product. In some embodiments, the detection reagent comprises a dsDNA fluorescent dye (e.g., SYBR Green, PicoGreen). In some embodiments, the detection reagent comprises a detectably labeled probe (e.g., a molecular beacon, a Taq-Man probe, a scorpion probe). In some embodiments, the detection reagent comprises a Lights-On probe and a Lights-Off probe. In some embodiments, the detection reagent comprises a Lights-Off Only probe and a dsDNA fluorescent dye.

In some embodiments, the method includes incubating the reaction mixture under conditions such that the first primer or second primer is extended by the thermostable DNA polymerase to create an amplification product comprising the target nucleic acid sequence or complement thereof. In some embodiments, the method includes incubating the reaction mixture at a denaturation temperature of at least 90° C., incubating the reaction mixture at an annealing temperature that is not significantly greater than the first primer melting temperature, and incubating the reaction mixture at an extension temperature at which the thermostable DNA polymerase is active. In some embodiments, the annealing temperature is no greater than the lesser of the first primer melting temperature and the second primer melting temperature. In some embodiments, the annealing temperature and the extension temperature is the same temperature. In some embodiments, the steps of the incubation process are repeated (e.g., repeated at least 5 times, 10 times, 15 times, 20 times, 25 times or 30 times).

In certain embodiments, the method provided herein comprises the step of detecting the formation of the amplification product. In some embodiments, the step of detection of the amplification product occurs simultaneously with formation of the amplification product (i.e. "real-time" detection). In some embodiments, detection of the amplification product occurs after amplification is complete. In some embodiments, the amplification step and the detection step occur in a single reaction vessel. In some embodiments, the reaction vessel is sealed prior to the amplification step and remains sealed during detection step. In some embodiments, the method includes forming a reaction mixture described herein in a reaction vessel, sealing the reaction vessel, performing an amplification reaction such that an amplification product is formed in the reaction vessel, and detecting the amplification product in the reaction vessel. In some embodiments, the detection of the amplification product occurs outside of the tube in which the amplification reaction is performed.

In certain embodiments, the mispriming prevention reagent reduces or prevents Type 1 and/or Type 2 mispriming. Type 1 mispriming occurs during preparation of reaction mixtures or execution of other enzymatic manipulations (e.g., reverse transcription in the case of one-step PCR) prior to the start of amplification. Type 2 mispriming occurs during amplification if cycle temperatures include any temperature significantly below the primer annealing temperature, as in asymmetric PCR amplifications (such as LATE-PCR), where the temperature may be dropped during amplification to allow binding of probes with melting temperatures below the annealing temperature, or as in amplification reactions that are stopped, brought to room temperature, and then resumed at a later for additional number of thermal cycles. Type 2 mispriming can also occur in LEL-PCR, where the temperature may be dropped for 1-5 cycles following the initial phase of linear amplification in order to allow the reverse (excess primer) to hybridize to the Limiting Primer single strands.

In certain embodiments, the reagents described here are used to prevent or reduce Type 1 and Type 2 mispriming in PCR amplification reactions. In some embodiments, the reagent does not diminish the efficiency of DNA replication during the majority of thermal cycles, while also making it possible to deliberately diminished or inhibit DNA replication during special cycles required for aspects of amplification or detection of one or more intended targets.

In some embodiments, the composition and use of the mispriming prevention reagents described herein can be optimized by adjusting the following factors in the following ways:

1) The functional Tm of the hairpin can be increased or decreased by adjusting the length and base-pair composition of the stem, including the use of non-natural nucleotides. The functional Tm of the hairpin can also be increased or decreased by altering the number of cytosine nucleotides in the loop. The functional Tm of the hairpin can also be adjusted by altering the chemical composition of the 3' and 5' moieties. As explained above, the functional Tm of a hairpin containing at least one fluorphore-quenching moiety can be determined and its temperature-dependent formation can be observed in the presence of SYBR Green by analysis of the first derivative of its signal. In terms of its Tm, the reagent is most effective when the hairpin is essentially 100% in hairpin conformation at the lowest temperature used prior to the start of the reaction, typically on ice or at room temperature and the hairpin is <5% in hairpin conformation at the temperature used for primer annealing in the majority of thermal cycles.

2) The optimal concentration of the reagent used in an amplification reaction can be adjusted in relation to the amount of enzyme used in the reaction by taking the following variables into account: a) The affinity of the reagent in its closed hairpin configuration for the enzyme under reaction conditions. This affinity can be determined empirically by comparing the capacities of different variants of the reagent to suppress Type I and/or Type II mispriming when added to a set of reactions at lower and lower concentrations. Reagents having the highest affinity for the enzyme require the lowest concentration to achieve suppression of Type I and/or Type II mispriming. Results discussed below describe the relative affinities of various reagents in these terms. b) The optimal concentration of the reagent to use also depends on the thermal steps of the reaction. For instance, if the reaction is set up on ice, or at room temperature (about 25° C.) before the start of the reaction, approximately 650 nM of fully double-stranded hairpin reagent is needed per 1.5 units of enzyme in a 25 µl reaction. However, if the thermal profile of the reaction calls for an additional temperature pause prior the first melting step, only a fraction of the same reagent is still in the double-strand hairpin conformation and the concentration of the reagent has to be increased to achieve the same ratio of double-stranded hairpin molecules to the same 1.5 units of enzyme in the same 25 µl reaction.

3) Because mispriming in a reaction depends on the rate at which un-intended events take place, increasing the length of time spent at any one or more steps of an amplification reaction may necessitate increasing the concentration of a reagent relative to the concentration of the enzyme.

4) Because the reagent is active in suppressing Type I and Type 2 mispriming when it is bound to the enzyme, in some embodiments it is mixed with the enzyme prior to mixing the enzyme with the primers, or is present in the reaction mixture prior to addition of the enzyme and is not added to a reaction mixture after the enzyme is added to the mixture, regardless of whether or not a template strand for those primers is present in the final reaction mixture. Moreover, because the reagent is only active in its double-stranded hairpin conformation, it has to be prepared under conditions in which it adopts this conformation before it is mixed with the enzyme, or at least before the enzyme-reagent mixture is mixed with one or more primers used for amplification, regardless of whether a template strand for those primers is present in the final reaction mixture.

EXAMPLES

Example 1

Figure 2:
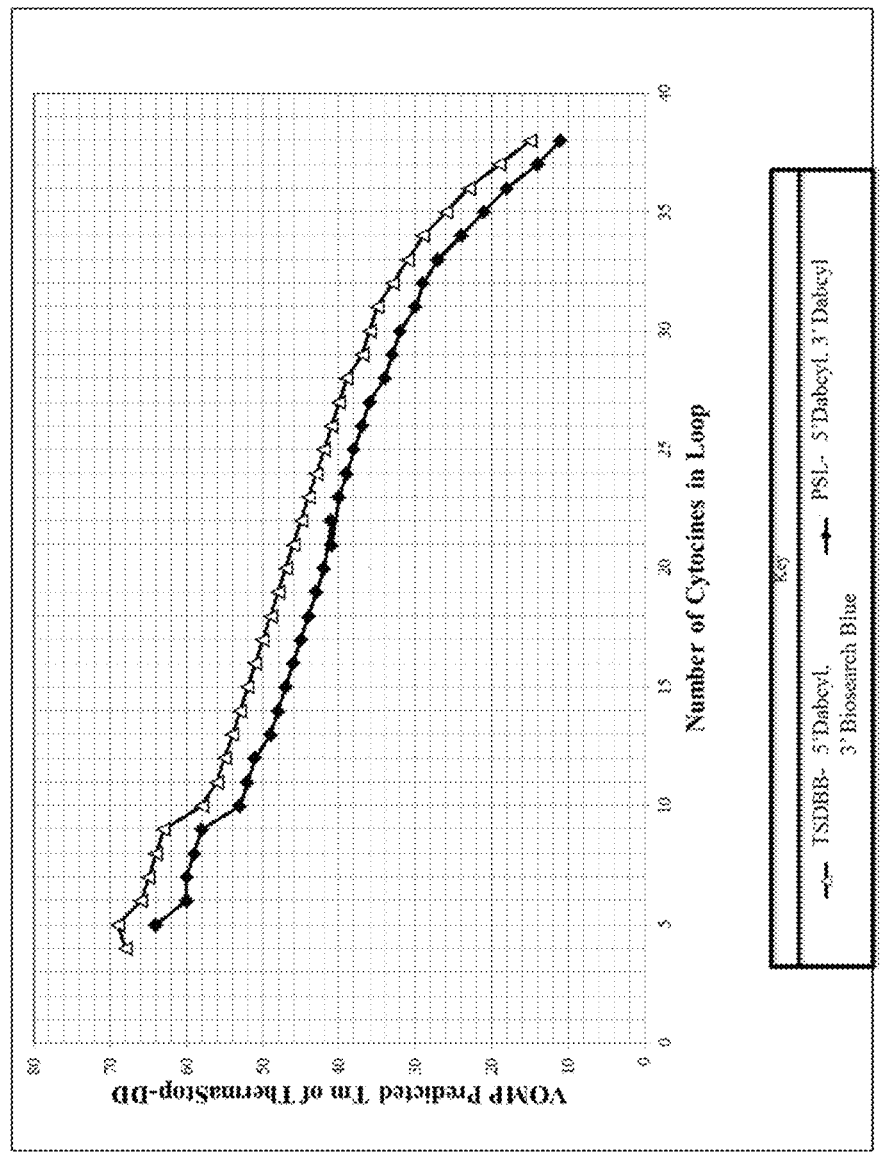
FIG. 2 shows the predicted effect of the length of the loop sequence on the stem melting temperature for exemplary reagents (PSL and TSDBB) described herein.
Figure 3:
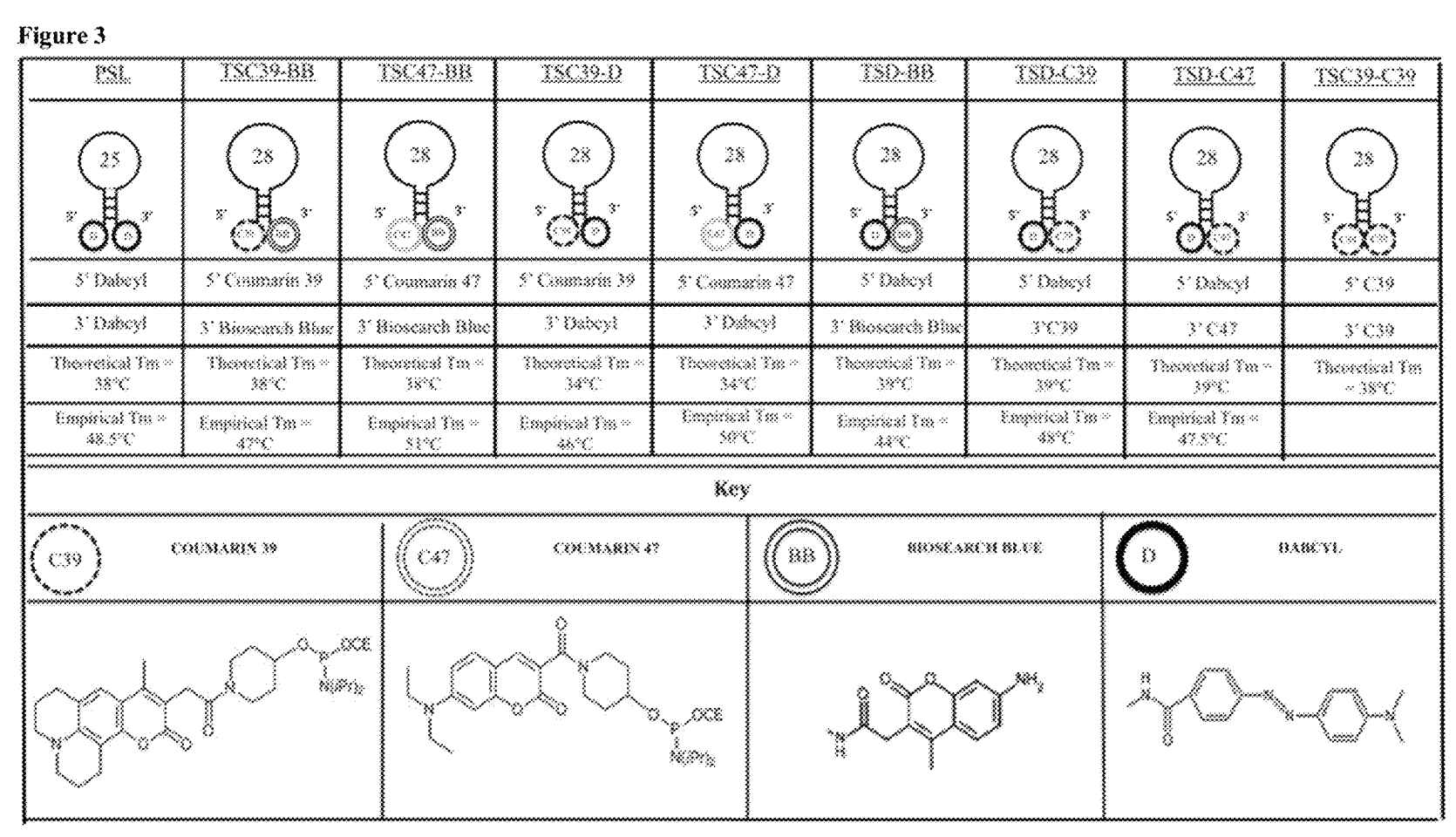

The Effect of Hairpin Loop Length and Mismatched Terminal Moieties on Mispriming Prevention Reagent Melting Temperature As the length of a cytosine loop is increased, in silico melting temperature analysis (Visual OMP, version 7.5.0.0, DNA Software Inc., Ann Arbor, Mich.) predicts that the melting temperature of the hairpin stem will decrease. However, as seen in FIG. 2, the relationship of loop length and Tm is not strictly linear. These data are presented for two structure, PSL is an exemplary mispriming prevention reagents that has dabcyl moieties on both the 5' and 3' ends, and TSDBB which is an exemplary mispriming prevention reagent described herein, having a 5' dabcyl moiety and a 3' Biosearch Blue moiety. As seen in FIG. 2, the Tm of each of the possible PSL variants is predicted to be a few degrees higher than the Tm of TSDBB molecule of equivalent loop length. Because of this, in certain embodiments, reagents with matched terminal moieties are designed with 25 cytosines in the loop while reagents with mismatched moieties are designed with 28 cytosines in the loop (FIG. 3).

The presence of at least one dabcyl moiety (a quencher) on at least one reagent terminus allows the measurement of the empirical Tm of a hairpin when SYBR Green, a fluorescent dsDNA binding dye, is added to the reaction mixtures. FIG. 3 shows that the empirical Tm of various mispriming prevention reagents described herein. The higher the Tm, the more stable the stem structure.

Example 2

Prevention of Mispriming by Exemplary Reagents Described Herein

Figure 4:
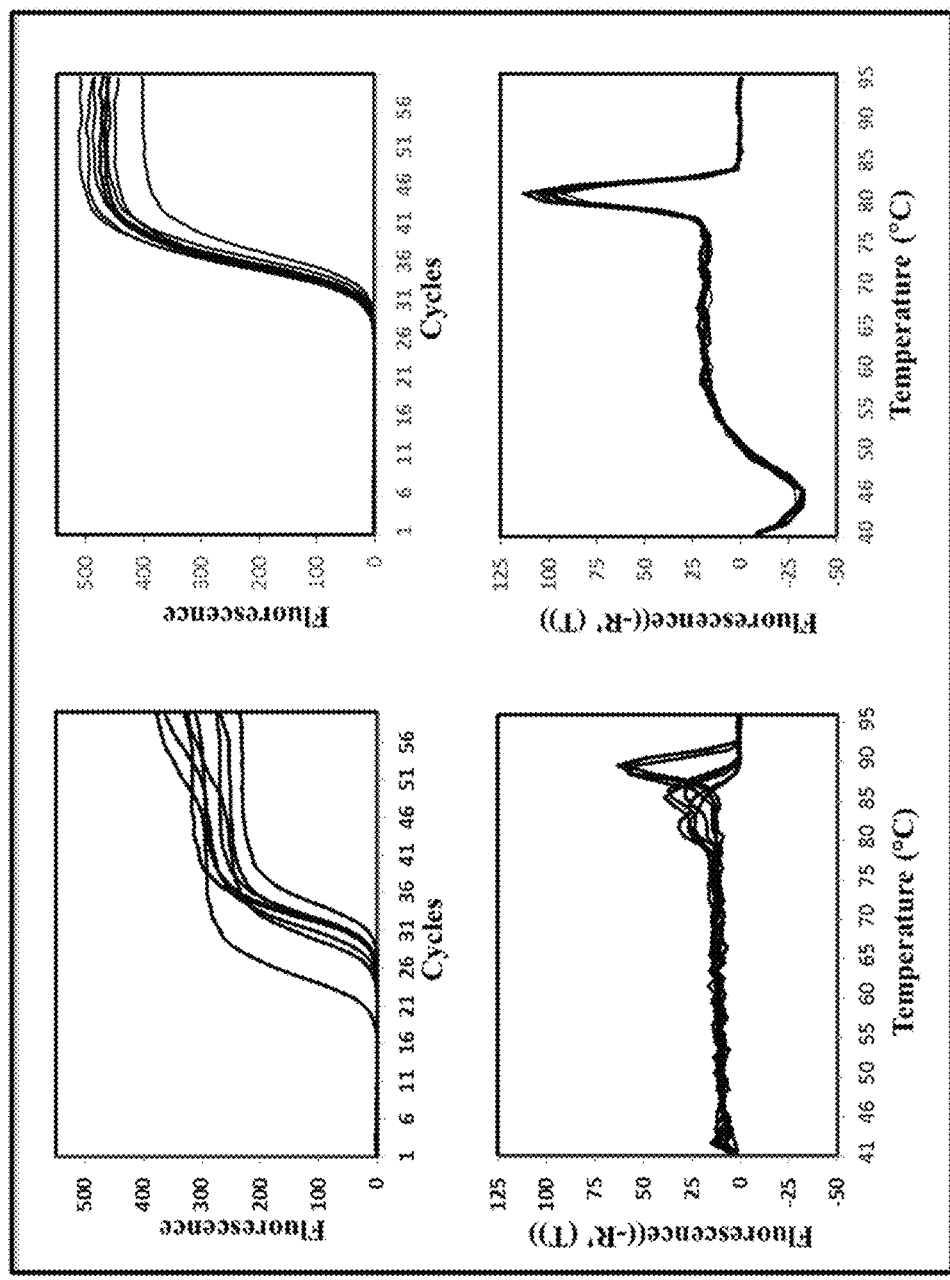
FIG. 4 shows mispriming suppression by an exemplary mispriming prevention reagent described herein (right panels) compared to a no-reagent control (left panels) in PCR assays.

In certain embodiments, the mispriming prevention reagents described herein have the capacity to suppress one or more aspects of mispriming, and thereby enhance the amplification of one or more intended products in a PCR amplification. FIG. 4 illustrates the capacity for TSDBB, an exemplary mispriming prevention reagent (FIG. 3), to suppress mispriming at a concentration of 650 nM/reaction in comparison to a no-reagent control. Both sets of reactions contain a DNA target. The results demonstrate that the no-reagent samples display chaotic amplification kinetics (top left panel) and contain a variety of amplified products having different Tm's (bottom left panel), most of which are too high to be the intended product. In contrast, mispriming is suppressed in all reactions containing TSDBB with the result being that the kinetics of amplification are reproducible (top right panel) and melt curve analysis reveals that there a single amplicon peak having the expected Tm for all samples (bottom right panel).

Figure 5:
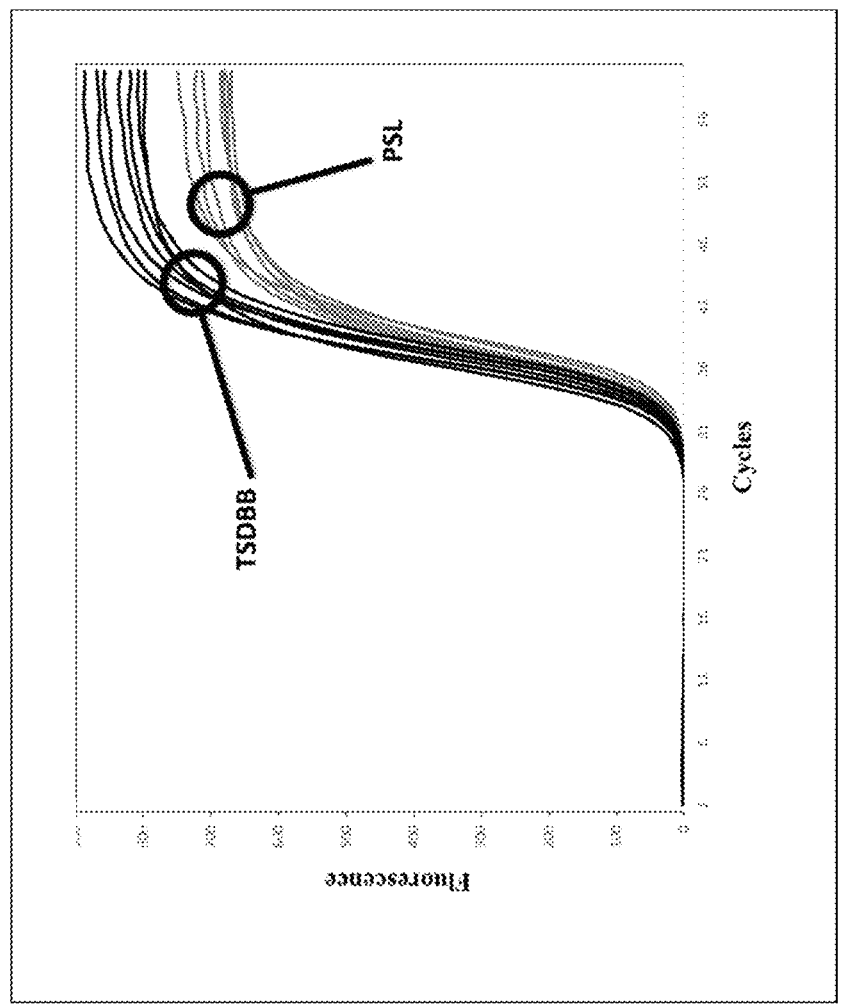
FIG. 5 shows the performance of 650 nM PrimeSafe reagent (PSL) versus 650 nM of TSDBB, an exemplary single-stranded mispriming prevention reagent described herein, each in a reaction containing 1.5 units of Taq polymerase.

FIG. 5 depicts a comparison of 650 nM PSL and an equivalent concentration of TSDBB. Both sets of samples display homogeneous kinetics, but the TSDBB reactions have a higher plateau value than the PSL reactions, indicating that more amplification product is formed in the TSDBB reactions. Without being bound by theory, this improved yield is likely due to the greater capacity of TSDBB compared to PSL to suppress low levels of primer-dimer formation. In other words, in the presence of TSDBB primers are not wasted in the formation of dimers.

Figure 6:
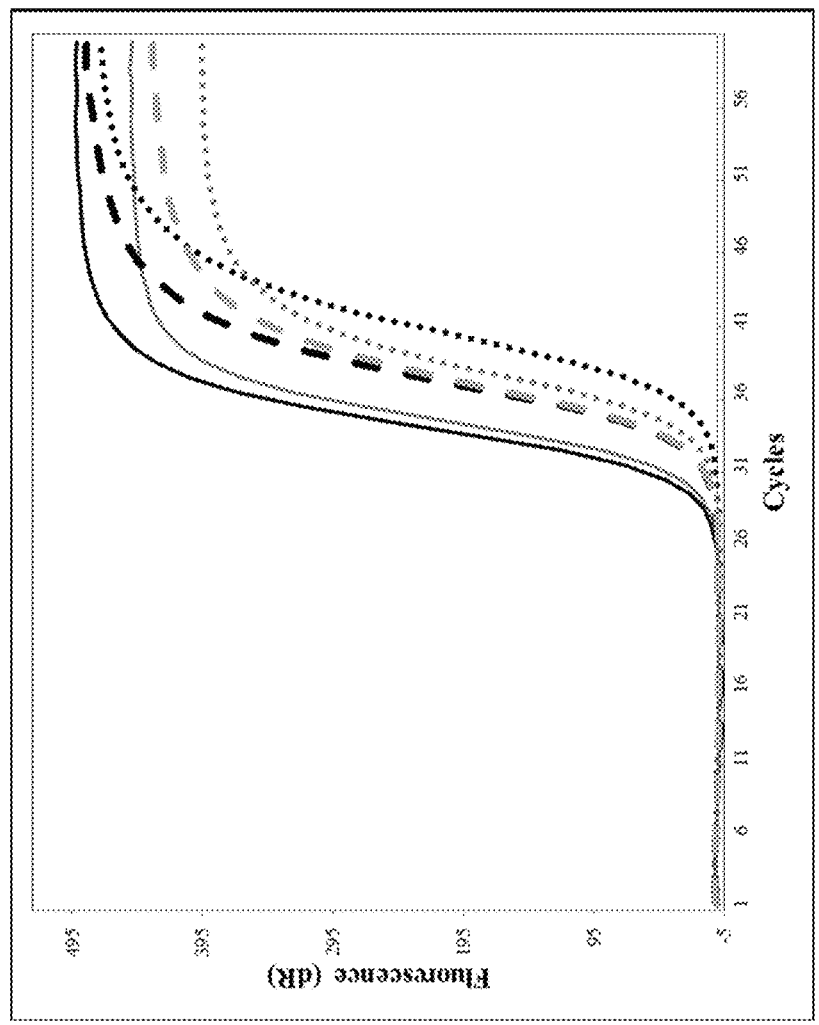
FIG. 6 shows a comparison of the yield of various amplification reactions that either contained 650 nM TSDBB per reaction (black lines) or that contained a hot-start antibody in the absence of a mispriming prevention reagent described herein (gray lines), each in a reaction containing 1.5 units of Taq polymerase. The line pattern corresponds to the amplification product formed.

FIG. 6 shows the results of three similar experiments, each with a different target amplicon, that compare the yield of reactions that either contained 650 nM TSDBB/reaction (black lines) or that contained a hot-start antibody in the absence of a mispriming prevention reagent described herein (grey lines). In each case the single line shown is an average of either replicate reactions and, in each case the reactions containing TSDBB reached a higher plateau value than the corresponding reactions containing the antibody. Each experiment is distinguished by the pattern of the line (experiment 1: solid lines, experiment 2: dashed lines, experiment 3: dotted lines). This the hot-start antibody fails to totally inhibit primer-dimer formation for each of the different pairs of primers.

Figure 7:
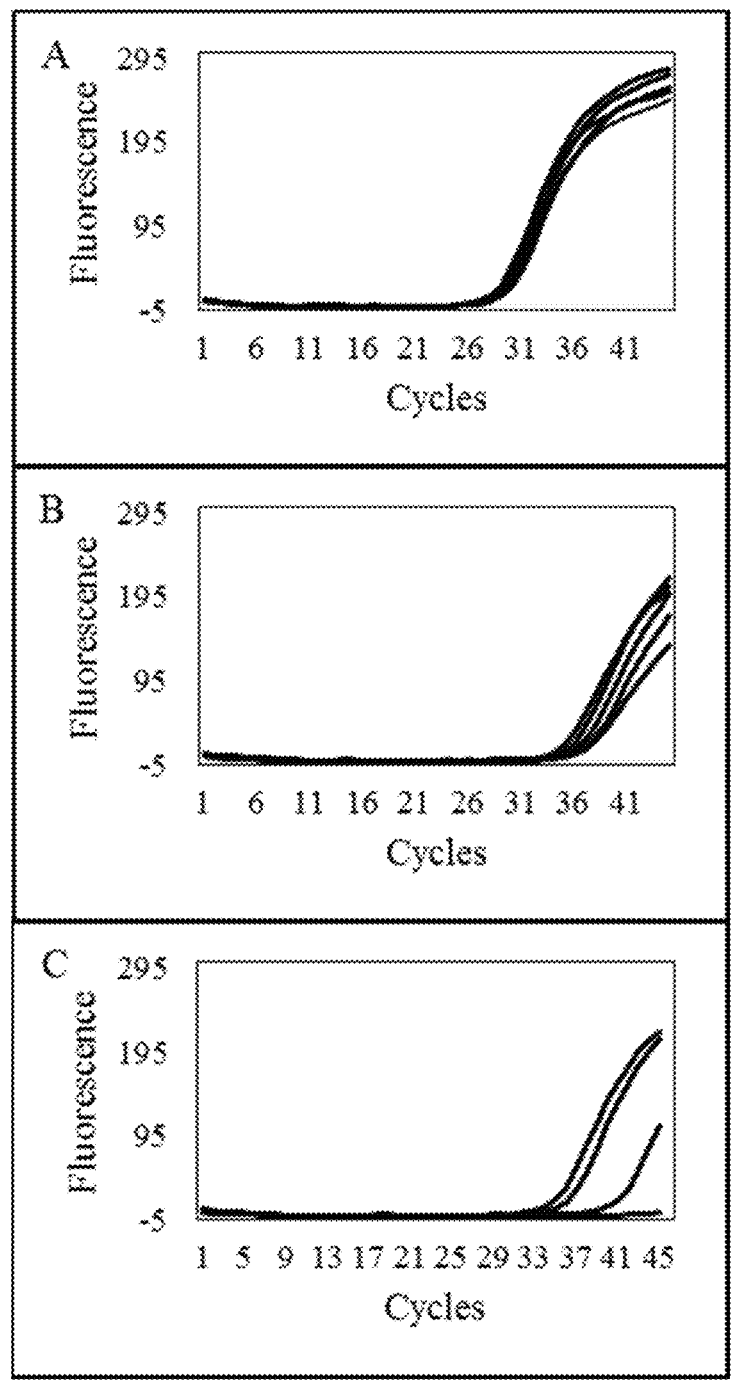
FIG. 7 shows a comparison of the yield of product formation in no template control amplification reactions that either contained (A) no hot-start at all, (B) 650 nM of a second exemplary mispriming prevention reagent described herein (TSC39BB), or (C) 650 nM TSDBB, each in a reaction containing 1.5 units of Taq polymerase.
Figure 8:
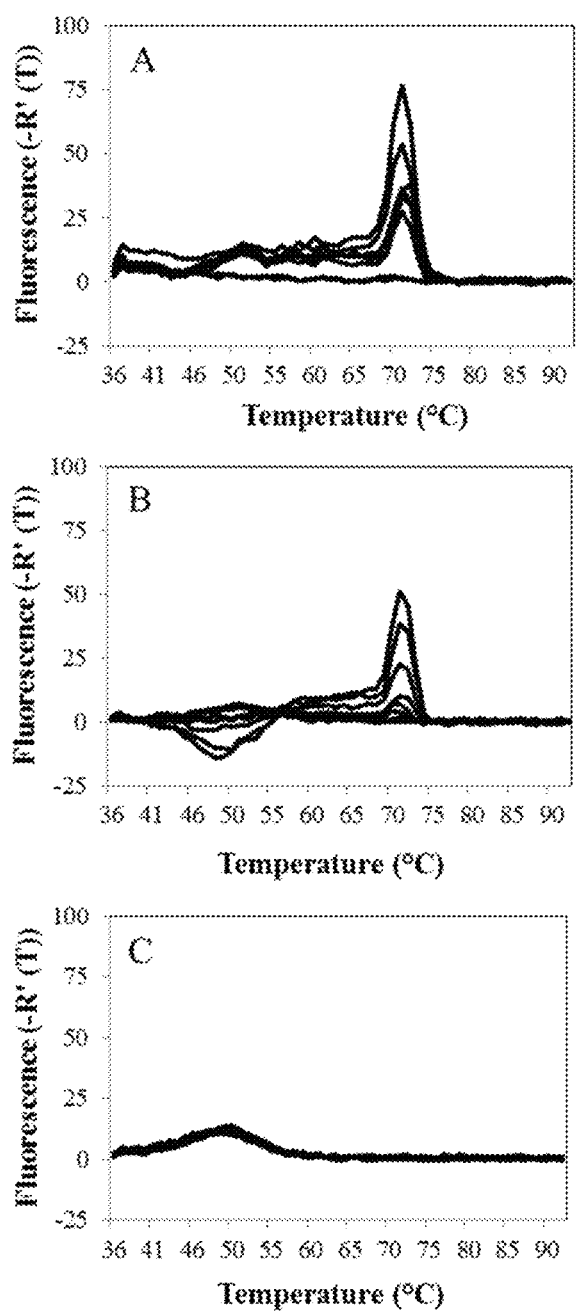
FIG. 8 shows a melt peak analysis of the products formed in no template control amplification reactions that either contained (A) no hot-start at all, (B) 650 nM PSL, or (C) 650 nM TSDBB, each in a reaction containing 1.5 units of Taq polymerase.
Figure 9:
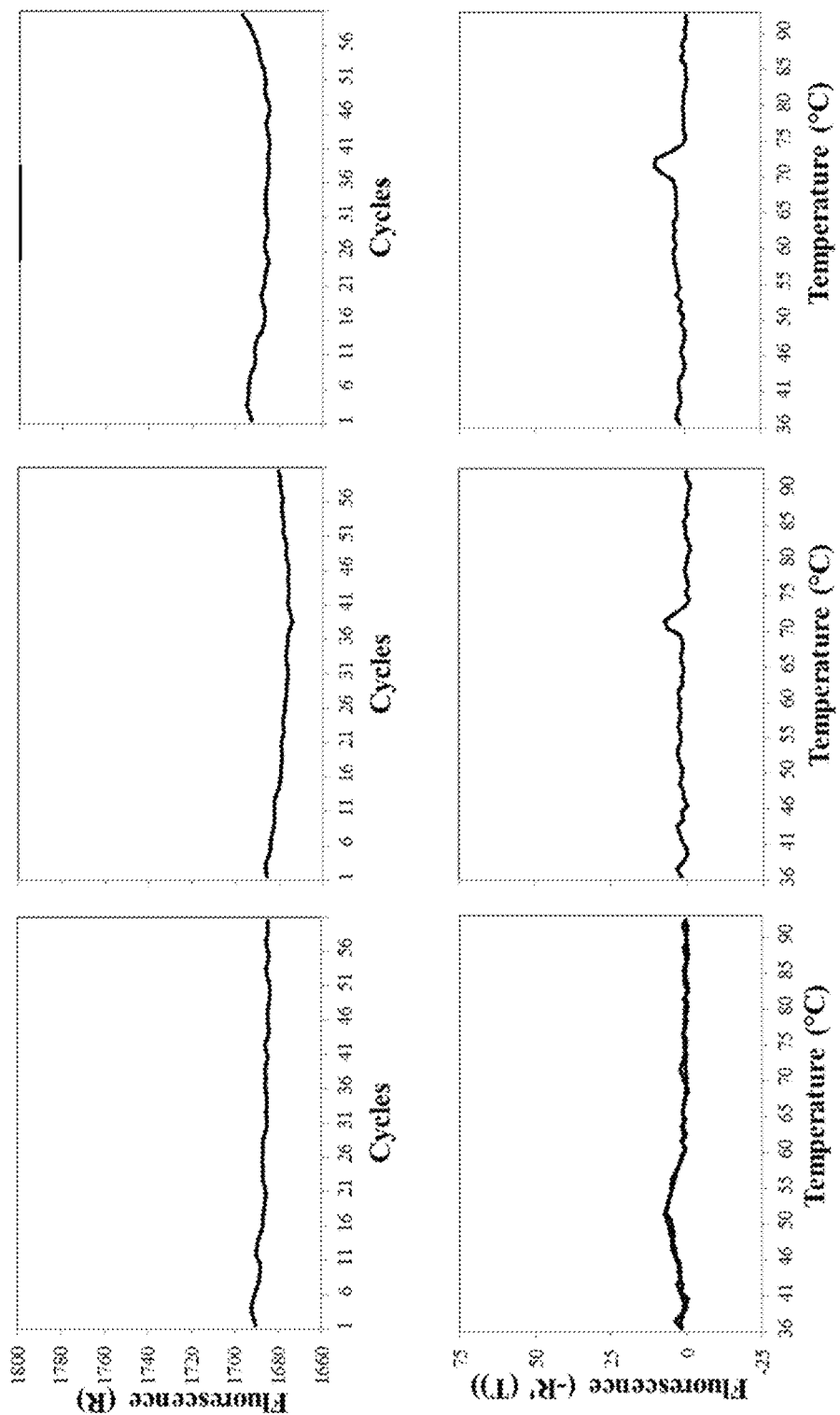
FIG. 9 shows the product accumulation (top) and melt peak analysis (bottom) of three samples analyzed in FIG. 8 panel B that had the lowest fluorescent signals.

FIGS. 7-9 provide a comparative analysis of the capacities of the mispriming prevention reagents described herein to suppress primer-dimer formation in no template control (NTC) reactions containing various pairs of primers, but no added DNA template. The three panels of FIG. 7 compare the fluorescent signals observed in reactions containing no hot-start at all (A), or 650 nM TSC39BB (B), or 650 nM TSDBB (C). In the absence of any hot-start, FIG. 7 panel A, all replicates amplified non-specific products by 32 cycles. In the presence of TSC39BB, FIG. 7 panel B, all replicates accumulated non-specific products, but only after a delay of several cycles, indicating the primer-dimer formation was delayed but not entirely suppressed. FIG. 7 panel C, shows that some of the replicates containing TSDBB did not generate any products, while others generate very low levels of products after a considerable delay. Thus both TSC39BB and TSDBB were able to suppress mispriming, although TSDBB was more effective than TSC39BB.

FIG. 8 displays the results of a similar NTC experiment, this time comparing the efficacy of no hot-start, 650 nM PSL, and 650 nM TSDBB. The results are displayed as melt peaks. Six of eight reactions containing no hot-start (FIG. 8 panel A), generated high levels of primer-dimers, and three of eight reactions containing PSL generated moderate levels of primer-dimers (FIG. 8 panel B). In contrast, none of the reactions containing TSDBB generated any primer-dimers in these eight reactions (FIG. 8 panel C). Instead, these reactions all contained a small positive melt peak at a temperature much lower than primer-dimer, due to SYBR Green binding to the stem of the mispriming prevention reagent. In the absence of any primer-dimer, the concentration of unbound SYBR Green in the closed system saturates the stem of the hairpin and exceeds the capacity of the dabcyl moiety to quench the SYBR Green fluorescence.

FIG. 9 provides a closer look at three samples analyzed in FIG. 8 panel B that had the lowest fluorescent signals. None of these samples displayed a detectable signal over background when measured as total fluorescence (top). However, when the same samples were analyzed as first derivative melt peaks (bottom) two replicates had a low temperature melt peak due to SYBR Green binding to the stem of the PSL. These results are consistent with fact that SYBR Green preferentially binds to longer double-stranded DNA molecules, in this case the primer-dimers instead of the PSL stem.

Example 3

Additional Features of Exemplary Reagents Described Herein

Figure 10:
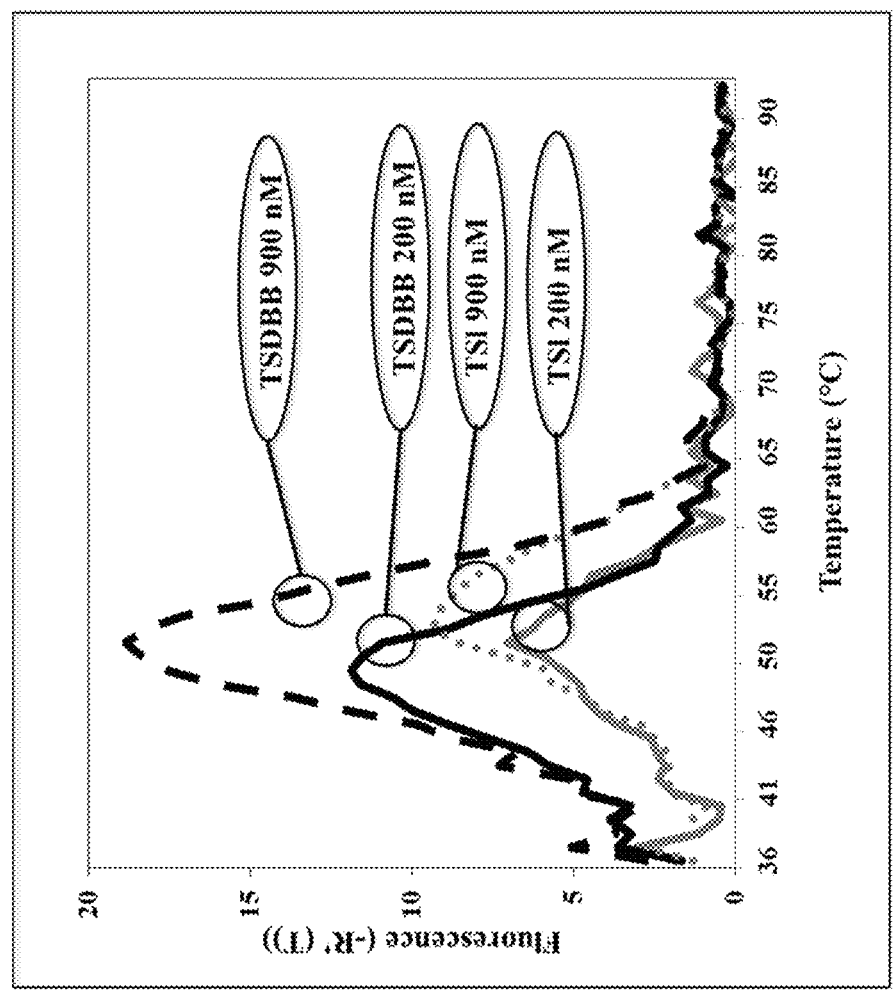
FIG. 10 shows SYBR Green melt curve analysis of non-template control samples containing either 900 nM or 200 nM of TSDBB or PSL, each in a reaction containing 1.5 units of Taq polymerase.

As described above, SYBR Green melt curve analysis of non-template control samples containing no double-stranded DNA other than the stem of the hairpin display a positive signal, the maximum of which defines the empirical Tm of the reagent in the closed-tube. As shown in FIG. 10, the amplitude of the peak correlates with the concentration of the reagent in the reaction, while the Tm of the peak shifts according to the properties of the reagent. These data also show that amplitude of the peak differs on the basis of how many quencher moieties are linked to the reagent. Thus peaks of TSDBB are higher than those of PSL, for equivalent nanomolar (nM) amounts, because the TSDBB has a single dabcyl moiety while PSL has two dabcyl moieties.

Figure 11:
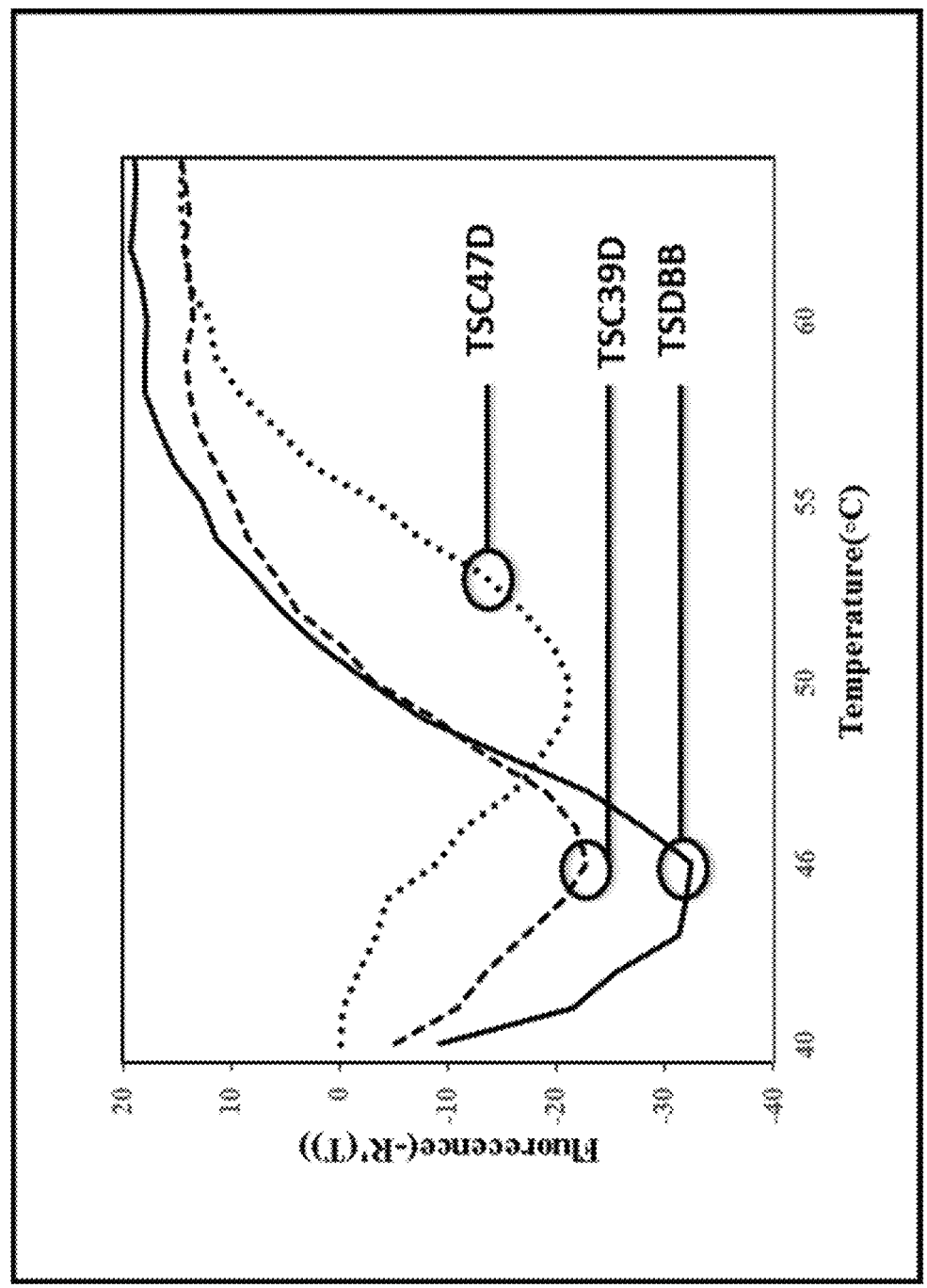
FIG. 11 shows SYBR Green melt curve analysis of amplified samples containing a double-stranded amplification product and TSDBB, TSC39D or TSC47D, each in a reaction containing 1.5 units of Taq polymerase.

As seen in FIG. 11, the presence of a double-stranded DNA amplicon of any size in the reaction converts the reagent "hill" into a reagent "valley". This occurs because the closed system no longer contains unbound SYBR Green, making it impossible to fully saturate the stem of the reagent with the dye and hence to overwhelm the quencher. The fluorescence of the dye bound to the stem is now quenched with a resulting loss in total fluorescence of the closed system. In this case the position of the valley reflects the empirical Tm of the particular reagent, and the shape of its valley reflects is particular self-hybridizing properties, for instance TSDBB has a lower Tm than the other two exemplary mispriming prevention reagent variants, and the "walls" of its valley are steeper. This indicates the TSDBB hairpin opens and closes over a narrow temperature range than the other reagents.

Figure 12:
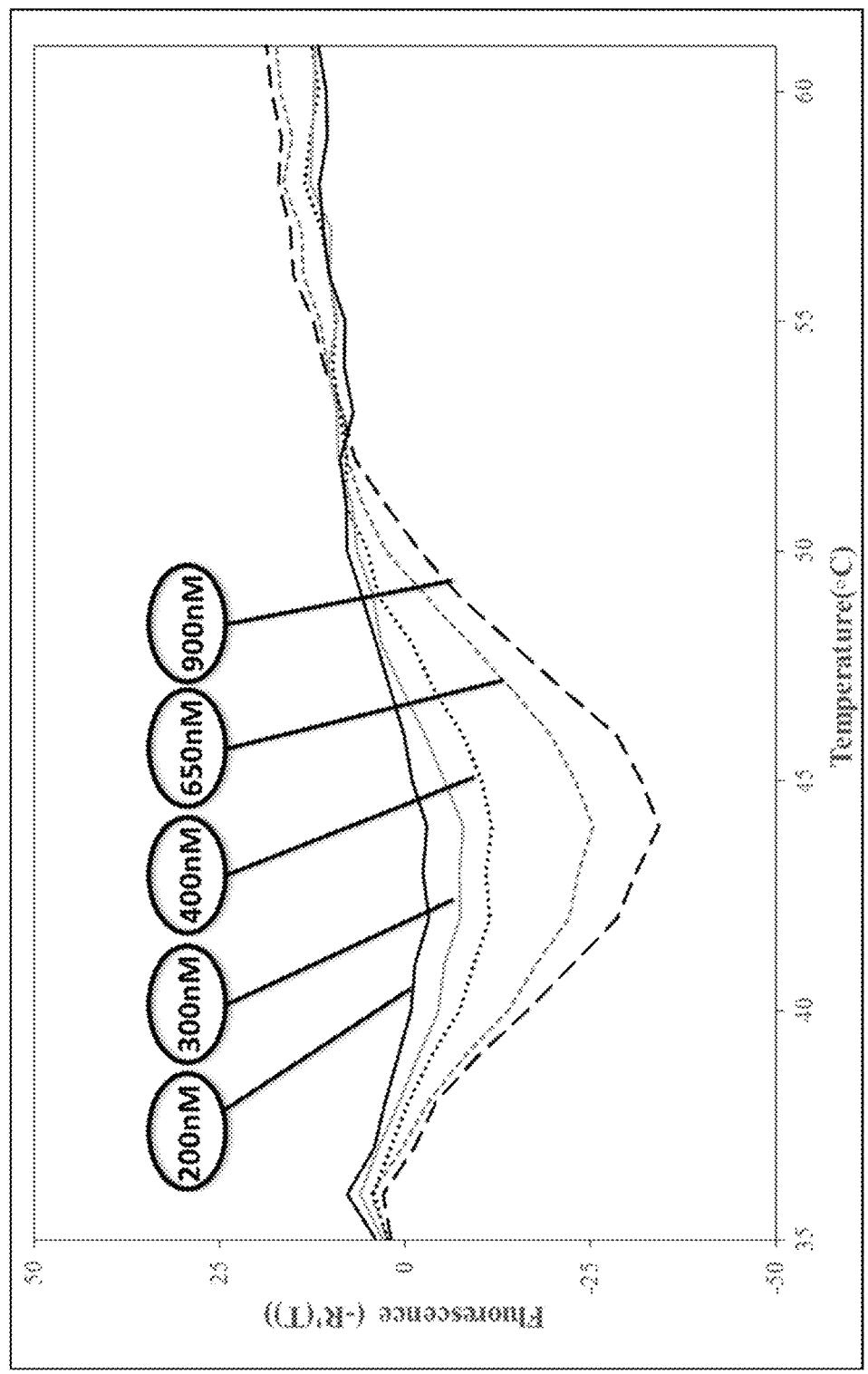
FIG. 12 shows SYBR Green melt curve analysis of amplified samples containing a double-stranded amplification product and the indicated concentrations of TSDBB, each in a reaction containing 1.5 units of Taq polymerase.
Figure 13:
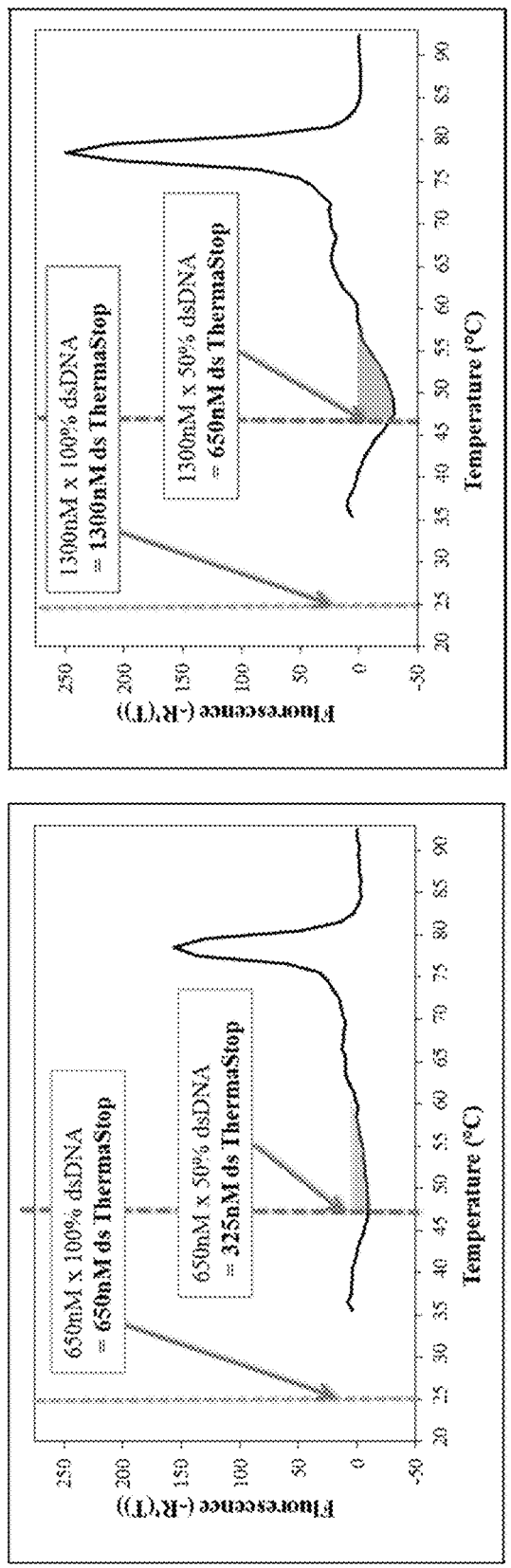
FIG. 13 shows the use of the valley generated by the mispriming prevention reagent in the presence of SYBR Green and use of this valley to determine the optimal concentration of mispriming prevention reagent, each in a reaction containing 1.5 units of Taq polymerase.

FIG. 12 demonstrates that the depth of a mispriming prevention reagent valley is proportional to the amount of the reagent added to the reaction. This is yet another useful property of embodiments of the reagent which can be used to confirm that its concentration is the same at the start and end of amplification. This valley can also be used as an amplification-independent standard against which to measure the amount of product generated in different reactions. For example, FIG. 13 depicts the use of the valley to determine the optimal concentration of reagent (650 nM vs. 1300 nM).

Figure 14:
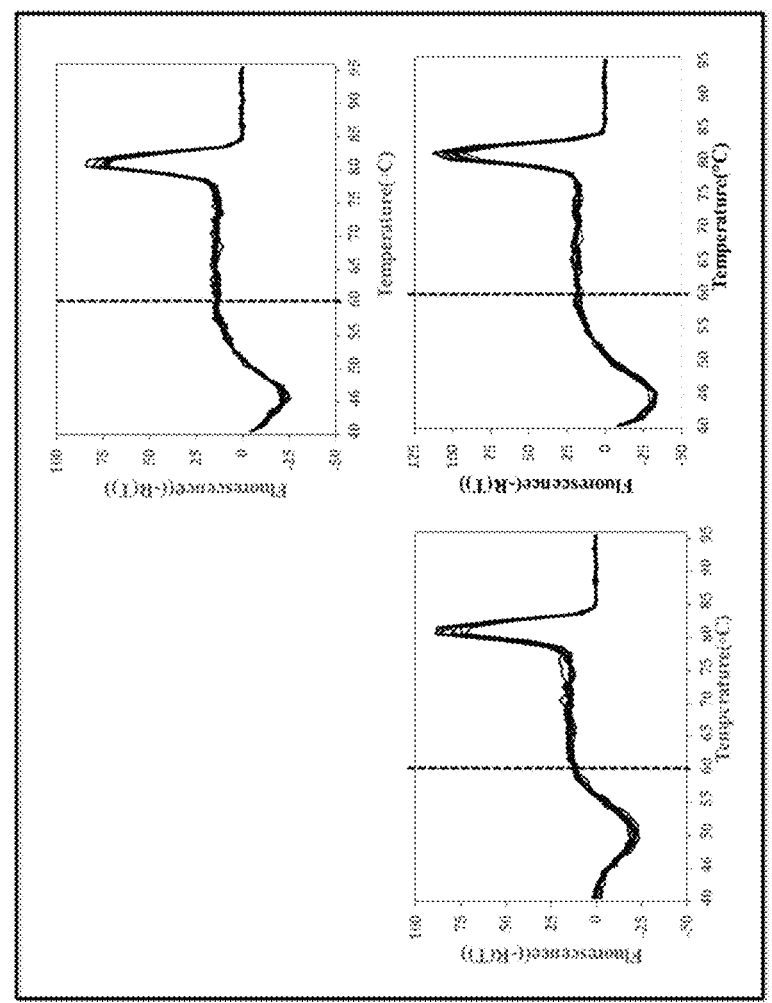
FIG. 14 shows SYBR Green melt curve analysis of samples containing double-stranded DNA and 650 nM of TSC39D (top), TSC47D (lower left) or TSDBB (lower right), each in a reaction containing 1.5 units of Taq polymerase.
Figure 15:
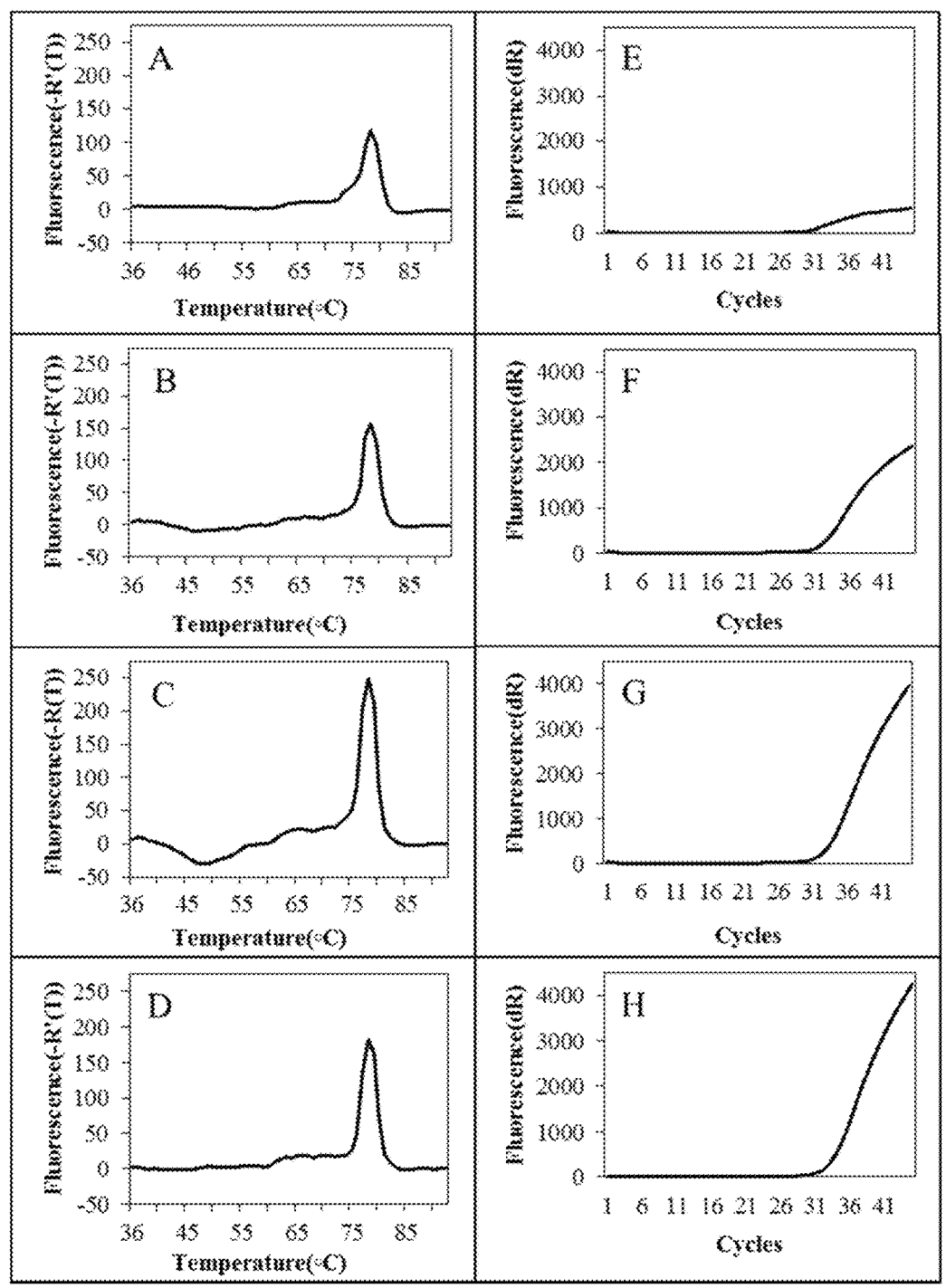
FIG. 15 shows the effect of TSDBB concentration on the suppression of Type 1 mispriming, each in a reaction containing 1.5 units of Taq polymerase.

In certain embodiments, the mispriming prevention reagents described herein are designed to melt open to at least 95% completion at the annealing temperature used for the majority of thermal cycles in a PCR amplification reaction. For instance, in FIG. 14 all three of the exemplary reagent variants were essentially fully open at 60° C., as evidenced by the highest temperature edge of the valley. This minimizes the chance that the reagent will not inhibit polymerase activity at or above the standard annealing temperature. In contrast, at a much lower temperature, for instance at 40° C. or below in FIG. 14, most or all of the exemplary reagent molecules are in the closed-hairpin conformation and the reagent is exerting the maximum possible concentration-dependent suppression of mispriming. It follows from the above insights that the percentage of functional (closed-hairpin molecules) present in a reaction is temperature-dependent and can be increased or decreased by either raising or lowering the temperature of the reaction in the range of hairpin formation, and/or can be adjusted by increasing or decreasing at concentration of reagent in the reaction. FIG. 15 presents results from an experiment in which two different concentrations of TSDBB were added to replicate NTC and plus-DNA reactions that were set up on ice (4° C.) and then incubated for 30 minutes at 47° C. before the first thermal cycle. As shown in FIG. 15 panel A 650 nM TSDBB failed to suppress primer-dimer amplification in the NTC samples. This is because only about 50% of the reagent molecules, 325 nM, were hairpins which is not enough to saturate the 1.5 units of Taq polymerase in the reaction. In contrast, FIG. 15 panel C shows that 1300 nM TSDBB was sufficient to suppress primer-dimer formation in the NTC samples, because at 47° C. the concentration of the closed hairpins was about 650 nM, the concentration of TSDBB needed for suppression of mispriming in a reaction containing 1.5 units of Taq polymerase. FIG. 15 panels B and D show that the amount of the intended amplicon produced in the reactions contain 1300 nM TSDBB was greater than that produced in the reactions containing 650 nM reagent, consistent with the fact that some of the primer was wasted when functional temperature-adjusted reagent concentration was too low.

Figure 16:
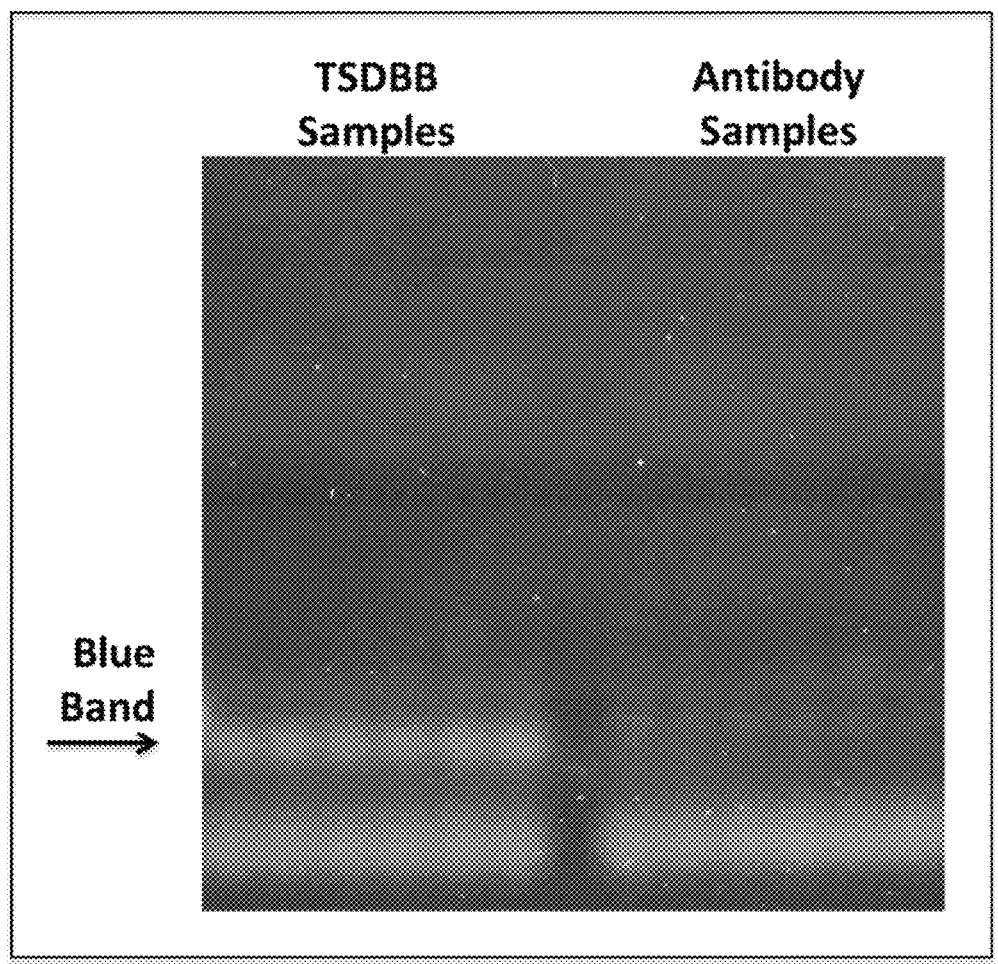
FIG. 16 shows an image under UV light of an agarose gel containing samples supplemented with either TSDBB reagent or Taq DNA polymerase antibody.

In certain embodiments, the mispriming prevention reagents described herein have a coumarin derivative, such as TSDBB labeled with Biosearch Blue, on one terminus of the stem and do not fluoresce during detection of SYBR Green because the fluorophore is not excited at the wavelengths used to excite the SYBR Green. However, TDSDBB labeled with Biosearch Blue does fluoresce blue when this variant is run on a gel that is stained and photographed with UV light (FIG. 16). The blue colored TSDBB band is convenient for determining the position of the reagent in the gel after electrophoresis and the intensity of the band gives an approximation of how much reagent is present, as well as whether the reagent is intact.

Figure 17:
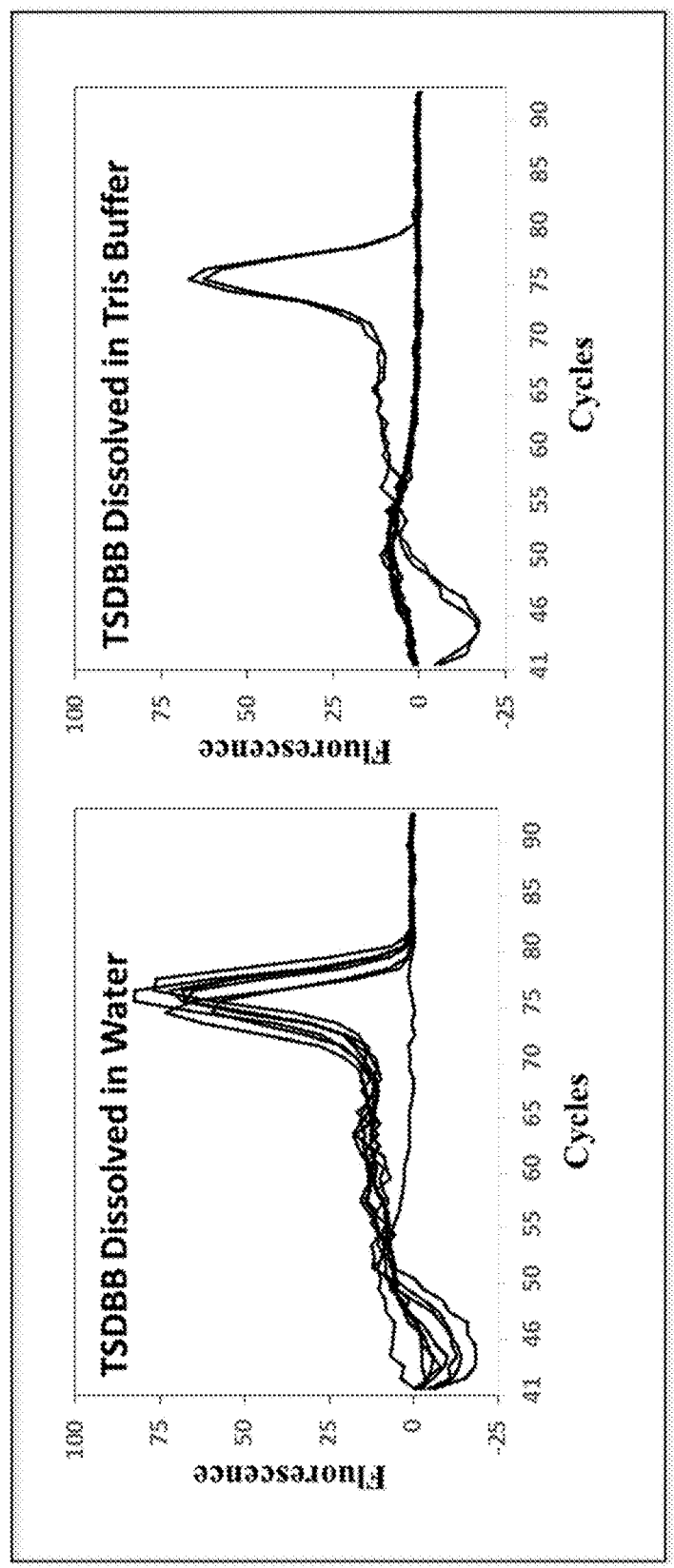
FIG. 17 shows the effect of dilution of the exemplary mispriming prevention reagents in water (left) versus Tris buffer (right).

In some embodiments, the functionality of exemplary mispriming prevention reagents described herein is affected by the composition of the liquid in which it is dissolved prior to mixing with the DNA polymerase. FIG. 17 shows that reagent that is diluted in a Tris buffered solution prior to being mixed with the enzyme results in improved mispriming prevention activity compared to reagent that is diluted in pure water pure water.

Figure 18:
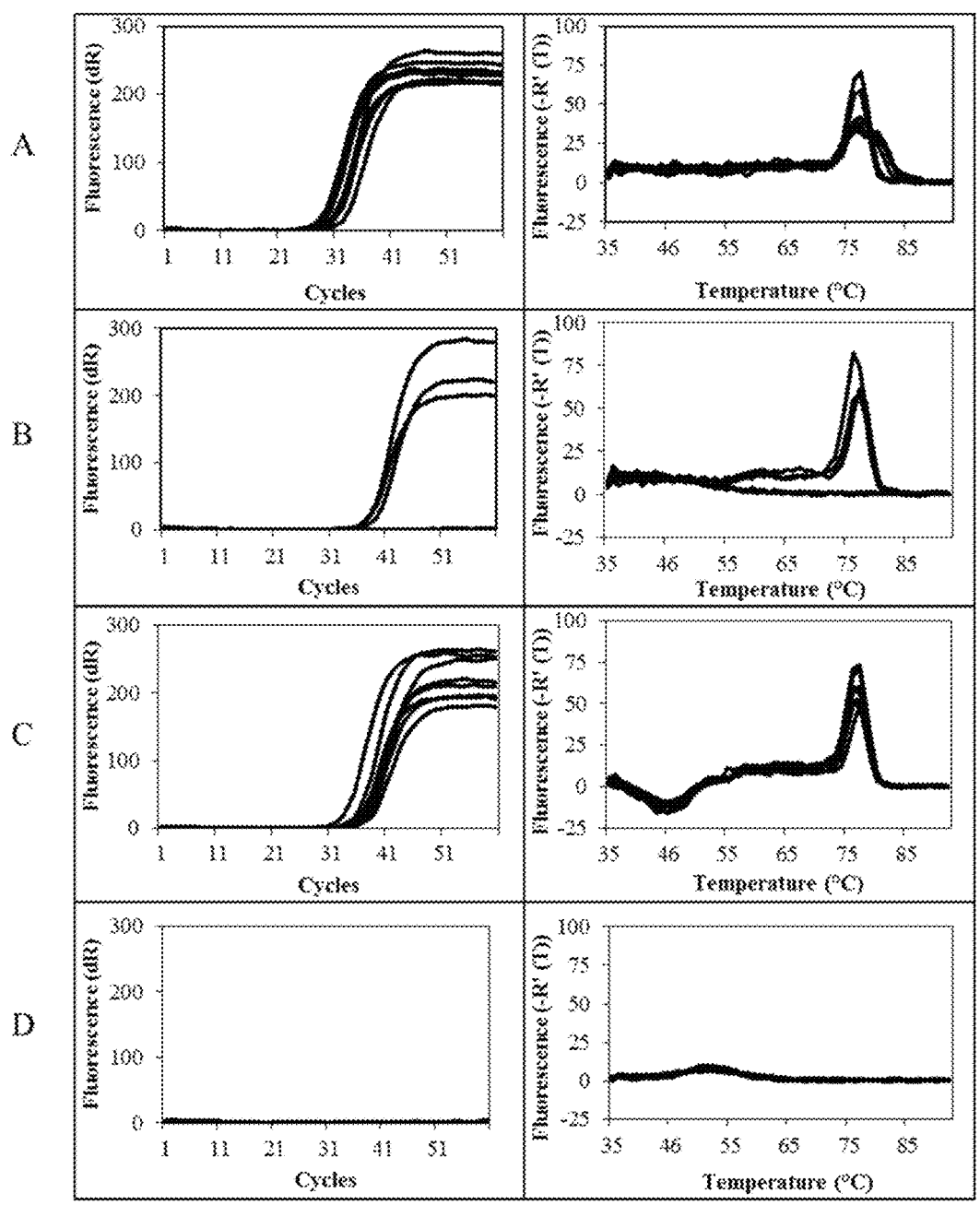
FIG. 18 shows how the order at which exemplary mispriming prevention reagents are added to an amplification reaction can affect the reagent's mispriming prevention activity in a sample in which there is no target present. (A) no hot-start reagent added to reaction solution. (B) Hot start antibody mixed with Taq before addition to reaction solution. (C) Taq added to reaction solution before TSDBB addition. (D) TSDBB mixed with Taq before addition to reaction solution, each in a reaction containing 1.5 units of Taq polymerase.
Figure 19:
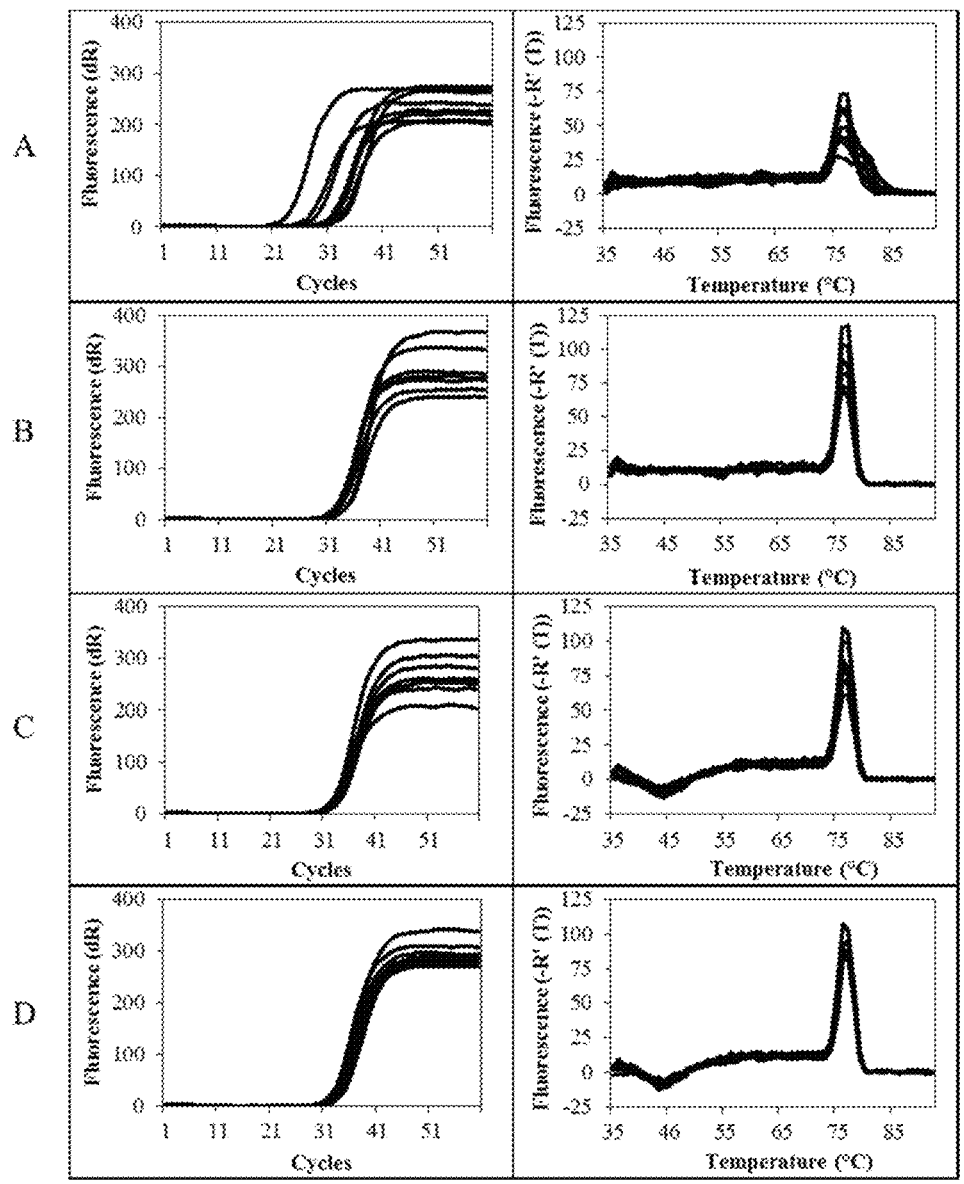
FIG. 19 shows how the order at which exemplary mispriming prevention reagents are added to an amplification reaction can affect the reagent's mispriming prevention activity in a sample in which there is target present. (A) No hot-start reagent added to reaction solution. (B) Hot start antibody mixed with Taq before addition to reaction solution. (C) Taq added to reaction solution before TSDBB addition. (D) TSDBB mixed with Taq before addition to reaction solution, each in a reaction containing 1.5 units of Taq polymerase.

In some embodiments, the functionality of exemplary mispriming prevention reagents described herein is affected by the order in which the reagent is added to a PCR assay mixture. FIGS. 18-19 show that certain reagents described herein are more effective in suppressing mispriming when mixed with the enzyme before the enzyme is added to the other components in the master mix, as compared to adding the reagent to the master mix and then adding the enzyme.

FIG. 18 compares the level of mispriming in replicate samples prepared under four conditions, all without an added DNA template (−DNA). In one of the assays, 650 nM TSDBB was thoroughly mixed with 1.5 units of Taq polymerase before this enzyme/reagent mixture was added to the rest of the PCR-Master and subsequent amplification. As seen in the left panel of FIG. 18 panel D, not one of the eight replicates had a SYBR Green signal, indicating that no amplification, including no primer-dimer formation, took place under this condition. This conclusion is corroborated by the right panel of FIG. 18 panel D, which shows the first derivative of the SYBR Green melt curve at end-point. Only a small low Tm "hill" due to SYBR Green binding to the stem of the TSDBB is observed. In another assay, 650 nM TSDBB was thoroughly mixed with the PCR-Master before addition of 1.5 units of Taq polymerase. As seen in the left panel of FIG. 18 panel C, SYBR Green fluorescence demonstrates the accumulation of double-stranded DNA in every sample, beginning after 30-36 cycles and continuing until scattered plateau values were reached between 44-48 cycles. The corresponding melt curve (FIG. 18 panel C, right panel) shows the presence of a somewhat scattered peak at about 77 C. This is the primer-dimer peak in these samples, which happens to have about the same Tm as the expected product. The presence of primer-dimers in all samples indicates that when the enzyme was added to the PCR-Master mix, primer-dimer formation always occurred faster than TSDBB binding to the polymerase. In a third assay, 1.5 units of GoTaq, comprised of a Taq polymerase plus a hot-start antibody, was thoroughly mixed with the PCR-Master mix, which did not include TSDBB. SYBR Green analysis (FIG. 18 panel B) shows that three of eight samples began accumulating primer-dimer products between 36-38 cycles. The presence of primer-dimers in some samples indicates that the hot-start antibody does not always block polymerase activity in the PCR-Master mix. In a fourth assay, 1.5 units of Taq polymerase, without a hot-start antibody, was thoroughly mixed with the PCR-Master mix, which did not include TSDBB. SYBR Green analysis (FIG. 18 panel A) shows that all samples generated primer-dimers and oligomerization of those dimers also occurred in some samples. These results demonstrate that the pair of primers used in this reaction were highly prone to primer-dimer formation in the absence of any hot-start.

FIG. 19 compares the level of mispriming in replicate samples prepared under the same four conditions, but with an added DNA template (+DNA). In the first assay, 650 nM TSDBB was thoroughly mixed with 1.5 units of Taq polymerase before this enzyme/reagent mixture was added to the rest of the PCR-Master and subsequent amplification. The results (FIG. 19 panel D) show that all eight replicates had a consistent SYBR Green signal beginning at 31-32 cycles and rising to a very similar plateau value in six of the eight samples. The melt analysis of these replicates shows a homogeneous single peak at 77 C, plus the expected TSDBB "valley" at 44 C. The results indicate clean amplification of the expected amplicon in all replicates. In a second assay, 650 nM TSDBB was thoroughly mixed with the PCR-Master before addition of 1.5 units of Taq polymerase.

In this case (FIG. 19 panel C), all eight replicates had a SYBR Green signal beginning at 30-32 cycles and rising to a plateau value that was scattered in four of the eight replicates. The melt analysis of these replicates shows the presence of the expected amplicon peak at 77 C, but the amplitude of this peak varies among the eight replicates. In accord with the finding in corresponding −DNA replicates (condition ii, above) these result indicates that low levels of primer-dimers were amplified in some, perhaps all of these replicates because primer-dimer formation occurred in the PCR-Master mix before the first thermal cycle. In a third assay, 1.5 units of GoTaq, comprised of a Taq polymerase plus a hot-start antibody, was thoroughly mixed with the PCR-Master mix, which did not include TSDBB. In this case (FIG. 19 panel B), all eight replicates had SYBR Green signals beginning at 30-32 cycles and rising to a plateau value that was scattered among the eight replicates. The melt analysis of these replicates shows the presence of the expected amplicon peak at 77 C, but the amplitude of this peak varies among the eight replicates. In accord with the finding in corresponding −DNA replicates (condition iii, above) these result indicates that low levels of primer-dimers were amplified in some, perhaps all of these replicates because primer-dimer formation occurred in the PCR-Master mix before the first thermal cycle. In a fourth assay, 1.5 units of Taq polymerase, without a hot-start antibody, was thoroughly mixed with the PCR-Master mix, which did not include TSDBB. SYBR Green analysis (FIG. 19 panel A) shows that all samples generated signals between 21 and 32 cycles and that plateau values were scattered. Melt analysis demonstrates the presence of a small, variable amount of amplicon in seven of the eight samples, plus additional double-stranded products in all samples. These results indicate that, in the absence of any hot-start, extensive primer-dimer formation takes place prior to the first thermal cycle and amplification of these spurious products competes with amplification of the correct product throughout the reaction.

Example 4

Suppression of Type 2 Mispriming by Exemplary Reagents Described Herein

Figure 20:
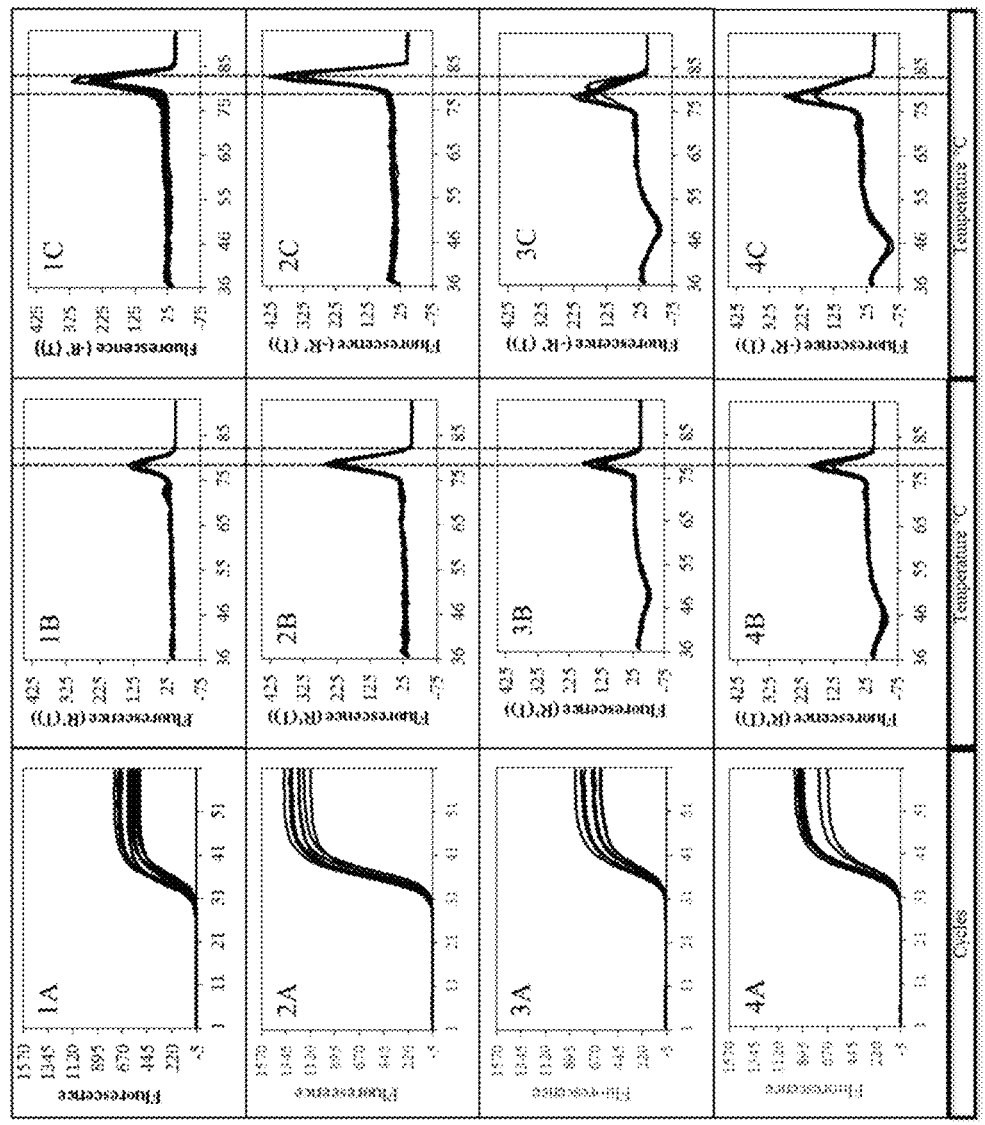
FIG. 20 shows the ability of TSDBB to suppress both type 1 and type 2 mispriming, each in a reaction containing 1.5 units of Taq polymerase.

FIG. 20 illustrates the capacity of TSDBB to suppress both Type 1 and Type 2 mispriming. Four assay conditions were compared in order to determine the effect of TSDBB on type 2 mispriming. In the first assay (FIG. 20 panel A), no hotstart antibody or reagent described herein was used. In the second assay (FIG. 20 panel B) with hotstart antibody was used. In the third assay (FIG. 20 panel C), with 900 nM PSL was used. In the fourth assay (FIG. 20 panel D), 900 nM TSDBB was used.

FIG. 20 presents the results in three columns (panels A-C from left to right). The left column shows accumulation of double-stranded DNA molecules stained with SYBR Green over the course of 60 thermal cycles. The center column shows first derivative melt curve analysis of the double-stranded molecules present at the end of 60 cycles. Following this melt curve analysis, all samples were cooled back to room temperature in the PCR machine and were then removed from the machine and stored in a refrigerator for several days. They were then placed back in the machine, reheated to 95° and amplification was resumed for 20 more cycles. For the right column, at the end of this process the samples were reexamined by melt curve analysis. Finally, the samples were once again removed from the PCR machine and prepared for sequencing using the Dilute-N-Go protocol for both strands. The results of sequencing analysis are provided below.

As seen in FIG. 20 panel A, in the absence of any hotstart reagent, the primers used in this reaction were prone to mispriming. Hence the SYBR Green signal appeared earlier than expected and plateaued at less than a maximal level. Melt analysis after 60 cycles confirmed that the products were heterogeneous. Renewed amplification of these products for 20 more cycles resulted in their further evolution of new forms whose melting temperatures were higher than after 60 cycles, when compared on these (−dF/dT) vs temperature plots. Thus, the data in presented in FIG. 20 panel A illustrate the presence of both Type 1 and Type 2 mispriming.

As seen in FIG. 20 panel B, in the presence of a hotstart antibody, mispriming prior to the start of amplification was suppressed. The SYBR Green signal appeared and plateaued at a high value, as would be expected for a clean amplicon. Melt curve analysis after 60 cycles showed the presence of a single peak of the expected Tm. Renewed amplification of this product for 20 more cycles resulted in its further evolution of the amplification product to a new form having a higher melting temperature, when compared on these (−dF/dT) vs temperature plots. Thus, as seen in FIG. 20 panel B, the hotstart antibody suppresses Type 1 mispriming but fails to suppress Type 2 mispriming.

As seen in FIG. 20 panel C, in the presence of the 900 nM PSL, mispriming prior to the start of amplification was suppressed. The SYBR Green signal appeared and plateaued at a moderately high value, as would be expected for a reasonably clean amplicon. Melt curve analysis after 60 cycles showed the presence of a single peak of the expected Tm. Renewed amplification of this product for 20 more cycles resulted in its partial evolution of the amplicon to a new form having a higher melting temperature, when compared on these (−dF/dT) vs temperature plots. Thus, as seen in FIG. 20 panel C, 900 nM PSL suppresses Type 1 mispriming but fails to completely suppress Type 2 mispriming.

As seen in FIG. 20 panel D, in the presence of the 900 nM TSDBB, mispriming prior to the start of amplification was suppressed. The SYBR Green signal appeared and plateaued at a moderately high value, as would be expected for a reasonably clean amplicon. Melt curve analysis after 60 cycles showed the presence of a single peak of the expected Tm. Renewed amplification of this product for 20 more cycles resulted in single peak having the same melting temperature at the correct amplicon, with very little evolution of amplification product to a form with a higher melting temperature, when compared on these (−dF/dT) vs temperature plots. Thus, as seen in FIG. 20 panel D, 900 nM TSDBB suppresses both Type 1 and Type 2 mispriming.

Comparison of the results in FIG. 20 panel C with those in 20D shows that 900 nM PSL is less functional in suppression of both Type 1 and Type 2 mispriming than 900 nM TSDBB. The "valleys" in the center and right columns demonstrate that the functional Tm of TSDBB, is lower than the functional Tm of PSL. Thus, fewer TSDBB molecules are in the double-stranded hairpin configuration than PSL molecules both when the temperature is being raised during the very first thermal cycle and when it is being lowered after the 60th thermal cycle. Nevertheless, TSDBB displays greater suppression of both Type 1 and Type 2 mispriming than PSL.

Additional details regarding the experimental conditions used in certain of the above examples are summarized in FIGS. 21-24.

Example 5

Multiplex LATE-PCR Amplification Using Exemplary Reagents Described Herein

A multiplex LATE-PCR amplification was performed to compare the effectiveness of reagents PSI and TSBHQ2BB to reduce the scatter among replicates. The PCR reaction contained pairs of primers specific for the following targets: (1) rpoB gene; (2) the katG gene; (3) a portion of the promoter region of the inhA gene; and (4) a synthetic oligo nucleotide target that served as an internal control. In addition, the reaction contained a non-amplified control that was used as a precise temperature indicator. The relevant sequences are as follows (a three carbon linker is denoted with $C_3$ while Black Hole Quenchers 2 are denoted with BHQ2 respectively).:

```
RpoB:
Limiting Primer:
                                    (SEQ ID NO: 1)
CTCCAGCCAGGCACGCTCACGTGACAGACCG Excess Primer:
                                    (SEQ ID NO: 2)
ACGTGGAGGCGATCACACCGCAGACGTT Probe 1 Off:
                                    (SEQ ID NO: 3)
BHQ2-CTGGTTGGTGCAGAAG-C3

Probe 2 On:
                                    (SEQ ID NO: 4)
Quasar 670-TCAGGTCCATGAATTGGCTCAGA-BHQ2

Probe 3 Off:
                                    (SEQ ID NO: 5)
BHQ2-CAGCGGGTTGTT-C3

Probe 4 On TG:
                                    (SEQ ID NO: 6)
BHQ2-ATGCGCTTGTTGGTCAACCCCGAT-Quasar 670

Probe 5 On G:
                                    (SEQ ID NO: 7)
Quasar 670-AAGCCCCAGCGCCGACAGTCGTT-BHQ2

Probe 5 On:
                                    (SEQ ID NO: 7)
Quasar 670-AAGCCCCAGCGCCGACAGTCGTT-BHQ2

Probe 6 Off:
                                    (SEQ ID NO: 8)
ACAGACCGCCGG-BHQ2

KatG:
Limiting Primer:
                                    (SEQ ID NO: 9)
AGCGCCCACTCGTAGCCGTACAGGATCTCGAGGAAAC Excess Primer:
                                    (SEQ ID NO: 10)
TCTTGGGCTGGAAGAGCTCGTATGGCAC On Probe:
                                    (SEQ ID NO: 11)
QSR670-ACTCGCGTCCTTACCCAAAAAAAAAAAAAA-BHQ2

Off Probe:
                                    (SEQ ID NO: 12)
ATGTCGGTGGTGA-BHQ2

InhA:
Limiting Primer:
                                    (SEQ ID NO: 13)
TTCCGGTAACCAGGACTGAACGGGATACGAATGGGGGTTTGG Excess Primer:
                                    (SEQ ID NO: 14)
TCGCAGCCACGTTACGCTCGTGGACATAC On Probe:
                                    (SEQ ID NO: 15)
BHQ2-AAAAAAAAAAAAAAAGGCAGTCATCCCGTT-QSR670

Off Probe:
                                    (SEQ ID NO: 16)
BHQ2-TTACAGCCTATCGCCTCGC-C3

Internal Control:
Limiting Primer:
                                    (SEQ ID NO: 17)
TTCGGCGCACAAAGTGTCTCTGGCTGTTGT Excess Primer:
                                    (SEQ ID NO: 18)
TTGGCACGATGCTCCCACATTGCGACTTC Amplifiable internal control sequence:
                                    (SEQ ID NO: 19)
GGCACGATGCTCCCACATTGCGACTTCTGCCCTTGATAGTT

ATATTGAAAGTAAATAGTAGATAGTAGATGATGATATAAAC

AACAGCCAGAGACACTTTGTGCGCCGAA

On Probe:
                                    (SEQ ID NO: 20)
QSR670A-TTCTATTATTTATTTTCAT-BHQ2

Off Probe:
                                    (SEQ ID NO: 21)
ATCATTATTTACTA-BHQ2

Non-amplified Control;
Fluor Strand:
                                    (SEQ ID NO: 22)
QSR670-CAGCTGCACTGGGAAGGGTGCAGTCTGACC-C3

Quencher Strand:
                                    (SEQ ID NO: 23)
GGTCAGACTGCACCCTTCCCAGTGCAGCTG-BHQ2

Exemplary Reagents:
PSI:
                                    (SEQ ID NO: 24)
Dabcyl-GAATAATATAGCCCCCCCCCCCCCCCCCCCCC TATATTATTC-Dabcyl TSBHQ2BB:
                                    (SEQ ID NO: 25)
BHQ2-GAATAATATAGCCCCCCCCCCCCCCCCCCCCCCC CCCCTATATTATTC-Biosearch Blue
```

LATE-PCR amplifications were performed on genomic DNA of *Mycobacterium tuberculosis* (approximately 100 genomes) with six replicates carried out in a 25 µl reaction solution made up of 1×PCR buffer (Invitrogen, Carlsbad, Calif.), 3 mM $MgCl_2$, 300 nM dNTPs, 50 nM limiting primer, 1000 nM excess primer, 150 nM of each off probe, 50 nM of each on probe with the exception of rpoB Probe 5 On TG (25 nM) and rpoB Probe 5 On G (75 nM), 1000 genome equivalents of the amplifiable internal control, 50 nM of the non-amplified control fluor strand and 150 nM of the quencher strand of the non-amplified control. Each reaction contained 1.5 Units of Taq DNA polymerase (Invitrogen, Carlsbad, Calif.) and either PSI (600 nM) or TSBHQ2BB (300 nM, 600 nM, or 1500 nM).

The thermal profile for the amplification reaction was as follows: 97° C. for 7 seconds followed by 75° C. for 45 seconds for 60 cycles, followed by 10 minutes at 75° C., followed by 10 minutes at 25° C., with a melt starting at 25° C. increasing by 1° C. increments at 30 second intervals up to 96° C., with fluorescent acquisition occurring at each interval. Probe-target hybridizations were analyzed by melt curve analysis using the first derivative for the temperatures between 25° C. and 85° C.

Figure 25:
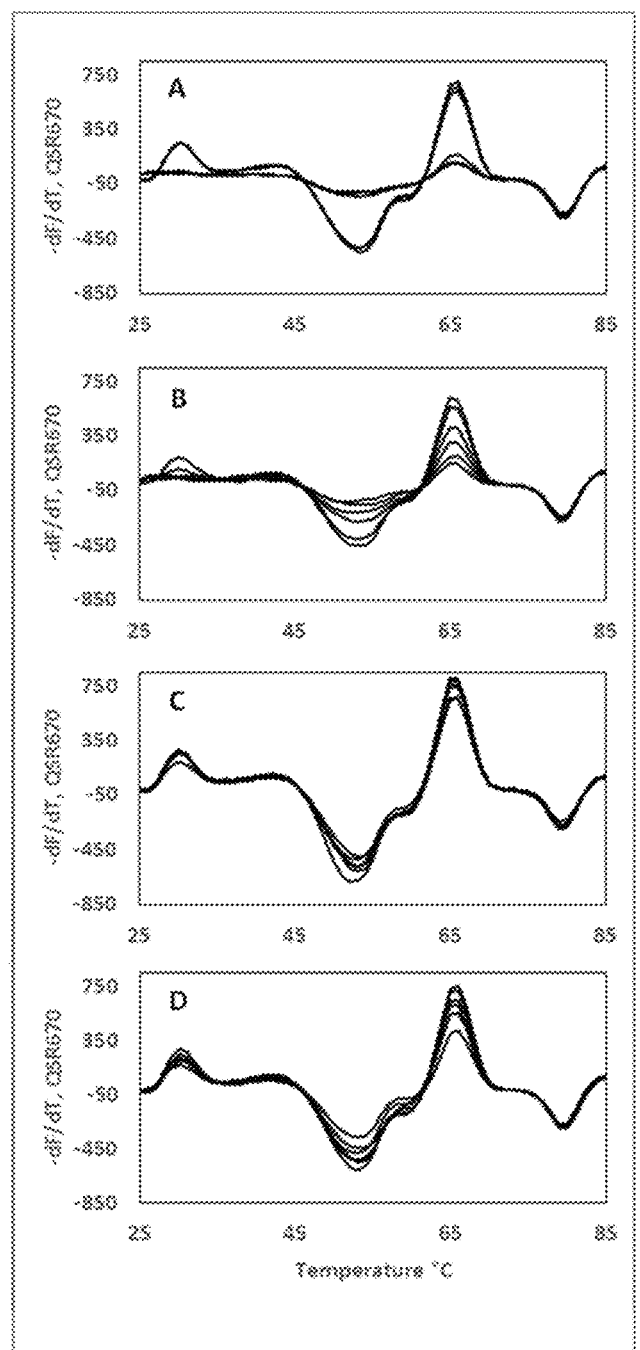
FIG. 25 shows a amplification reaction reproducibility in the presence of PSI or TSBHQ2BB. In panel A, 600 nM of PSI is present. In panel B, 300 nM of TSBHQ2BB is present. In panel C, 600 nM TSBHQ2BB is present. In panel D, 1500 of nM TSBHQ2BB is present.

FIG. 25 shows the reproducibility of the amplification results using PSI and TSBHQ2BB with a fixed amount (1.5 units) of Taq DNA polymerase. One distinct feature of all samples is the fluorescent valley at 81° C., which is the non-amplified temperature indicator showing that all reactions maintained a constant volume and salt concentration throughout the reaction. If either of these two variables were to change then the temperature at which this valley occurs would shift.

FIG. 25 panel A shows melt curves produced using the amplification products of six replicate amplifications containing 600 nM of PSI. The melt curves demonstrate that two distinct groups of reactions took place under these conditions. Three of the six replicates show amplification having a peak at 67° C., a deep valley at 50° C. and another peak at 30° C., while the other three replicates show poor amplification at these temperatures.

FIG. 25 panel B shows the melt curves produced using six replicate amplifications containing 300 nM of TSBHQ2BB. The melt curves demonstrate a gradation of amplification among replicates, indicating that 300 nM is not an optimal concentration of TSBHQ2BB for this reaction.

FIG. 25 panel C shows the melt curves produced using six replicate amplifications containing 600 nM of TSBHQ2BB. The melt curves demonstrate little scatter and consistent amplification at all three temperatures points (peak at 67° C., a deep valley at 50° C. and another peak at 30° C.). Comparison of the amplitude of the peak at 67° C. in FIG. 25 panels A and C shows that the reaction depicted in FIG. 25C is more robust as well as more consistent among replicates.

FIG. 25 panel D shows the melt curves produced using six replicate amplifications containing 1500 nM of TSBHQ2BB. The melt curves demonstrate that amplification under these conditions is similar to the amplification depicted in FIG. 25 panel C using with 600 nM TSBHQ2BB, but is less consistent between the six replicates. Thus, for the reaction conditions tested, 600 nM was the optimal TSBHQ2BB concentration.

Example 6

Improved RT-LATE-PCR Amplification Using Exemplary Reagents Described Herein

Reverse transcription (RT) and PCR reagents can be combined for the performance of reverse transcription and cDNA amplification without opening sample tubes between reactions. Such "one-step" RT-PCR protocols reduce both total assay time and the risk of sample contamination. During the RT reaction (which can last for 30 minutes or longer and can involve temperatures between 42° C. and 60° C.) the DNA polymerase should remain inactive to prevent primer dimer formation and other non-specific interactions of primers and DNA targets. This example compares the ability of DNA polymerase-specific antibodies with two exemplary Reagents, TSDBB and TSBHQ2BB, in the minimization of non-specific amplifications and the improvement of amplification of the intended target during one-step RT-PCR reactions.

Armored RNA HCV-genotype 2b (catalog #42010, Asuragen, Inc.) was used at a concentration of approximately 1,000 particles per reaction as a target for reverse transcription and amplification. SuperScript III Reverse Transcriptase and Tfi DNA polymerase (both from Life Technologies) were incubated for 10 minutes at room temperature with Platinum Antibody (Life Technologies), TSDBB, or TSBHQ2BB in 1×PCR buffer and 3 mM magnesium. Reaction mixes containing all other components (see below) with or without HCV Armored RNA in 1×PCR buffer and 3 mM magnesium were incubated 3 minutes at 75° C. to denature the protective protein surrounding the HCV Armored RNA. The enzyme mixes were then diluted 5 fold with the to obtain final concentrations of 50 nM antisense primer (AAGGTCTTTCGCAACCCAACGCTA) (SEQ ID NO: 26), 1,000 nM sense primer (GACTGGGTC-CTTTCTTGGA) (SEQ ID NO: 27), 400 nM HCV probe (Cal Red 610-TCGGCTAGTAGTCTTGTGG-BHQ2) (SEQ ID NO: 28), 0.4 mM of each dNTP, 0.24×SYBR Green, 4 U/µL SuperScriptIII, and 0.06 U/µL Tfi DNA polymerase in a final volume of 25 µL per reaction. Platinum Antibody final concentration was 0.06 U/µ when present, and TSBHQ2BB final concentration was 2 µM when present. Approximately half (i.e. 1 µM) of the TSBHQ2BB molecules have a double-stranded DNA stem at the 45° C. temperature used for reverse transcription.

Thermal cycling and fluorescence detection were done in a Stratagene Mx3005P instrument. Incubation at 45° C. for 30 minutes (RT step), then 95° C. for 2 minutes, was followed by 60 cycles of 95° C. for 10 seconds, 62° C. for 10 seconds, and 68° C. for 30 seconds, with detection for SYBR Green fluorescence. Temperature was then lowered gradually (approximately 2 degrees per minute) and held at 40° C. for 5 minutes to ensure complete hybridization of the Cal Red-labeled probe to the single-stranded amplification product. Temperature was increased in 0.5° C. increments from 40° C. to 95° C., measuring SYBR Green and Cal Red fluorescence at each step. SYBR Green fluorescence data was analyzed using the adaptive baseline setting of the Stratagene software. Cal Red fluorescence data was exported to Microsoft Excel and normalized based on the fluorescence at 70° C., a temperature at which there is no detectable hybridization of probe and amplification product.

Figure 26:
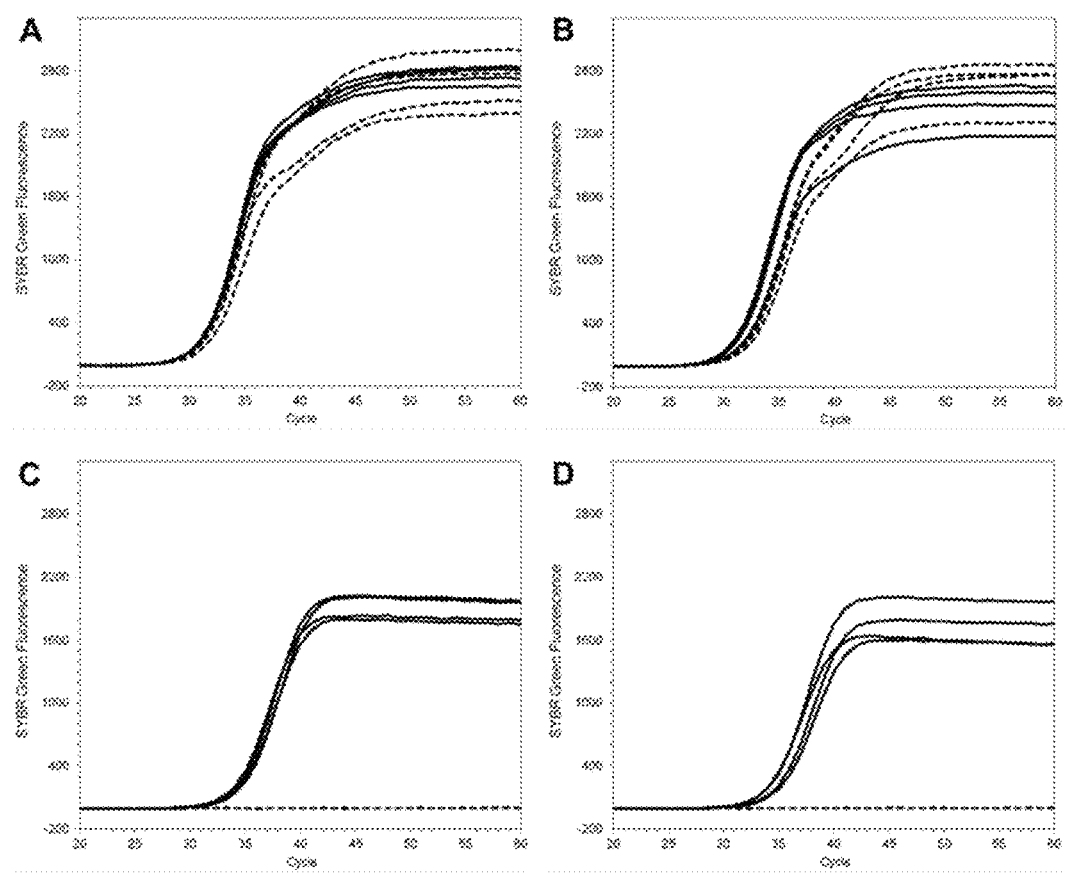
FIG. 26 shows the real time SYBR Green fluorescence increase during RT-LATE-PCR of samples with no hot start (A), Platinum Antibody (B), TSDBB (C), or TSBHQ2BB (D). Samples with HCV Armored RNA targets are shown as solid lines; No target control (NTC) samples are shown as dashed lines.

FIG. 26 shows the real time amplification of double-stranded DNA (both HCV-specific and non-specific products) using SYBR Green detection. Mean $C_T$ values were lowest in HCV samples (solid lines) containing no hot start (A) and Platinum Antibody (B) but similar $C_T$ values in no template control (NTC) samples (dashed lines) with those additives indicate that a large fraction of the fluorescence increase was due to non-specific amplification. HCV samples containing TSDBB (C) or TSBHQ2BB (D) generated mean $C_T$ values about 3.5 cycles higher, but the corresponding NTC samples did not generate any detectable amplification product, demonstrating the improved specificity with these additives.

Figure 27:
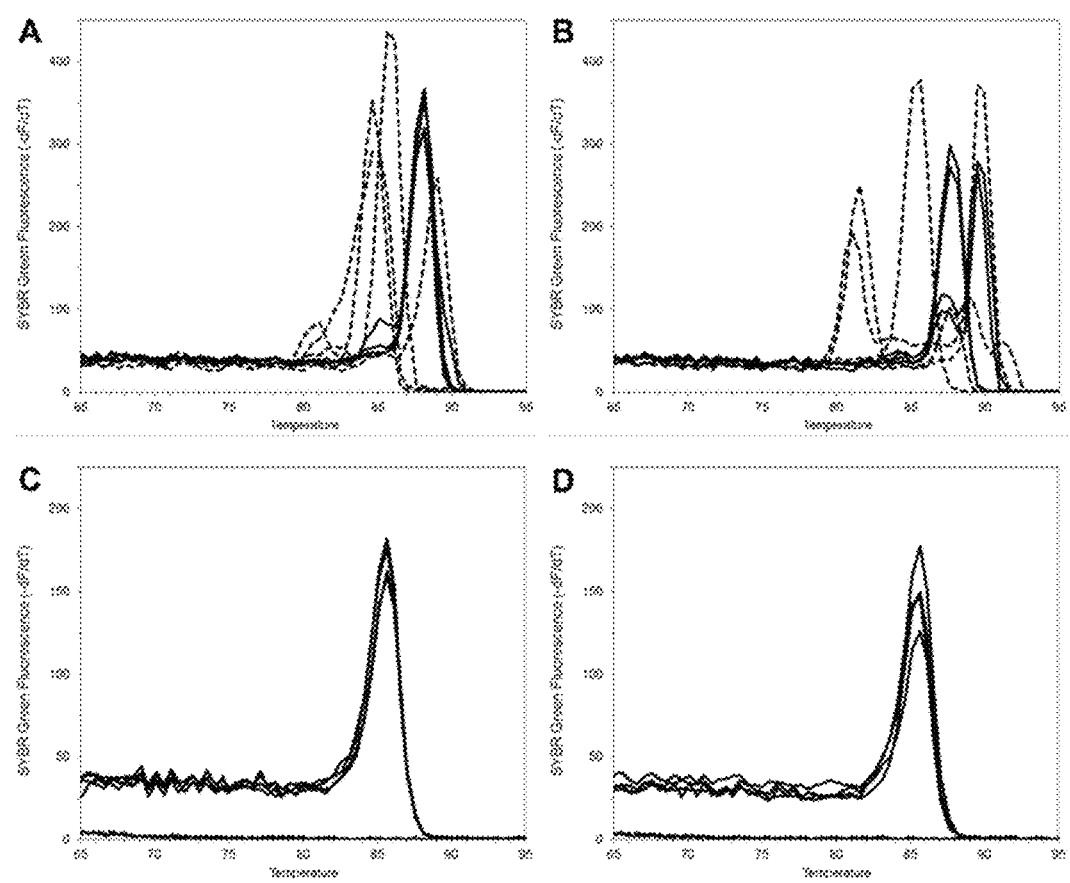
FIG. 27 shows post RT-LATE-PCR SYBR Green melting analysis for the detection of non-specific and specific amplification products in samples with no hot start (A), Platinum Antibody (B), TSDBB (C), or TSBHQ2BB (D).

SYBR Green melting analysis of the amplification products (FIG. 27) confirmed the presence of several non-specific product peaks in the (–dF/dT) vs temperature plots from HCV and NTC samples with no hot start (A) or Platinum Antibody (B). Similar results were obtained with samples containing Platinum Tfi (exo-) DNA polymerase, a version of the enzyme lacking exonuclease activity that is premixed with Platinum Antibody. In contrast, HCV samples with TSDBB (C) or TSBHQ2BB (D) showed single product peaks at the expected melting temperature of the HCV amplicon.

Figure 28:
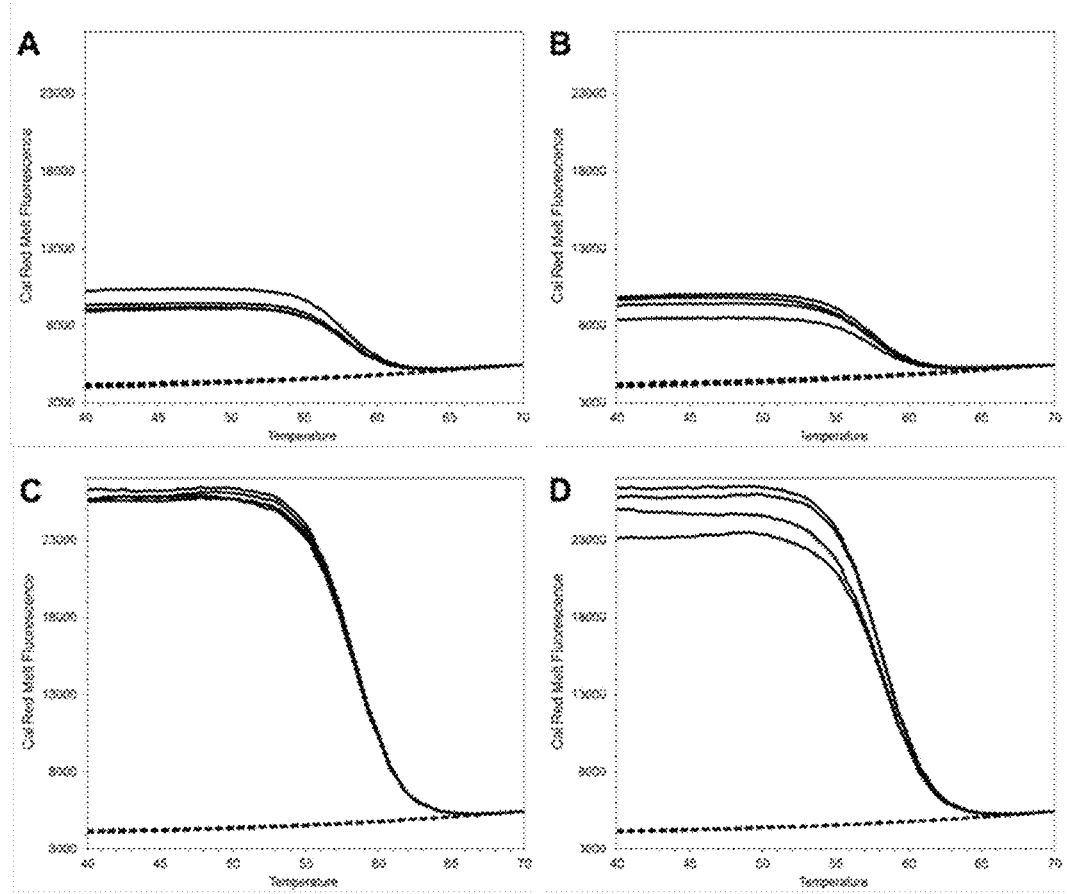
FIG. 28 shows post RT-LATE-PCR melting analysis of HCV probe fluorescence in samples with no hot start (A), Platinum Antibody (B), TSDBB (C), or TSBHQ2BB (D).

Melting analysis of HCV probe hybridization (FIG. 28) confirmed a low-level of HCV-specific amplification product in HCV samples containing no hot start (A) and Platinum Antibody (B) and a 4-fold increase in detectable HCV probe fluorescence above background in HCV samples containing TSDBB (C) or TSBHQ2BB (D).

These results demonstrate that exemplary reagents described herein reduce non-specific amplification and increase specific target amplification in one-step RT-PCR reactions relative to that observed using an antibody hot start. Without being bound by theory, the improved specificity may be due to an inhibition of primer dimer extension during the RT incubation.

Example 7

Improved RT-PCR Amplification Using Exemplary Reagents Described Herein

A one-step RT-PCR experiment similar to that in Example 6 was performed, but using Taq DNA polymerase instead of Tfi DNA polymerase and using symmetric PCR instead of LATE-PCR. Enzyme mixes were prepared as described in Example 6, except that Taq DNA polymerase was substituted for Tfi DNA polymerase. The HCV Armored RNA target and amplification reagents used were used at the same concentrations except that the sense primer concentration was 500 nM and a different antisense primer (CTTTCG-CAACCCAACGCTA) (SEQ ID NO: 29) was used at 500 nM.

Thermal cycling and fluorescence detection were done in a Stratagene Mx3005P instrument. Incubation at 45° C. for 30 minutes (RT step), then 95° C. for 2 minutes, was followed by 20 cycles of 95° C. for 10 seconds, 62° C. for 10 seconds, and 72° C. for 30 seconds, then 30 cycles of 95° C. for 10 seconds, 60° C. for 10 seconds, and 72° C. for 30 seconds with detection for Cal Red (analysis at 60° C.) and SYBR Green fluorescence (analysis at 72° C.). Temperature was then lowered gradually (approximately 3 degrees per minute) and held at 40° C. for 2 minutes then increased in 0.5° C. increments from 40° C. to 95° C., with fluorescence detection at each increment.

Figure 29:
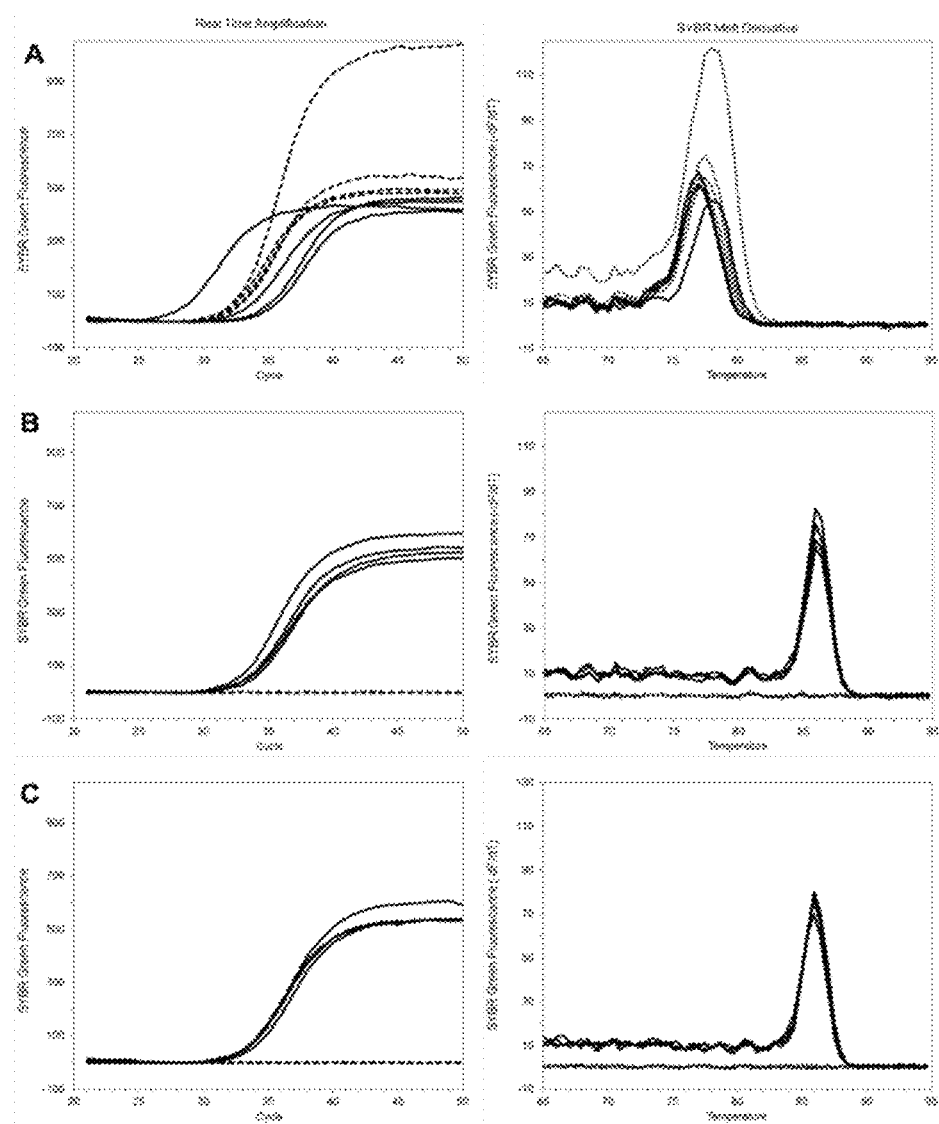
FIG. 29 shows real-time SYBR Green fluorescence increase (left) and post-RT-PCR melt derivative plots (right) in HCV (solid lines) and NTC (dashed lines) samples with Platinum Antibody (A), TSDBB (B), or TSBHQ2BB (C).

SYBR Green detection during amplification and post RT-PCR melting is shown in FIG. 29. The $C_T$ values of replicate HCV samples containing Platinum Antibody (FIG. 29 panel A, left panel, solid lines) were highly variable. No target control (NTC) samples containing Platinum Antibody (dashed lines) also showed double stranded DNA amplification with $C_T$ values of 32 to 33. Melting analysis, (−dF/dT) vs temperature plots, revealed that all amplification products in both HCV and NTC samples containing Platinum Antibody (FIG. 29 panel A, left panel) were non-specific with $T_m$ below 80° C. and no HCV-specific product was detected at the expected $T_m$ of 86° C. In contrast, HCV samples with TSDBB gave more consistent amplification with a mean $C_T$ value of 34, and NTC samples with TSDBB showed no fluorescence increase (FIG. 29 panel B, left panel). Melting analysis, (−dF/dT) vs temperature plots, of the HCV samples with TSDBB showed a single detectable melt peak at the specific product Tm of 86° C. (FIG. 29 panel B, right panel). Results for the HCV and NTC samples containing TSBHQ2BB (FIG. 29 panel C) were similar to those in samples containing TSDBB.

These results demonstrate that exemplary Reagents described herein reduce non-specific amplification in one-step RT-PCR reactions containing Taq DNA polymerase relative to that observed using an antibody hot start.

The melting temperature of the single-stranded mispriming prevention reagent hairpin could be modified to increase the inhibitory effect of single-stranded mispriming prevention reagent at 45° C. or higher temperatures (e.g. 50° C., 55° C., or 60° C.) by increasing the length of the stem, it's nucleotide sequence (e.g. by increasing the ratio of G-C pairs to A-T pairs), or by decreasing the length of the loop. Thus, different RT incubation temperatures could be used while still inhibiting activity of the DNA polymerase. Single-stranded mispriming prevention reagent should affect the activity of a broad range of polymerases that might be used for RT-PCR.

Example 8

Use of Exemplary Reagents Described Herein in Two-Step RT-PCR

Examples 6 and 7 demonstrate improved amplification of a specific RNA target by exemplary Reagents described herein in a one-step RT-PCR reaction. This example tests the effect of exemplary Reagents described herein on the fidelity of reverse transcriptase during the RT reaction in the absence of a DNA polymerase. Amplification is then completed in a separate PCR step following the equalization of the exemplary Reagent concentrations in all samples.

Figure 31:
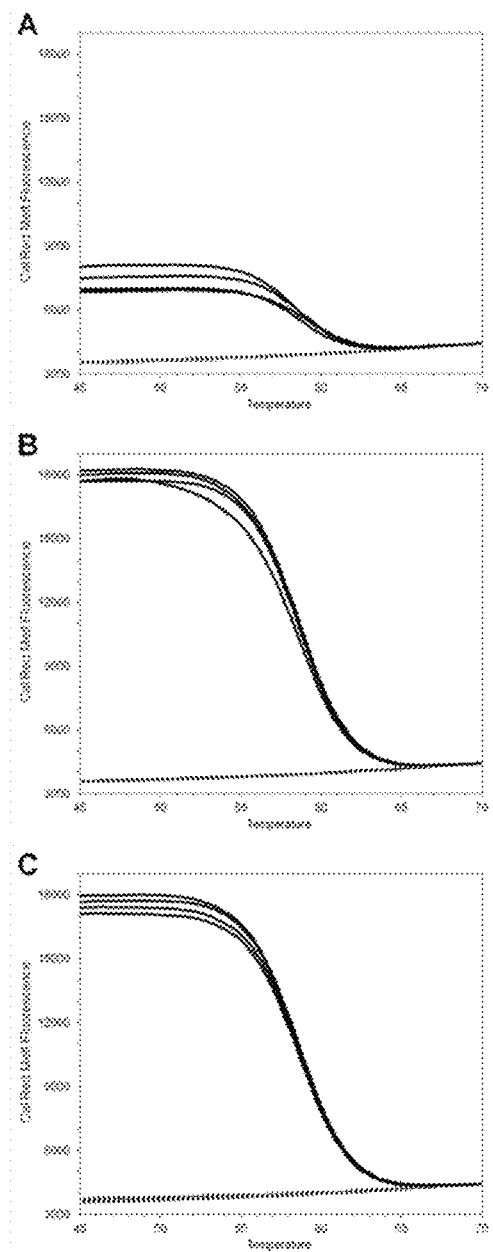
FIG. 31 shows post RT-LATE-PCR melting analysis of HCV probe fluorescence in samples with no TSBHQ2BB (A), with TSDBB (C), or with TSBHQ2BB (D) during RT of a two-step RT-LATE-PCR. Baseline fluorescence in control samples without reverse transcriptase is shown by the dotted lines.

A mixture of 500 nM antisense primer, 10 μM sense primer (both described in Example 6), and about 500 copies/μL HCV-2b Armored RNA in 1×Tfi polymerase reaction buffer and 3 mM magnesium chloride was incubated at 75° C. for 3 minutes, cooled to 25° C. and then mixed with an equal volume of an RT reagent mixture containing 20 U/μL SuperScript III, 0.8 mM each dNTP, and either 4 μM TSDBB, or 4 μM TSBHQ2BB, or no exemplary Reagent in 1×Tfi polymerase reaction buffer and 3 mM magnesium chloride, incubated at 45° C. for 30 minutes, 95° C. for 2 minutes, cooled to 25° C. and placed on ice. RT samples were diluted 5 fold with a PCR reagent mix to obtain final concentrations of 50 nM antisense primer, 10 μM sense primer, 400 nM HCV probe, 0.4 mM each dNTP, 0.24× SYBR Green, and 0.06 U/μL Tfi DNA polymerase in a final volume of 20 μL per sample. TSBHQ2BB was included in all samples to achieve a final TSBHQ2BB total concentration to 1 μM in order to provide similar hot-start PCR conditions for all samples. PCR thermal cycling (beginning with the 2 minute denaturation step at 95° C.) and post-PCR melting protocols were identical to those described in Example 6, FIG. 31.

Figure 30:
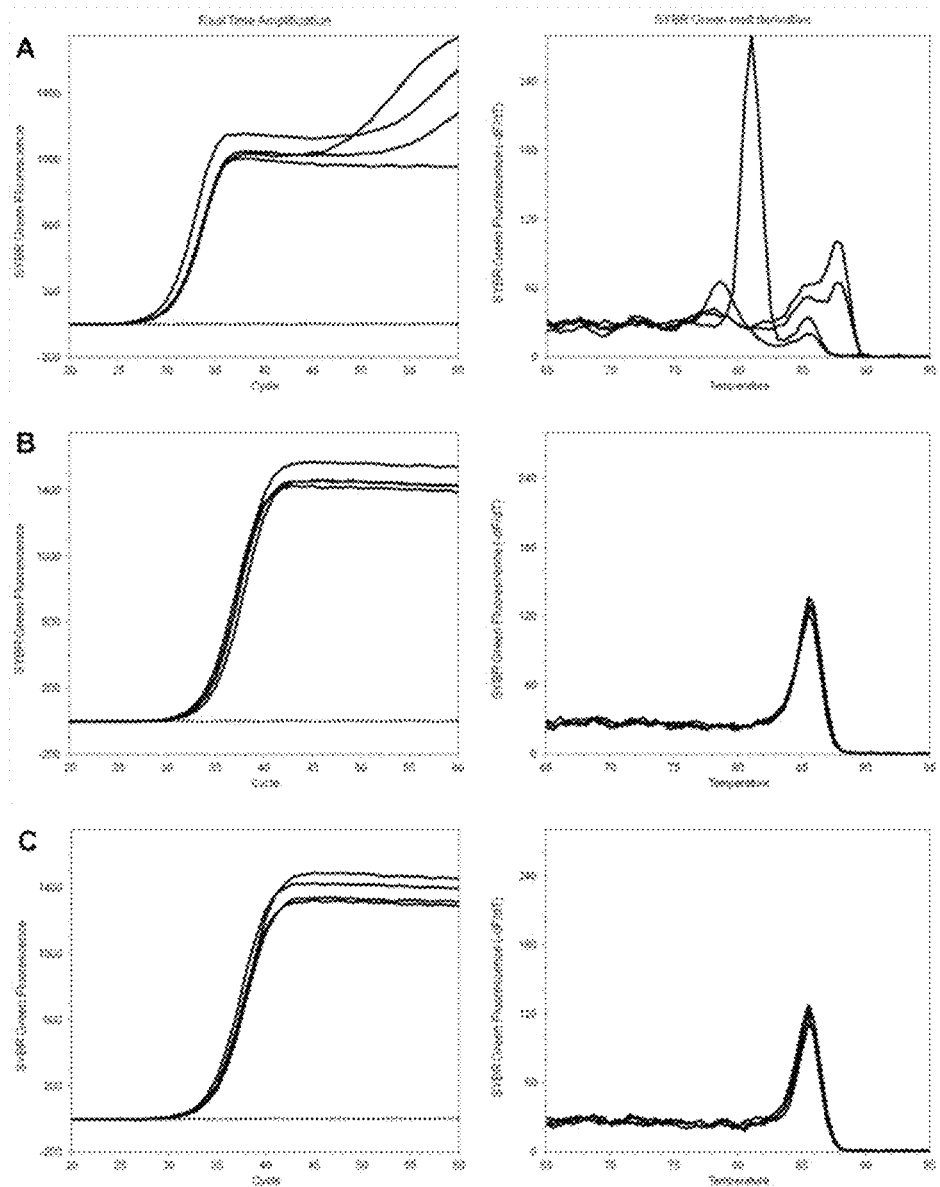
FIG. 30 shows real-time SYBR Green fluorescence increase (left) and post-RT-PCR melt derivative plots in HCV samples with no TSBHQ2BB (A), with TSDBB (B), or with TSBHQ2BB (C) during RT of a two-step RT-LATE-PCR. Control samples lacking reverse transcriptase are indicated by the dotted lines in the real time plots.

The lowest SYBR Green $C_T$ values (mean=31.2) were observed in samples that did not have an exemplary Reagent present during the RT step (FIG. 30 panel A, left), but the melt analysis revealed that much of the amplification in those samples was non-specific (FIG. 30 panel A, right). A small, variable amount of amplification product melted at the 86° C. temperature expected for the HCV-specific product. One of the replicate samples showed a secondary rise in real-time PCR fluorescence after the initial plateau with a very large melt peak at 81° C. Two samples that showed a later secondary fluorescence increase during PCR contained melt peaks at 88° C., higher than that of the specific product. Control samples prepared without reverse transcriptase showed no fluorescence increase.

SYBR Green amplification and melting analysis results in samples containing either TSDBB or TSBHQ2BB (FIG. 30 panels B and C, respectively) during the RT step showed higher mean $C_T$ values (34.6 and 35.0, respectively) compared to the samples without Reagent, but no secondary fluorescence increase was observed after reaching plateau, and melting analysis, (−dF/dT) vs temperature plots, revealed only the HCV-specific product melt peak at 86° C. Control samples prepared without reverse transcriptase showed no fluorescence increase.

Higher levels of the HCV-specific product were confirmed with HCV probe melting analysis. The mean fluorescence above baseline in samples with either exemplary Reagent was nearly 4 times that of samples in which Reagent was not present in the RT step.

These results indicate that exemplary Reagents described herein prevent the initial formation of non-specific products during the RT step in the absence of DNA polymerase. Since all Reagent concentrations in the reactions are identical during the PCR step, the source of any amplification differences must take place during RT. Modified reagents can be designed with at least some RNA nucleotides, or synthetic nucleotides (e.g. 2'-O-methyl RNA) to increase their affinity to reverse transcriptase in order to further increase specificity and/or to inhibit the RNA-dependent DNA polymerase activity at specific temperatures. Thus, a "hot start" can be applied to RT reactions much in the same way as is currently done with PCR. Also, other versions of a single-stranded mispriming prevention reagent described herein could be designed as inhibitors of other polymerases, including RNA-dependent RNA polymerases. These types of inhibitors have potential applications not only in molecular tests, but as possible drugs to inhibit RNA viruses and other infectious agents.

Example 9

Use of Exemplary Reagents Described Herein in One-Step RT-LATE-PCR

The above example with two-step RT-PCR indicates that the single-stranded mispriming prevention reagents described herein are able to improve reverse transcription by acting directly on the reverse transcriptase. To examine this more directly in one-step RT-PCR, an experiment similar to that of Example 6 was done, but using AmpliTaq Gold DNA polymerase (ThermoFisher Scientific) instead of Tfi polymerase. According to the manufacturer, that enzyme is a chemically modified form of AmpliTaq® DNA Polymerase requiring thermal activation. The modified enzyme is provided in an inactive state. Upon thermal activation for 10 minutes at 95° C., the modifier is permanently released, regenerating active enzyme. Thus, amplification differences between samples which are identical except for the presence or absence of a single-stranded mispriming prevention reagent (or other additive) can be attributed to the action of the additive during the RT phase of the reaction, presumably due to direct interaction of the additive and the reverse transcriptase.

Enzyme mixes were prepared as was done in Example 6, except that AmpliTaq Gold DNA polymerase and the buffer supplied with that enzyme (Buffer 1) was substituted for Tfi DNA polymerase, the Platinum Antibody, and the Tfi buffer. The HCV Armored RNA target and other RT-LATE-PCR reagents were used at the same final concentrations as in that example. One set of samples contained 2 μM of the single-stranded mispriming prevention reagent BHQ2BB. A second set of samples contained 2 μM PSL, an oligonucleotide having the same sequence as BHQ2BB, but with both ends modified with Dabcyl instead of Black Hole Quencher 2 and BioSearch Blue.

Thermal cycling and fluorescence detection were done in a Stratagene Mx3005P using the same protocol as described in Example 6, except that the duration of the 45° C. incubation for RT was 15 minutes (instead of 30 minutes) and the extension step during PCR cycling was at 72° C. (instead of 68° C.).

Figure 32:
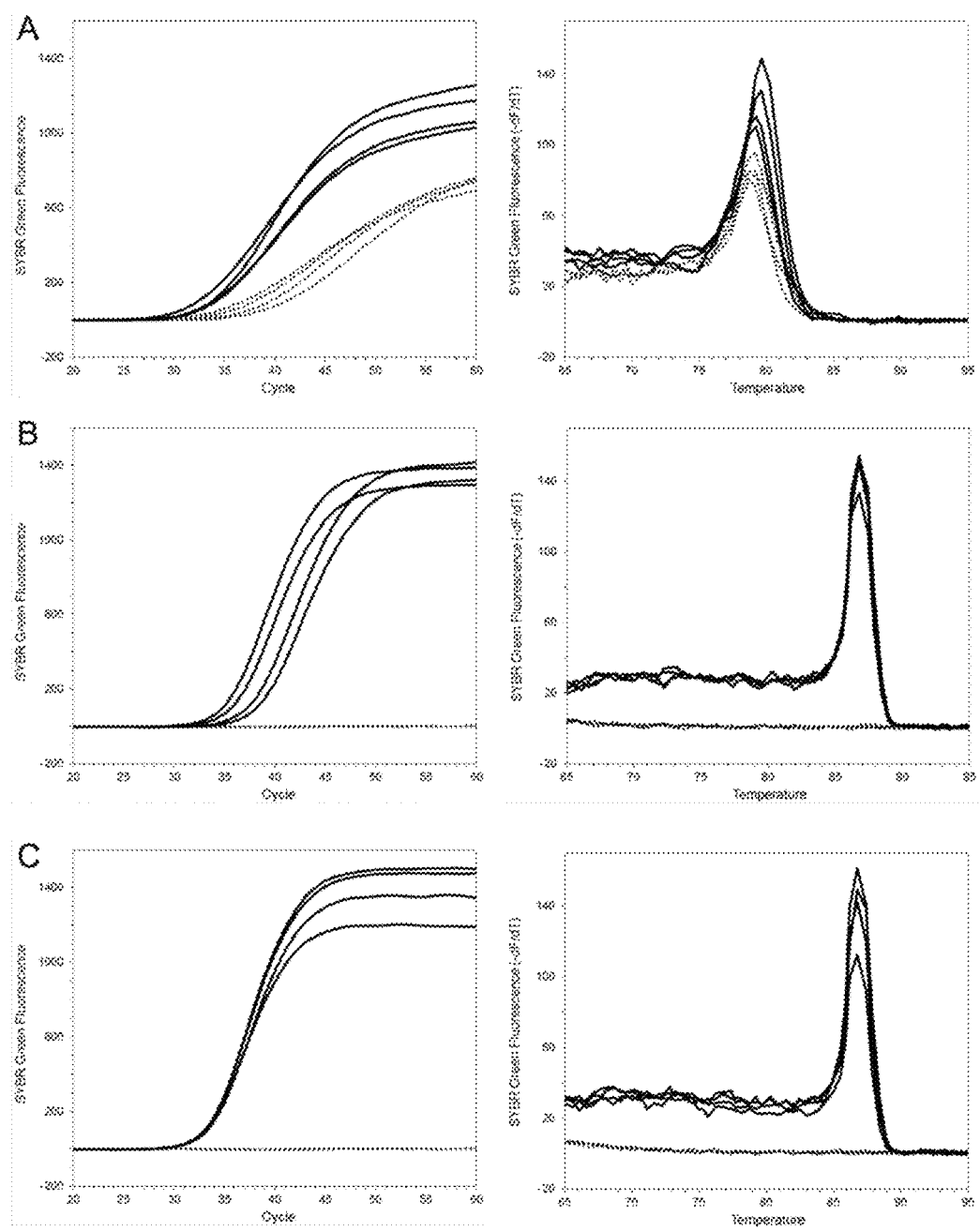
FIG. 32 shows real-time SYBR Green fluorescence increase (left) and post-RT-PCR melt derivative plots (right) in one-step RT-LATE-PCR samples containing AmpliTaq Gold with no additive (A), with PSL (B), or with BHQ2BB (C). Samples containing HCV AR are indicated by the solid lines; samples without template are indicated by the dotted lines.

Real-time SYBR Green detection of total double-stranded DNA during PCR and subsequent melting analysis is shown in FIG. 32. SYBR Green Fluorescence increase was observed in all replicates containing HCV AR (solid lines) without additive and in No Template Control (NTC) samples (dotted lines) without additive (FIG. 32 panel A, left). Mean $C_T$ values were 35.5±0.8 and 41.6±1.8 respectively. Melting analysis indicated that all detectable amplification was non-specific, as melting peaks were observed at approximately 79° C. (FIG. 32 panel A, right), rather than the specific product peak of 86° C. (FIG. 32 panels B and C, right). HCV AR samples with PSL showed SYBR Green fluorescence increase with a mean $C_T$ value of 37.7±1.6 (FIG. 32 panel B, left). None of the four NTC samples with PSL showed fluorescence increase. Melting analysis of the HCV AR samples with PSL showed single large melting peaks at approximately 86° C., indicating the presence of the HCV-specific product (FIG. 32 panel B, right). HCV AR samples with BHQ2BB showed SYBR Green fluorescence increase with a mean $C_T$ value of 34.3±0.1 (FIG. 32 panel C, left), much lower than that observed with PSL and with a much lower standard deviation. None of the four NTC samples with BHQ2BB showed fluorescence increase. Melting analysis showed the specific product peak in samples with HCV AR and BHQ2BB (FIG. 32 panel C, right).

Figure 33:
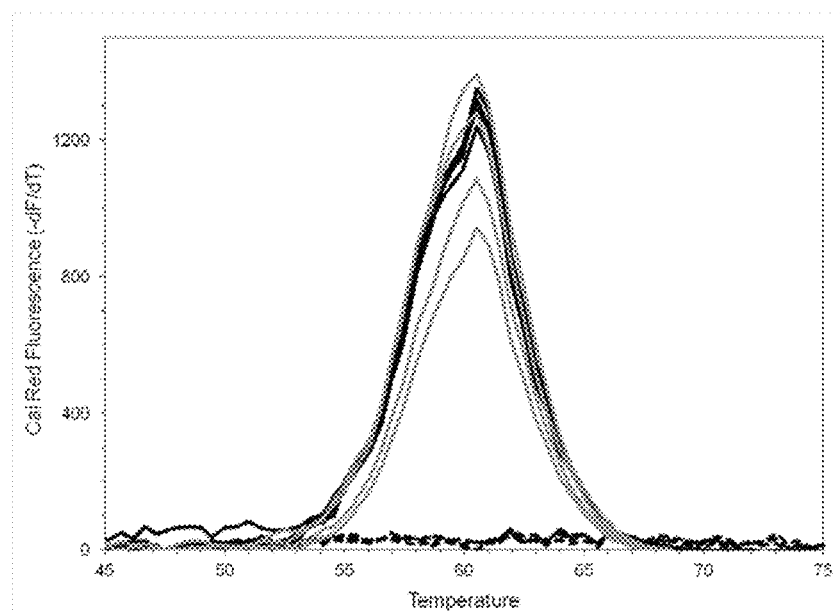
FIG. 33 shows post RT-LATE-PCR melting derivative plots of HCV probe fluorescence in samples with no additive (dashed black lines), PSL (solid gray lines), or BHQ2BB (solid black lines). The presence of the melting peak at 60° C. is characteristic of the HCV probe melting from the hybridized HCV amplification product.

The hybridization and dissociation of the fluorescently labeled probe that is specific for the HCV product was also monitored during post RT-PCR melting. None of the NTC samples in any group showed probe signal above background (not shown). The HCV AR samples containing either PSL or BHQ2BB showed strong fluorescence above background that dropped rapidly as the temperature was raised above the 60° C. melting temperature of the probe. This is graphically shown as fluorescence derivative peaks in FIG. 33. Samples without additive did not have a derivative peak, consistent with an absence of HCV-specific product.

Example 10

Use of Exemplary Reagents Described Herein in One-Step Symmetric RT-PCR

An experiment was done to determine if improvements in one-step RT-PCR observed with LATE-PCR would also be obtained when performing symmetric PCR. The reagent mixes were prepared as in Example 9, except the sense primer concentration was 500 nM and a different antisense primer, 5'-CTTTCGCAACCCAACGCTA-3' (SEQ ID NO: 29), was used at 500 nM. Thermal cycling and fluorescence detection were identical to the previous experiment.

Figure 34:
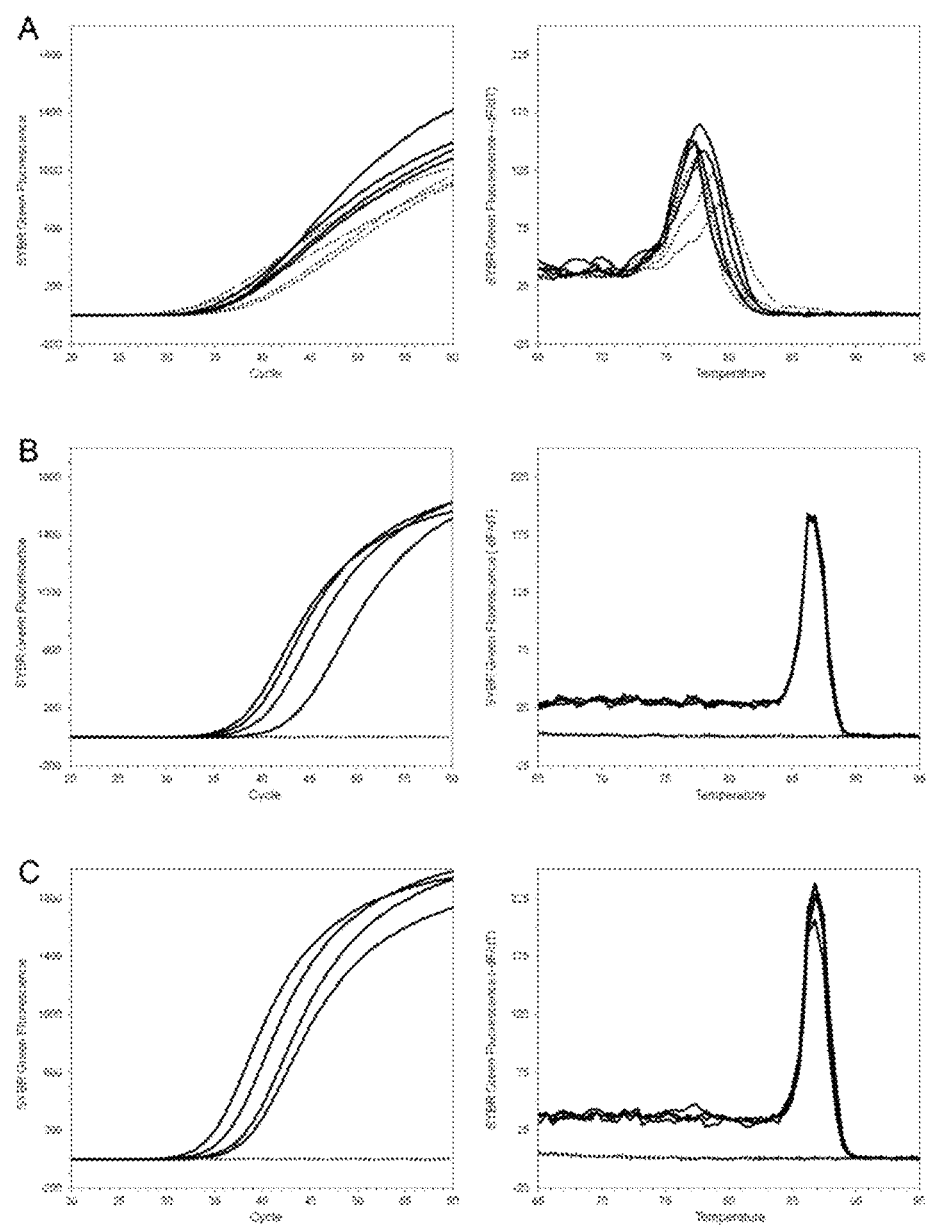
FIG. 34 shows real-time SYBR Green fluorescence increase (left) and post-RT-PCR melt derivative plots (right) in one-step RT-PCR (symmetric PCR) samples containing AmpliTaq Gold with no additive (A), with PSL (B), or with BHQ2BB (C). Samples containing HCV AR are indicated by the solid lines; samples without template are indicated by the dotted lines.

Real-time SYBR Green detection of total double-stranded DNA during PCR and subsequent melting analysis is shown in FIG. 34. SYBR Green Fluorescence increase was observed in all replicates containing HCV AR (solid lines) without additive and in No Template Control (NTC) samples (dotted lines) without additive (FIG. 34 panel A, left). Mean $C_T$ values were 38.9±0.8 and 39.8±2.6 respectively. Melting analysis indicated that all detectable amplification was nonspecific, as melting peaks were observed in the range of 77 to 79° C. (FIG. 34 panel A, right), rather than the specific product peak of 86° C. (FIG. 34 panel A, right). HCV AR samples with PSL showed SYBR Green fluorescence increase with a mean $C_T$ value of 40.8±2.3 (FIG. 34 panels B and C, left). None of the four NTC samples with PSL showed fluorescence increase. Melting analysis of the HCV AR samples with PSL showed single large melting peaks at approximately 86° C., indicating the presence of the HCV-specific product (FIG. 34 panel B, right). HCV AR samples with BHQ2BB showed SYBR Green fluorescence increase with a mean $C_T$ value of 37.1±1.8 (FIG. 34 panel C, left), lower than that observed with PSL. Fluorescence at cycle 60 was higher than in HCV AR samples with PSL or without additive. None of the four NTC samples with BHQ2BB showed fluorescence increase. Melting analysis showed the specific product peak in samples with HCV AR and BHQ2BB.

The results with SYBR Green detection confirm that BHQ2BB and PSL have similar effects on one-step RT-PCR using symmetric primers as observed using RT-LATE-PCR, interacting directly with the reverse transcriptase to improve reverse transcription and subsequent amplification of specific RNA targets. Of the reagents tested, BHQ2BB yielded the best results, lowering $C_T$ values and generating higher levels of fluorescence from the HCV-specific product.

The Cal Red-labeled HCV probe cannot detect the HCV product in symmetric PCR samples, as hybridization of the PCR product strands prevents hybridization of the low-$T_m$ probe. However, examination of the raw Cal Red fluorescence revealed a much higher level of fluorescence at the start of PCR in samples without additive compared to that in samples with either PSL or BHQ2BB (FIG. 35). The higher fluorescence levels were present in samples with HCV AR and in control samples without template, suggesting that the increase is likely due to hydrolysis of the probe by exonuclease activity even in the absence of probe hybridization. Similar high Cal Red fluorescence was observed when this probe was used without PSL or BHQ2BB in RT-LATE-PCR samples (not shown). Since the digestion of the probe oligonucleotide occurs prior to PCR, this exonuclease activity must be present in SuperScript III reverse transcriptase or in the chemically inactivated AmpliTaq Gold Taq polymerase. The activity is greatly reduced or eliminated in the presence of either PSL or BHQ2BB. Thus, these additives have the advantage of reducing target-independent hydrolysis of susceptible oligonucleotide probes, insuring sufficient intact probe is present during PCR to detect the amplification of the specific target.

Example 11

Designing of Exemplary Single-Stranded Mispriming Prevention Reagents for Rt-PCR Versions of the single-stranded mispriming prevention reagents described herein that include RNA or RNA-like nucleotides are likely to be particularly useful in reverse transcriptase reactions. The use of such reagents could enable the use of lower concentrations of single-stranded mispriming prevention reagent to achieve similar improvements to RT-PCR as described in the other examples. Versions of single-stranded mispriming prevention reagent containing RNA could also be used at high concentrations that would inhibit the enzyme over a desired range of temperatures. Such inhibition would provide a hotstart for reverse transcription, similar to the way DNA versions of single-stranded mispriming prevention reagent provide a hotstart for PCR by inhibiting DNA polymerases at low temperature. For example, a single-stranded mispriming prevention reagent containing RNA nucleotides with a hairpin $T_m$ of about 45° C. could inhibit a reverse transcriptase prior to and during initial heating, thus minimizing the likelihood of extension of primers on mismatched (and therefore low-melting) RNA targets. Once the temperature is raised to 55° C. or 60° C., temperatures at which the stem should be dissociated in the vast majority of single-stranded mispriming prevention reagent molecules, the affinity to the reverse transcriptase is reduced, and extension of primers on the specific targets can take place. Variations of single-stranded mispriming prevention reagent with different hairpin $T_m$'s could be designed to control enzyme activity at different temperatures. Using combinations of different versions of single-stranded mispriming prevention reagent (e.g. one containing RNA and one consisting of only DNA) could provide hot start for the RT step and maintain increased accuracy and/or efficiency once the RT incubation temperature is reached.

Computer software that provides an estimate of the hairpin Tm can be used when designing different variations of single-stranded mispriming prevention reagent. The Integrated DNA Technologies OligoAnalyzer 3.1 (https://www.idtdna.com/calc/analyzer) was used to provide the $T_m$ estimates provided herein below. That website tool estimates the hairpin $T_m$ of oligonucleotides containing either RNA (including 2'O-methyl RNA) or DNA nucleotides. Note that estimates are given without consideration for the presence of end modifications, which are present on the single-stranded mispriming prevention reagent and may affect the hairpin $T_m$. The increase or decrease in stem Tm may vary for different end modifications.

Single-stranded mispriming prevention reagents containing only DNA nucleotides has a predicted hairpin $T_m$ of 45° C. at the salt concentrations used in previous examples. That value is a few degrees below the observed value, determined experimentally using the methods described in previous examples. Single-stranded mispriming prevention reagents with the analogous RNA sequence has a predicted hairpin $T_m$ of 63° C.

```
                                           (SEQ ID NO: 30)
5'-rGrArArUrArArUrArArUrArGrCrCrCrCrCrCrCrCrCrCr

CrCrCrCrCrCrCrCrCrCrCrCrCrCrCrCrCrCrCrUrArUrAr

UrUrArUrUrC-3'

(RNA = rA, rG, rC, rU)
```

A sequence with RNA in the stem portion and DNA in the loop should have a similar hairpin $T_m$ and could be used as an alternative.

```
                                           (SEQ ID NO: 31)
5'-rGrArArUrArArUrArUrArGCCCCCCCCCCCCCCCCCCCCC

CCCCCCCrCrUrArUrArUrUrArUrUrC-3'
```

2'-O-methyl RNA nucleotides are preferred to standard RNA nucleotides, as RNA oligonucleotides made from them are more stable and resistant to nucleases. OligoAnalyzer 3.1 provides the same $T_m$ estimate for 2'O-methyl RNA as for standard RNA.

(SEQ ID NO: 32)
5'-mGmAmAmUmAmAmUmAmUmAmGCCCCCCCCCCCCCCCCCCCCCC

CCCCCCCmCmUmAmUmAmUmAmUmUmC-3'

(2'O-Methyl RNA = mA, mG, mC, mU)

Single-stranded mispriming prevention reagent molecules with the above nucleotide sequences might provide some improvement of RT-PCR if used at low concentrations, but high concentrations (e.g. 1 µM) are likely to strongly inhibit reverse transcriptases. Therefore, other changes in the sequences were made to lower the hairpin $T_m$.

Increasing the size of the loop reduces the $T_m$ of the hairpin. Accordingly, the number of C residues was increased from 28 to 34. However, that only reduced the predicted hairpin $T_m$ one degree. While such changes may enable small desired adjustments, additional modifications that have greater effects on hairpin $T_m$ were desired. Therefore, the mG and mC nucleotides adjacent to the stem were deleted, reducing the stem length to 10, and the mG and mC nucleotides at the ends were changed to mU and mA, respectively. The predicted hairpin Tm was 52° C.

(SEQ ID NO: 33)
5'-mUmAmAmUmAmAmUmAmUmACCCCCCCCCCCCCCCCCCCCCCCC

CCCCCCCCCCmUmAmUmAmUmAmUmAmA-3'

Single-stranded mispriming prevention reagent RNA molecules with even lower hairpin $T_m$ could be designed by reducing the number of nucleotides in the stem. However, our more preferred versions of single-stranded mispriming prevention reagent have a stem length of at least 10 nucleotides. An alternative method of using mG to mU pairing was used to reduce the hairpin Tm. The mG to mU pairing (or rU to rG pair) is slightly destabilizing compared to the mA to mU pairing. Therefore, 3 mA nucleotides were replaced with mG. The resulting predicted hairpin Tm was 40° C. At high concentrations, this version of single-stranded mispriming prevention reagent (with BioSearch Blue and Black Hole Quencher, or other end modifications) is likely to provide temperature-controlled inhibition of reverse transcriptase.

(SEQ ID NO: 34)
5'-mUmAmAmUmAmGmUmGmUmACCCCCCCCCCCCCCCCCCCCCCCC

CCCCCCCCCCmUmGmUmAmUmAmUmAmA-3'

An alternative design is the use of RNA for one half of the stem and DNA for the other half (RNA or DNA could be used in the loop). The RNA-DNA hybrid would be more similar to a DNA primer used for reverse transcription of an RNA template. The RNA-DNA hybrid has a lower $T_m$ than the analogous RNA-RNA hybrid. The oligonucleotide sequence below should have a hairpin $T_m$ between that of the analogous RNA-RNA sequence (above) that has a predicted hairpin $T_m$ of 52° C. and the analogous DNA-DNA sequence that has a predicted hairpin $T_m$ of 37° C. A hairpin $T_m$ estimate for the mixed nucleotide was not provided by the OligoAnalyzer 3.1. The preferred $T_m$ estimate for this and other versions of the single-stranded mispriming prevention reagent are determined empirically, as described previously.

(SEQ ID NO: 35)
5'-mUmAmAmUmAmAmUmAmUmACCCCCCCCCCCCCCCCCCCCCCCC

CCCCCCCCCCCTATATTATTA-3'

The preferred end modifications for any of the above sequences are BioSearch Blue and Black Hole Quencher, but other modifications with similar chemical and physical properties could be used as alternatives. There are many possible alternative nucleotide sequences, stem lengths and loop lengths that could be used as alternatives to the sequences given above. Mixing RNA and DNA nucleotides along one side of the stem is another possible variation. These variations could provide a spectrum of single-stranded mispriming prevention reagent molecules for use at different RT incubation temperatures.

Example 12

Exemplary Reagents Containing Black Hole Quencher Moieties Besides Dabcyl

Figure 37:
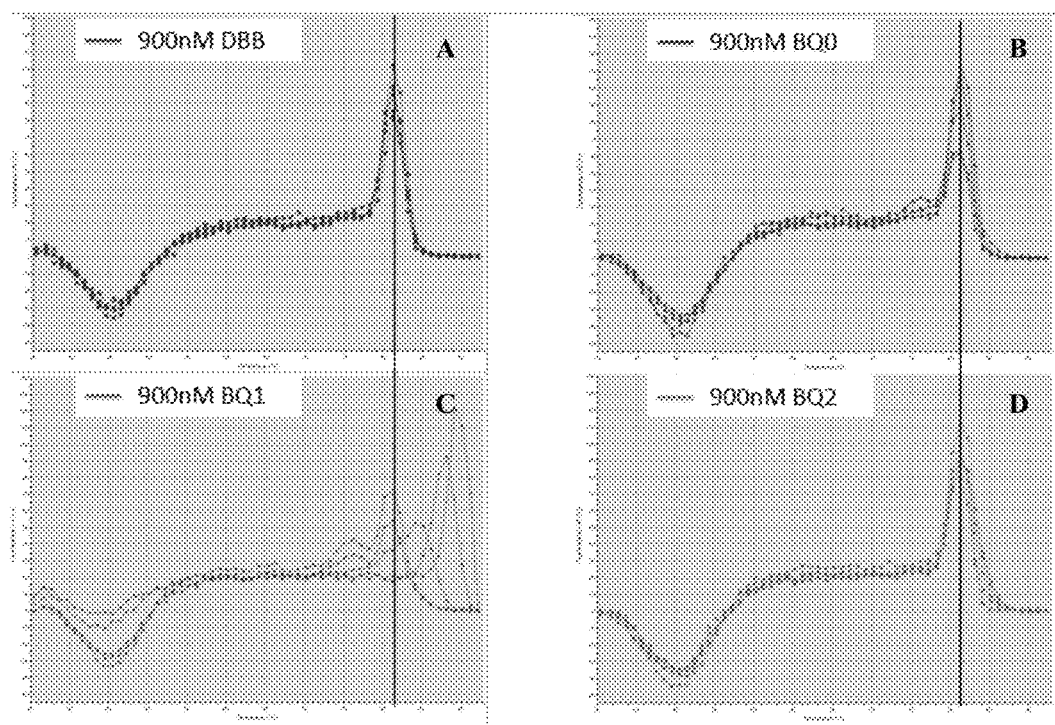
FIG. 37 shows the mispriming suppression activity of 900 nM TSDBB in reactions with target DNA compared to reactions containing equivalent concentrations of each of the TSDBB derivatives shown in FIG. 36.

FIG. 37 depicts several mispriming prevention reagents derived from TSDBB that contain one of several Black Hole Quencher moieties from Biosearch Technologies, Inc, Petaluma, Calif. instead of a dabcyl moiety. FIG. 37 illustrates the mispriming suppression activity of 900 nM TSDBB in reactions with target DNA compared to reactions containing equivalent concentrations of each of the TSDBB derivatives shown in FIG. 36. The results are displayed as melting peaks with individual lines corresponding to replicate reactions. In the presence of 900 nM TSDBB, all replicates generated a single melting peak of similar height corresponding to the intended product (FIG. 37 panel A). In contrast, in the presence of 900 nM TSDBB derivatives containing either Black Hole Quencher 0 or Black Hole Quencher 1 instead of dabcyl, replicate reactions generated either melting peaks of different heights with an additional minor peak corresponding to non-specific products (Black Hole Quencher 0, FIG. 37 panel B) or generated a variety of amplified products with different melting temperatures, most of which were too high to be the intended product (Black Hole Quencher 1, FIG. 37 panel C). Only replicate amplification reactions carried out in the presence of 900 nM TSDBB derivative containing Black Hole Quencher 2 generated a single melting peak of equivalent height similar to the replicate melting peaks obtained with TSDBB (FIG. 37 panel D).

Example 13

Figure 38:
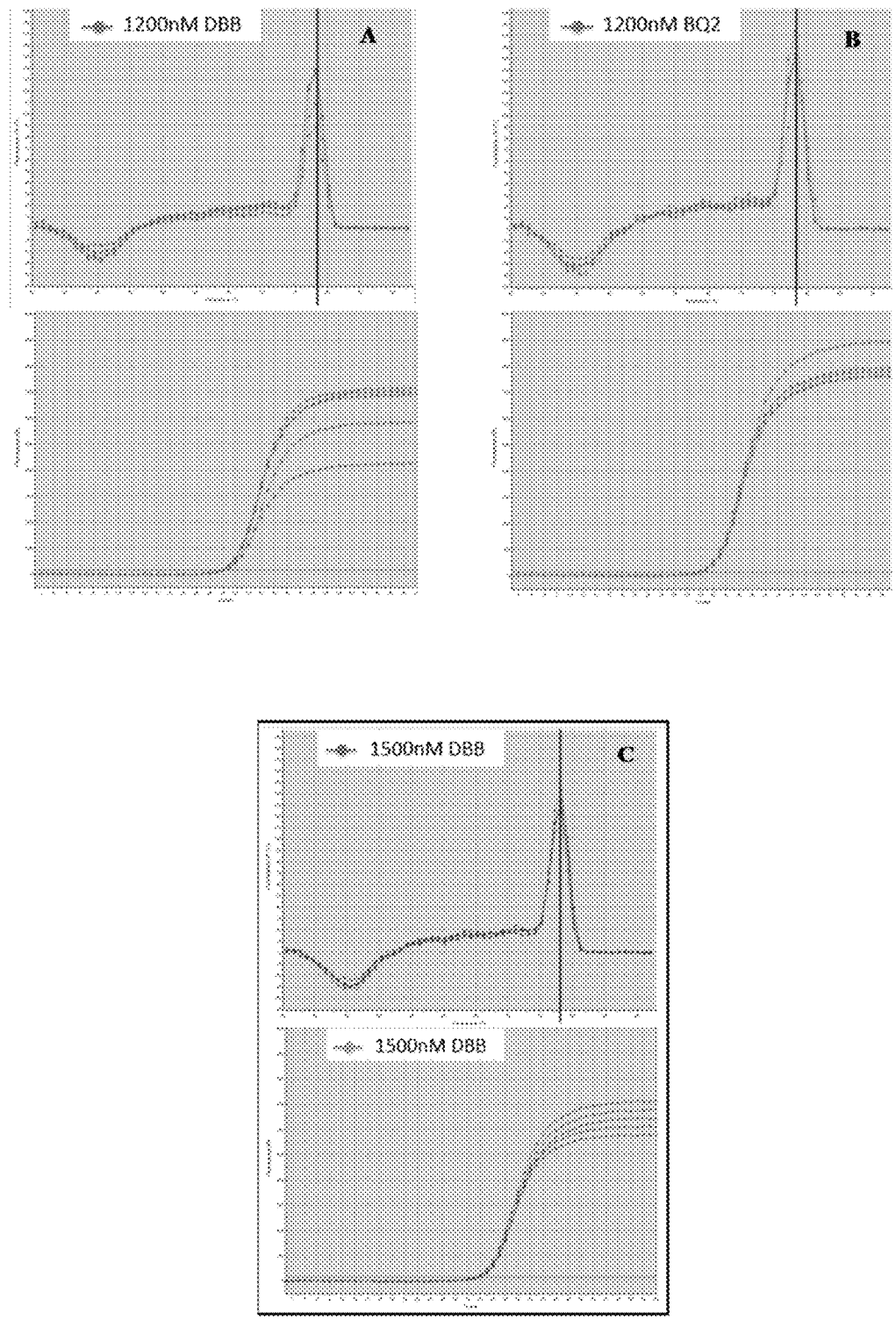
FIG. 38 shows the capacity of various concentrations of TSDBB and TSBQ2BB to suppress mispriming.

Exemplary Reagents with a Terminal 5' Black Hole Quencher 2 Moiety and a 3' Biosearch Blue Moiety FIG. 38 panel B illustrates the capacity of various concentrations of TSDBB and TSBQ2BB to suppress mispriming using an assay different from the one shown in FIG. 37. Each set of replicate reactions contained a DNA target and a constant amount of Taq DNA polymerase (1.5 units). For this particular assay, 1200 nM TSDBB was insufficient to fully suppress mispriming, as evidenced by differences in the height of the single melting peak corresponding to the intended product among replicates (FIG. 38 panel A, upper panel) as well as by differences in the kinetics of amplification among replicate reactions (scatter among the threshold cycle (Ct) values, scatter in plateau values, FIG. 38 panel A, lower panel). In the presence of the same concentration of TSBQ2BB, however, all replicate reactions exhibited a single amplicon peak of the same height with the expected Tm (FIG. 38 panel B, upper panel) and reproducible kinetics of amplification with a tighter distribution of Ct values and higher and more reproducible plateau values (FIG. 38 panel B, lower panel). These results indicate that 1200 nM suppressed all mispriming in replicate reactions and that TSBQ2BB has a higher affinity for Taq DNA polymerase compared to TSDBB. Raising the concentration of TSDBB to 1500 nM generated reproducible melting peaks similar to those observed with 1200 nM TSBQ2BB (FIG. 38 panel C, upper panel). Although the kinetics of amplifications observed in the presence of 1500 nM TSDBB were much tighter that those obtained with 1200 nM TSBB, however, the amplification curves did not match the reproducibility and higher plateau values (i.e., higher amplicon yield) obtained in the presence of 1200 nM TSBQ2BB (FIG. 38 panel C, lower panel). Given that the capacity of the reagents to suppress one or more aspects of mispriming is reflected in the enhanced amplification of the intended products, these results demonstrate TSBQ2BB exhibits improved mispriming suppression activity compared to TSDBB in addition to having higher affinity for Taq DNA polymerase.

Example 14

Figure 39:
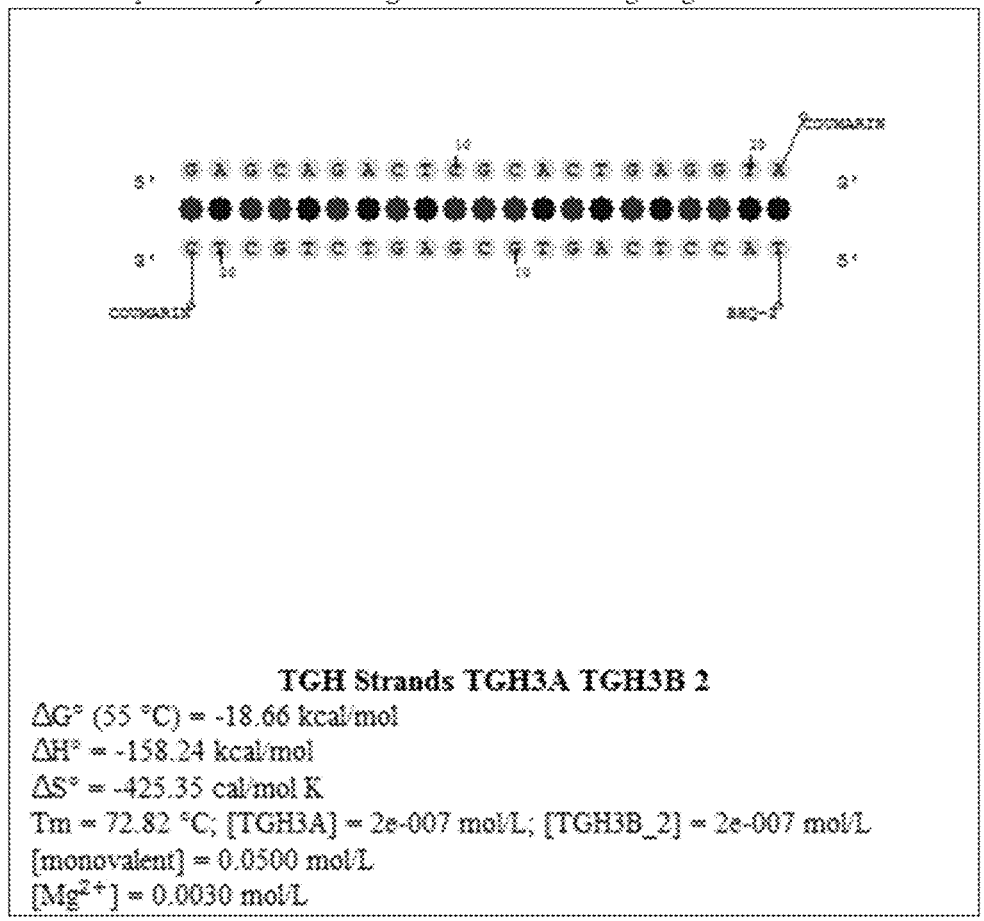
FIG. 39 is a multi-panel figure depicting information regarding an exemplary multi-stranded mispriming prevention reagent. Panel (A) shows the structure and sequence of an exemplary multi-stranded mispriming prevention reagent. Figure discloses SEQ ID NOS 46-49, respectively, in order of appearance. Panels (B-E) show symmetric monoplex amplification of the human gene BRCA1, without an exemplary multi-stranded mispriming prevention reagent (FIG. 39, panels B and D), and with 400 nM of an exemplary multi-stranded mispriming prevention reagent (FIG. 39 panel C and FIG. 39 panel E).
Figure 39:
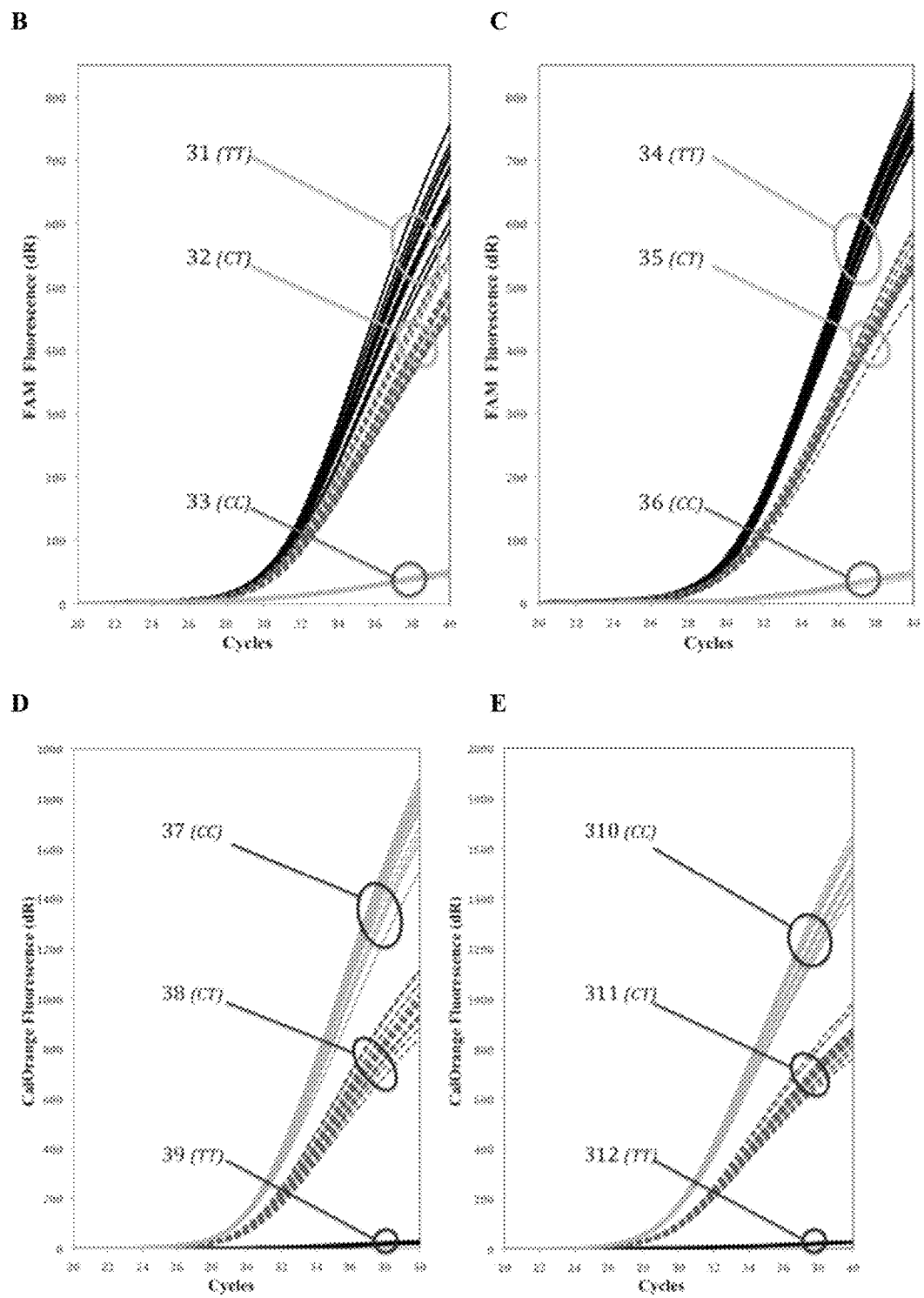

Reduction of Scatter Among Replicate Amplification Reactions by Exemplary Multi-Stranded Mispriming Prevention Reagents The ability of an exemplary multi-stranded mispriming prevention reagent (structure and sequence provided in FIG. 39 panel A) to reduce scatter among replicate amplification reactions was tested. A symmetric monoplex amplification of the human gene BRCA1 was performed either without a multi-stranded mispriming prevention reagent (FIG. 39 panel B and 39 panel E) or with 400 nM of a multi-stranded mispriming prevention reagent (FIG. 39 panel C and FIG. 39 panel E). FIG. 39 panel B and 39 panel C show fluorescence detected from FAM labeled TaqMan probes. FIG. 39 panel D and 39 panel E show the same samples as FIG. 39 panel B and 39 panel C respectively, but with fluorescence detected from Cal Fluor Orange 560 labeled TaqMan probes. Each panel includes replicate reactions of three different DNA samples whose BRCA1 genes differ at a single nucleotide polymorphism. The solid black lines (31, 34, 39, 312) indicate homozygous TT samples, the dotted grey lines (32, 35, 38, 311) indicate heterozygous TC samples, and the solid grey lines (33, 36, 37, 310) indicate homozygous CC samples. This experiment was performed with 1× Klearkall Hot-start Mastermix prepared from a 2×stock provided by the manufacturer (LCG Biosearch), using about one thousand copies per microliter of human DNA from Coriell Cell Repositories as a target. The thermocycling profile used was: fifteen minutes at 95° C., followed by sixty cycles of 95° C. for twenty seconds and 60° C. for one minute.

FIG. 40 panel A depicts a box and whisker plot generated from the end-point data depicted in FIGS. 39 panel B and 39 panel C The box and whisker plot in FIG. 40 panel B was generated from the end-point data depicted in FIGS. 39 panel D and 39 panel E. Data sets 41, 44, 49, & 412 represent end-point data from samples with the BRCA1 genotype CC. Data sets 42, 45, 48, & 411 represent end-point data from samples with the BRCA1 genotype TC. Data sets 43, 46, 47 and 410 represent end-point data from samples with the BRCA1 genotype TT. The line in the center of each box represents the median of that data set. The box represents interquartile region, or the $25^{th}$ to $75^{th}$ percentile of the data set. The upper whisker represent the $95^{th}$ percentile of the data set and the lower whisker represents the $10^{th}$ percentile. Addition of a multi-stranded mispriming prevention reagent (44-46 and 410-412) compared to the control (41-43 and 47-49) decreases the interquartile regions of data from each genotype, demonstrating a reduction in endpoint scatter among replicate reactions. Addition of a multi-stranded mispriming prevention reagent (44-46 and 410-412) also increases the difference between each genotypic group, separating the whiskers or the outer edges of each group of replicates more than in the control (41-43 and 47-49).

Figure 43:
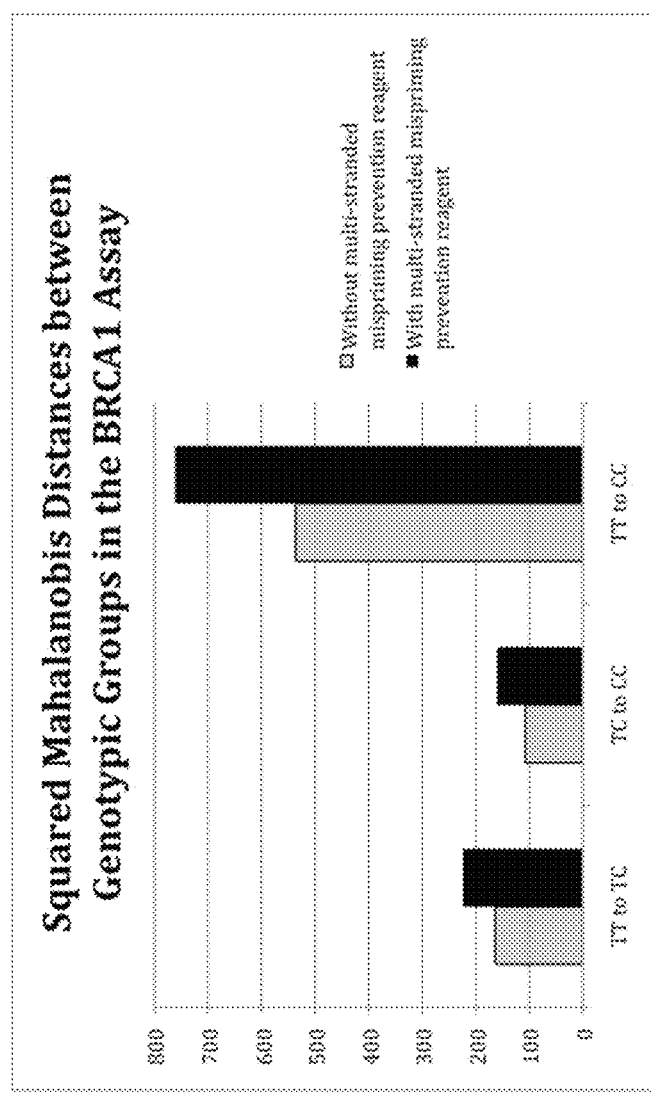
FIG. 43 shows a bar graph of statistical distances between genotypic groups in data sets from FIG. 39 panels B-E.

FIG. 41 shows scatter plots of end-point data from FIG. 39 panels B-E with 95% confidence ellipses around each group of replicates. The vertical axis is fluorescence detected by Cal Fluor Orange 560 labeled probes, the horizontal axis is fluorescence detected by FAM labeled probes. This XY scatter plot format is especially relevant for evaluating SNP (single nucleotide polymorphism) genotyping assays because this format is a common basis for algorithms that use fluorescence from two probes to determine genotype. Gray points indicate reactions without multi-stranded mispriming prevention reagent, Black points indicate reactions with 400 nM of multi-stranded mispriming prevention reagent. The two groups of replicates labeled "51" have the BRCA1 genotype CC. The two groups of replicates labeled "52" have the BRCA1 genotype CT or TC. The two groups of replicates labeled "53" have the BRCA1 genotype TT. FIG. 41 panel B is an enlarged view of the heterozygous groups of replicates labeled "52" in FIG. 41 panel A. Ellipses were created with the user written program "Ellip" for Stata12. These results demonstrate that the addition of multi-stranded mispriming prevention reagent reduces scatter among replicates in two dimensions of measured fluorescence and increases the ability to distinguish between genotypes. The increased separation between genotypic groups can be verified mathematically by calculating the squared Mahalanobis distance between groups (FIGS. 42 & 43). The squared Mahalanobis distance is a unitless metric that accounts for the average Euclidean distance between groups, variance in both the CalOrange and FAM fluorescence and the covariance between probe readings.

Squared Mahalanobis distance can be calculated between two genotypic groups $X_1$ and $X_2$ with the following formula, where S is the variance covariance matrix for FAM and CalOrange fluorescence:

$$D^2=(\overline{X}_2-\overline{X}_1)'S^{-1}(\overline{X}_2-\overline{X}_1)$$

The more distinct two groups are from each other, the higher the Mahalanobis distance between them. The large F values and small p values associated with the squared Mahalanobis distances listed in the table in FIG. 42 verify that the increased distance between genotypic groups with an exemplary multi-stranded mispriming prevention reagent is statistically significant.

Example 15

Figure 44:
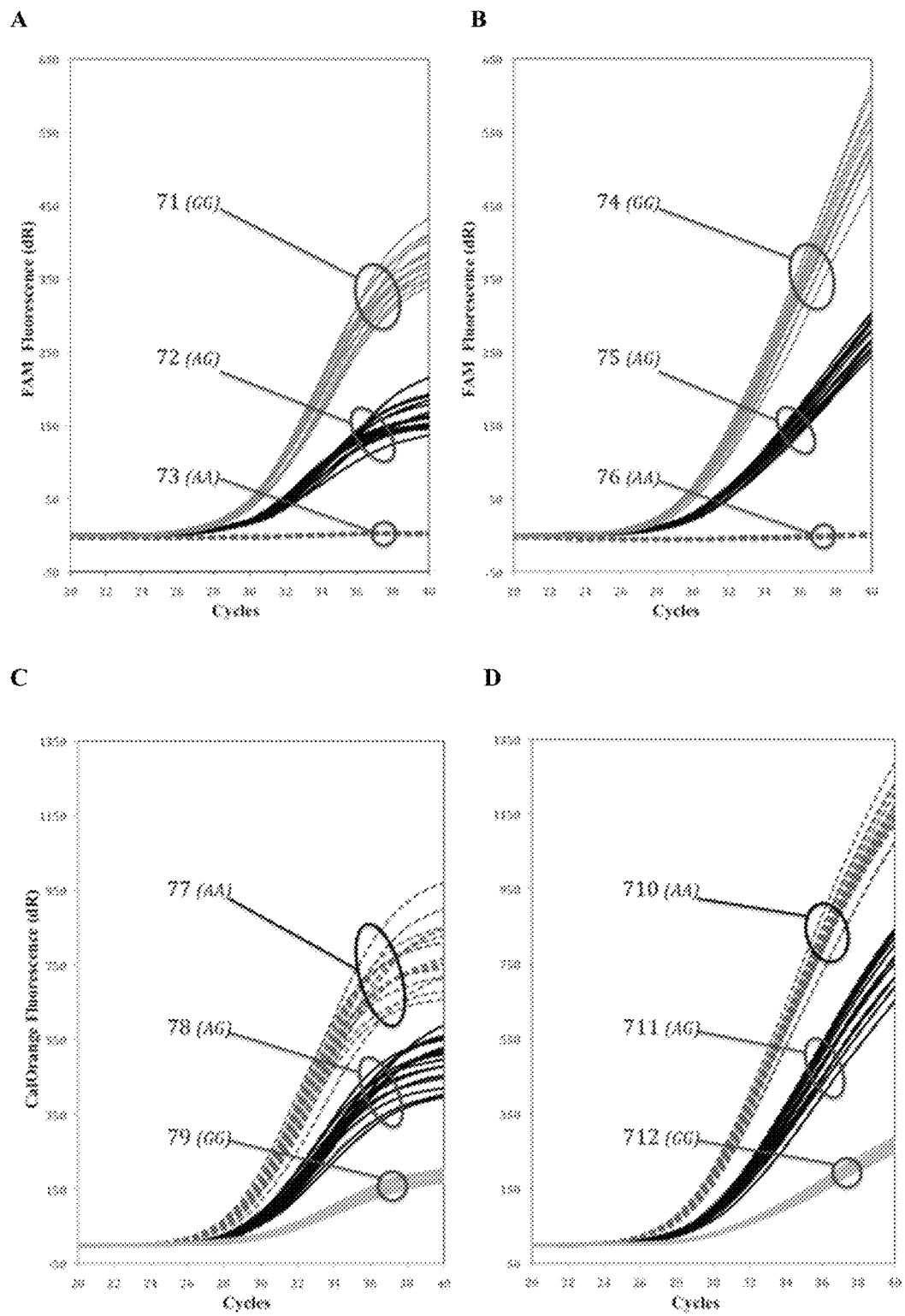
FIG. 44 shows symmetric amplification of the human gene XRCC1 with 400 nM of an exemplary multi-stranded mispriming prevention reagent (FIG. 44 panel B and FIG. 44 panel D) and without an exemplary multi-stranded mispriming prevention reagent (FIG. 44 panel A and 44 panel C)

Increase of Fluorescent Signal in Amplification Reactions by Exemplary Multi-Stranded Mispriming Prevention Reagents The effect of an exemplary multi-stranded mispriming prevention reagent (depicted in FIG. 39 panel A) on the fluorescent signal produced in a nucleic acid amplification reaction was tested. As depicted in FIG. 44, symmetric amplification of the human gene XRCC1 was performed with 400 nM multi-stranded mispriming prevention reagent (FIG. 44 panel B and FIG. 44 panel D) or without multi-stranded mispriming prevention reagent (FIGS. 44 panel A and 44 panel C). TaqMan probes were used to detect formation of amplification product. FIG. 44 panels A and B show fluorescence from FAM labeled probes. FIG. 44 panels C and D show the same samples as FIGS. 44 panel A and 44 panel B respectively, but with fluorescence detected from Cal Fluor Orange. 560 labelled probes. Each panel includes replicate reactions of three different DNA samples whose XRCC1 genes differ by a single nucleotide polymorphism. The solid black lines (72, 75, 78, 711) indicate heterozygous GA or AG samples, the dotted grey lines (73, 76, 77, 710) indicate homozygous AA samples, and the solid grey lines (71, 74, 79, 712) indicate homozygous GG samples. This experiment was performed with 1× Klearkall Hot-start Mastermix, used according to the manufacturer's instructions using about one thousand copies per microliter of human DNA from Coriell Cell Repositories as a target. The thermocycling profile used was: fifteen minutes at 95° C., followed by sixty cycles of 95° C. for twenty seconds and 60° C. for one minute.

The box and whisker plot in FIG. 45 panel A was generated from the end-point data from FIG. 44 panels A and B. The box and whisker plot in FIG. 45 panel B was generated from the end-point data from FIG. 44 panels C and D. Data sets 81, 84, 87, & 810 represent end-point data from samples with the BRCA1 genotype GG. Data sets 82, 85, 88, & 811 represent end-point data from samples with the BRCA1 genotype AG or GA. Data sets 83, 86, 89, & 812 represent end-point data from samples with the BRCA1 genotype AA. The line in the center of each box represents the median of that data set. The box represents the interquartile region, or the $25^{th}$ to $75^{th}$ percentile of the data. The upper whisker represent the $95^{th}$ percentile of the data set and the lower whisker represents the $10^{th}$ percentile.

Figure 46:
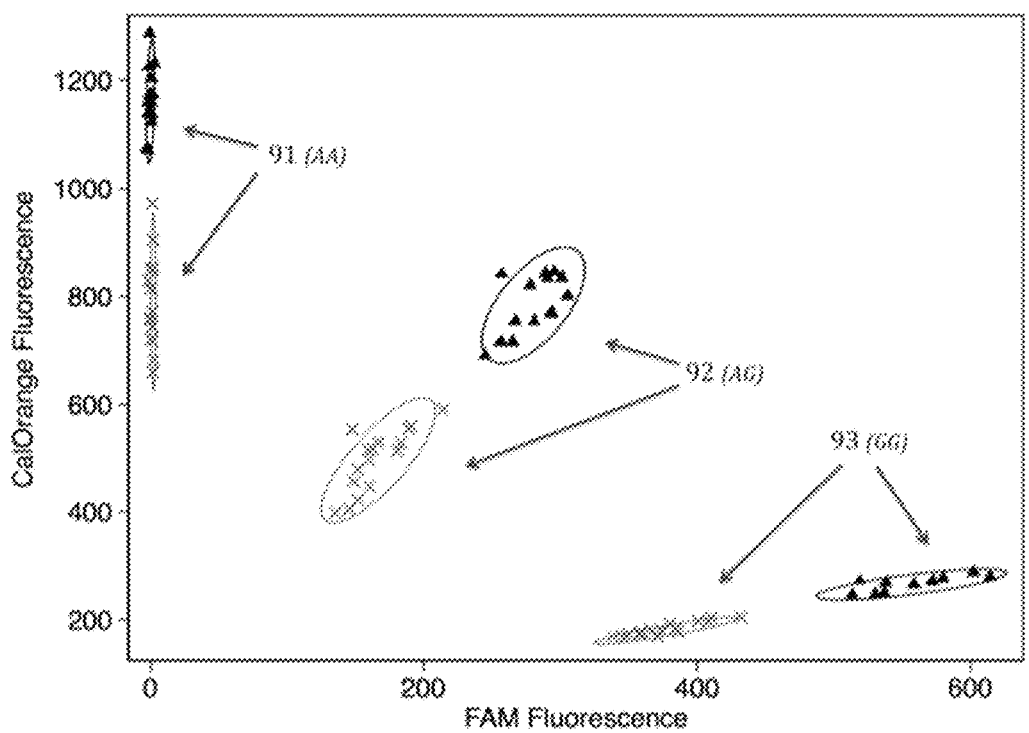
FIG. 46 shows a scatter plot of endpoint data from FIG. 44 with 95% confidence ellipses. The vertical axis is fluorescence detected from probes labeled with Cal Fluor Orange 560. The horizontal axis is fluorescence detected from probes labeled with FAM. Gray points indicate reactions without an exemplary multi-stranded mispriming prevention reagent, Black points indicate reactions with 400 nM of an exemplary multi-stranded mispriming prevention reagent.
Figure 47:
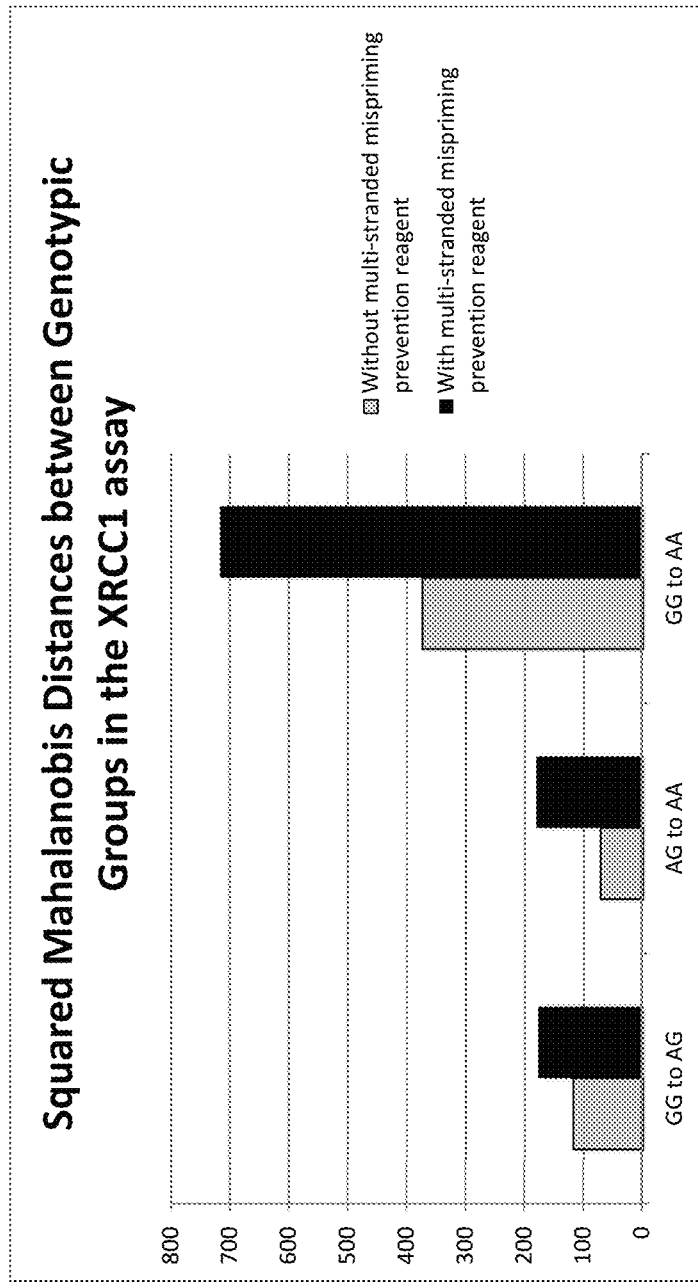
FIG. 47 shows a table (47 panel A) and bar graph (47 panel B) of statistical distances between genotypic groups in data sets from FIG. 46.

These box and whisker plots demonstrate that for each of the fluorescence measurements with FAM labeled probes and Cal Fluor Orange 560 labelled probes, the addition of multi-stranded mispriming prevention reagent (84-86 and 810-812) reduces variation between replicates, increases specific product yield, and increases the difference between genotypes compared to control (81-83 and 87-89). This is reiterated in two-dimensions by the XY scatter plot of the data (FIG. 46) and mathematically by the squared Mahalanobis distance metric (FIG. 47 panels A and B).

Example 16

Addition of Exemplary Multi-Stranded Mispriming Prevention Reagent Changes Amplification Curve Shape As shown in FIG. 44, adding a multi-stranded mispriming prevention reagent not only increases specific product yield, but also changes the shape of amplification plots. Reactions without multi-stranded mispriming prevention reagent (FIG. 44 panels A and C) slow down and plateau earlier. Reactions with multi-stranded mispriming prevention reagent (FIG. 44 panel B and D) appear linear through 40 cycles, suggesting that multi-stranded mispriming prevention reagent suppresses non-specific products which otherwise occupy the enzyme and/or use up primers, halting the reaction. As KlearKall chemical hot-start used in this reaction it is likely that the non-specific products being prevented by multi-stranded mispriming prevention reagent originate during amplification.

Figure 48:
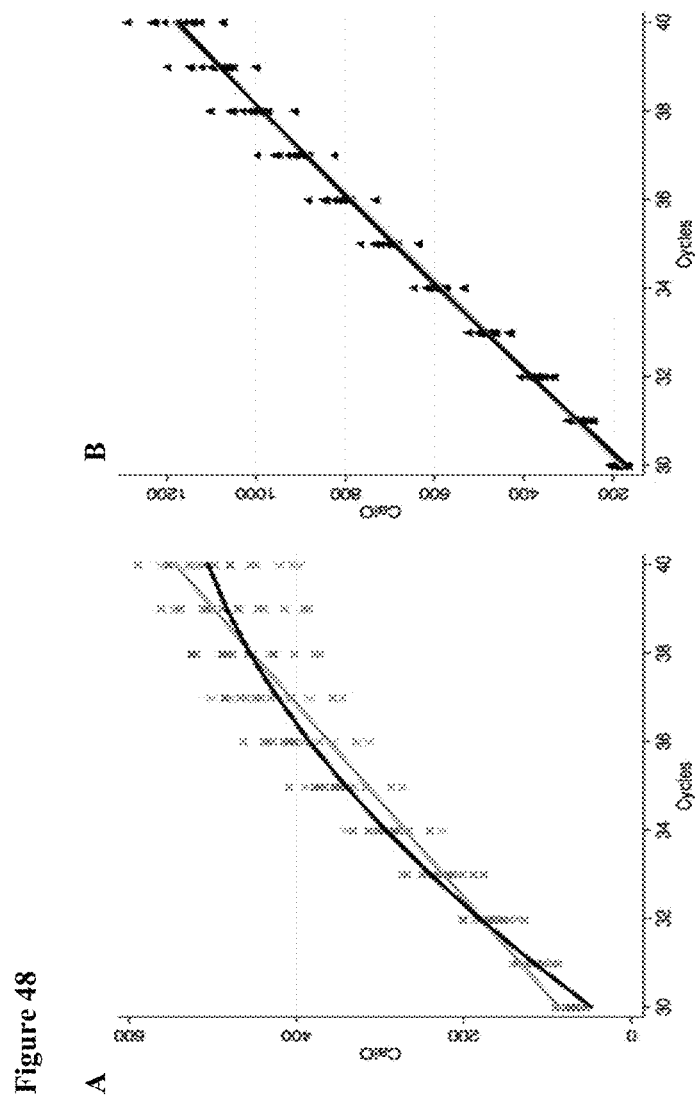
FIG. 48 is a multi-panel figure in which panels A and B show data points from lines 77 and 710 of FIG. 46 panels C and D compared with linear and quadratic lines of best fit and panel C shows a table of linear and quadratic regression analyses of data sets 77 and 710 in FIG. 46.

The change in amplification plot shape can be measured mathematically with linear and quadratic regression analysis. FIG. 48 panels A and B show data points from lines 77 and 710 in FIG. 44 panels C and D, respectively, with their linear line of best fit superimposed in grey, and their quadratic line of best fit superimposed in black. The lines represent the ordinary least squared regression of fluorescence against cycles and, for the quadratic curve, cycles-squared, which minimizes the sum of the squared deviations between the points and line. Comparing the lines of best fit to the spread of data points at each cycle reveals which model, quadratic or linear, more accurately represents the data. Neither model attempts to explain the convex exponential curve at the beginning of reactions (i.e. prior to cycle 30), so this comparison evaluates concave curvature towards the end of amplification. FIG. 48 panel A shows that the reactions without an exemplary multi-stranded mispriming prevention reagent are better represented by the quadratic model because the quadratic best fitting line (grey) passes near the center of the replicates at more cycles than the linear best fitting line (black). FIG. 48 panel B shows that reactions with an exemplary multi-stranded mispriming prevention reagent are better represented by the linear model because the quadratic best fitting line (grey) line appears almost identical to the linear best fitting line (black), indicating that a quadratic term does not improve the linear model and the linear model is accurate.

The table in FIG. 48 panel C gives the statistical results corresponding to the fitted lines in FIG. 48 panels A and B. Columns (1)-(3) present results when fluorescence is explained only by the number of cycles. Columns (4)-(6) present results on the quadratic term and the overall R-squared when fluorescence is explained by both the number of cycles and the number of cycles squared.

The linear regression R-squared values in column (3) indicate that the exemplary multi-stranded mispriming prevention reagent increases the "linearity" of amplification curves because the best fitting straight line explains only 91.0% of the variation among replicates without the reagent versus 98.55% of the variation among replicates with reagent. The slope of the amplification curves, as measured by the linear coefficients in column (1), is 2.2 times larger in the presence of the exemplary multi-stranded mispriming prevention reagent. This indicates that the exemplary multi-stranded mispriming prevention reagent increases the rate of the rate of amplification.

Comparing R-squared values in column (6) to column (3), the addition of the quadratic term substantially improves the fit to the data in FIG. 48 panel A, reducing the proportion of unexplained variance from 0.090 to 0.067, or by 22%. Addition of the quadratic term only slightly improves the fit to the data in FIG. 48 panel B (reducing unexplained variance from 0.0145 to 0.0141, or by less than 1%.

The decreased curvature in reactions with an exemplary multi-stranded mispriming prevention reagent (FIG. 48 panel B) compared to reactions without (FIG. 48 panel A) can also be measured by the decreased magnitude of the estimated coefficient of the quadratic terms (−2.61 compared to −0.789 in column (4)) and the decreased magnitude of their statistical significance (7.75 to 2.34 in column (5)

In sum, the exemplary multi-stranded mispriming prevention reagent changes the slope and shape of amplification plots from a slowly rising quadratic curve with an early plateau to a rapidly rising linear function that does not plateau in the same number of cycles. This demonstrates that the exemplary multi-stranded mispriming prevention reagent affects the kinetics of primer dependent amplification, increasing the rate of amplification and delaying it from slowing down.

Example 17

Figure 49:
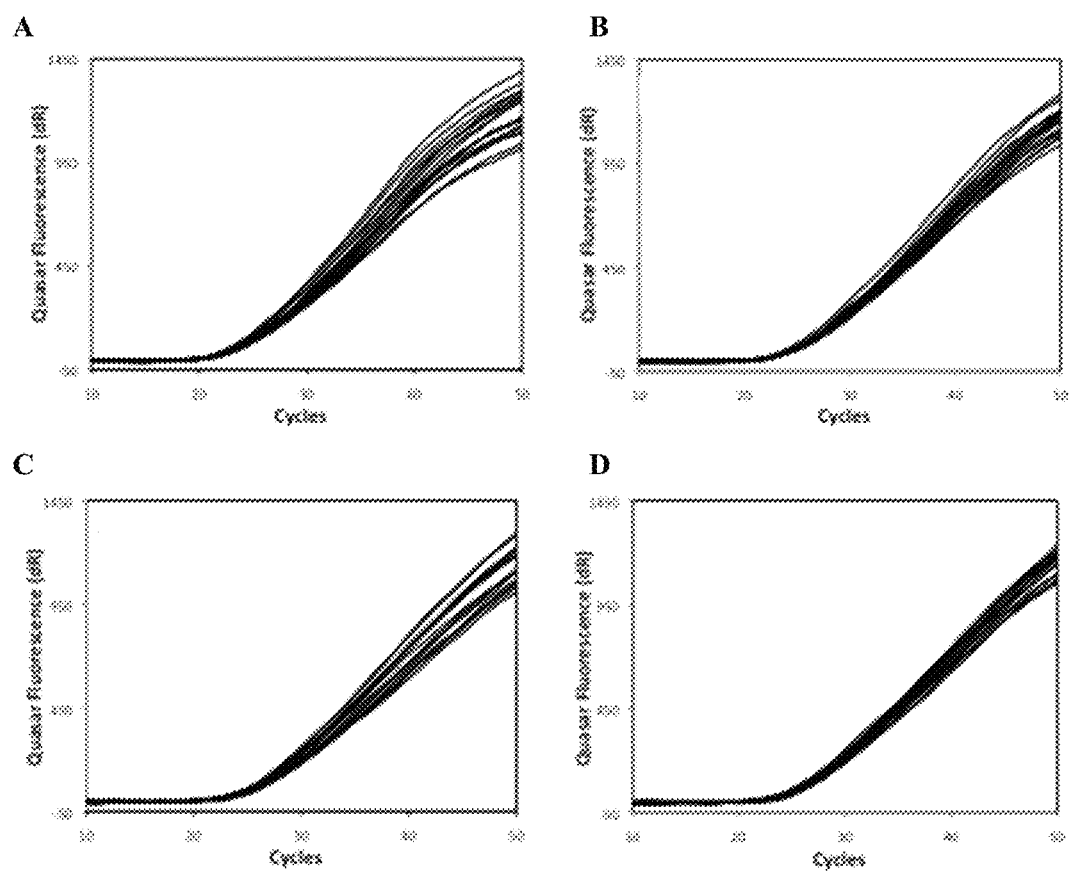
FIG. 49 shows symmetric amplification of human DNA probed with two molecular beacons for a four base pair insertion associated with Tay-Sachs Disease. The first four panels (A-D) show fluorescence measured from Quasar Fluor 670 labeled probes, the second four panels (E-H) show fluorescence measured from Cal Flor Red 610 labeled probes.
Figure 49:
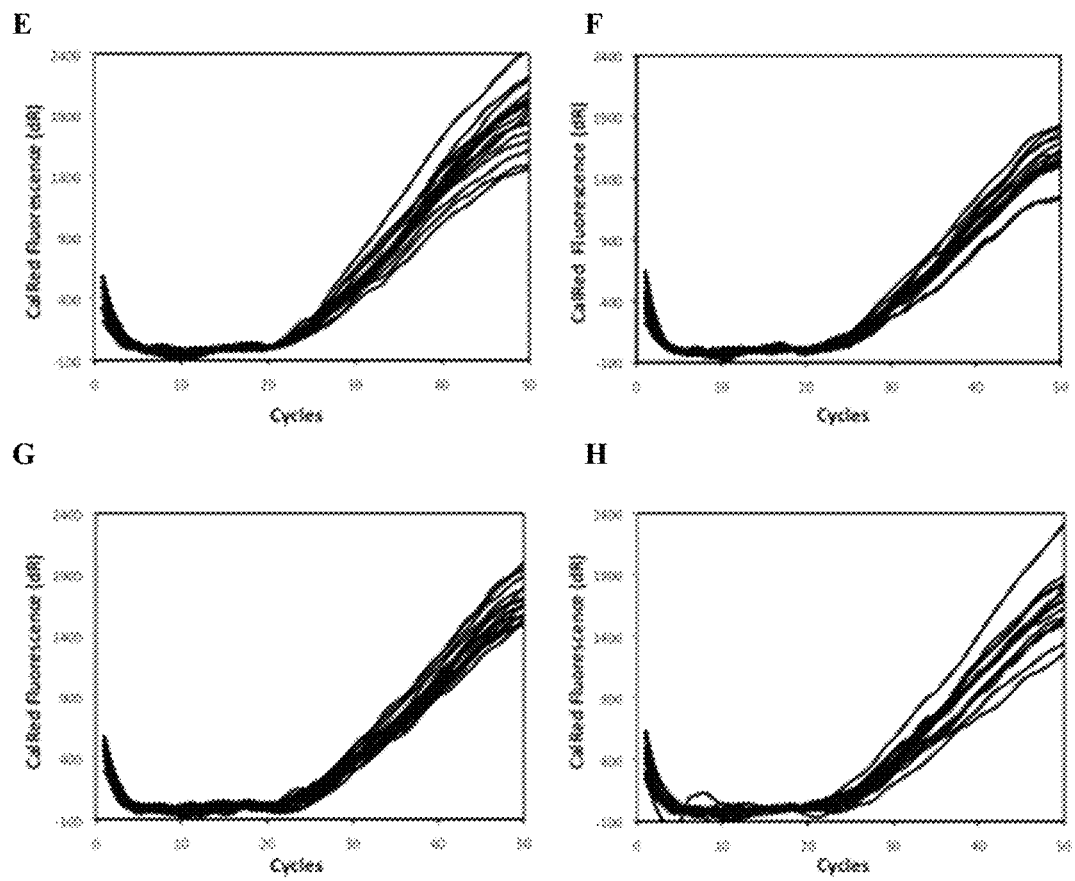

Concentration Dependent Reduction of Amplification Reaction Scatter by Exemplary Multi-Stranded Mispriming Prevention Reagents Optimization of multi-stranded mispriming prevention reagent concentration was demonstrated. Symmetric amplification of human DNA probed with two molecular beacons for a four base pair insertion (+TATC) at position 1278 in the hexosaminidase A gene associated with Tay-Sachs Disease was performed with 1× Klearkall Hot-start Mastermix used according to manufacturer's instructions. The thermocycling profile used was: fifteen minutes at 95° C., followed by ten cycles of 95° C. for ten seconds, 62° C. for thirty seconds, 72° C. for fifteen seconds, and then fifty cycles of 95° C. for one minute, 55° C. for thirty seconds, 72° C. for thirty seconds. FIG. 49 panels A to D show fluorescence measured from Quasar Fluor 670 labelled probes, while FIG. 49 panels E-H show fluorescence measured from Cal Fluor Red 610 labeled probes. Increasing the concentration of multi-stranded mispriming prevention reagent from 0 nM (FIG. 49 panels A and E), to 200 nM (FIG. 49 panels B and F), 300 nM (FIGS. 49C and 49G) and 400 nM (FIGS. 49D and 49H) shows optimal scatter reduction to be different for each probe. Maximum scatter reduction was measured in Quasar 670 fluorescence with 400 nM multi-stranded mispriming prevention reagent, whereas maximum scatter reduction was measured in the Cal Fluor Red 610 fluorescence with 300 nM multi-stranded mispriming prevention reagent.

Example 18

Structural Features of Exemplary Multi-Stranded Mispriming Prevention Reagents

Figure 50:
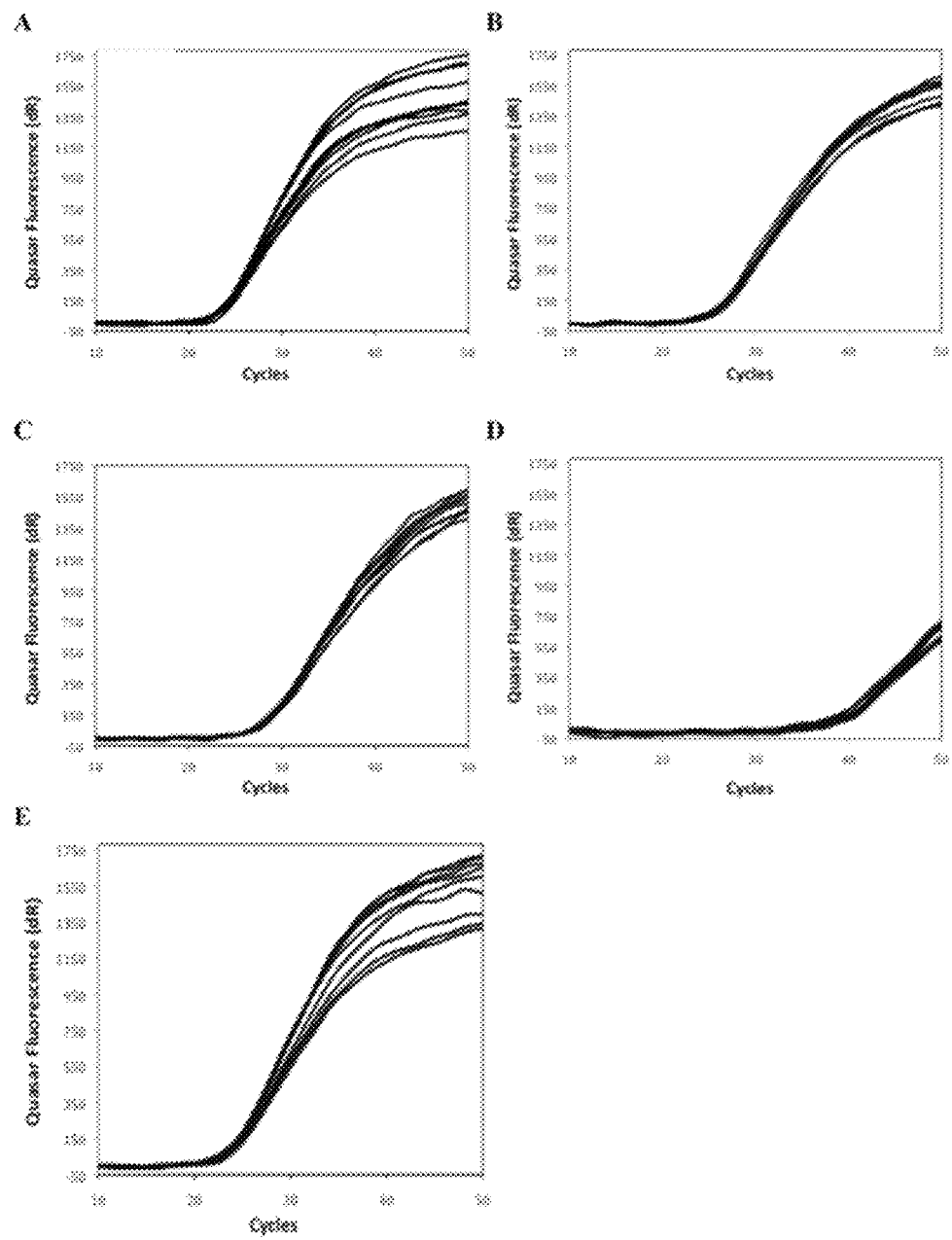
FIG. 50 shows symmetric amplification of human DNA probed with two molecular beacons for a four base pair insertion associated with Tay-Sachs Disease using GoTaq Flexi Polymerase without any exemplary mispriming prevention reagent (FIG. 50 panel A), with 50 nM of an exemplary multi-stranded mispriming prevention reagent (FIG. 50 panel B), with 100 nM of an exemplary multi-stranded mispriming prevention reagent (FIG. 50 panel C), with 300 nM of an exemplary multi-stranded mispriming prevention reagent (FIG. 50 panel D) and with 300 nM of the oligonucleotides of the multi-stranded exemplary reagent having no modifying moieties (FIG. 50 panel E).
Figure 51:
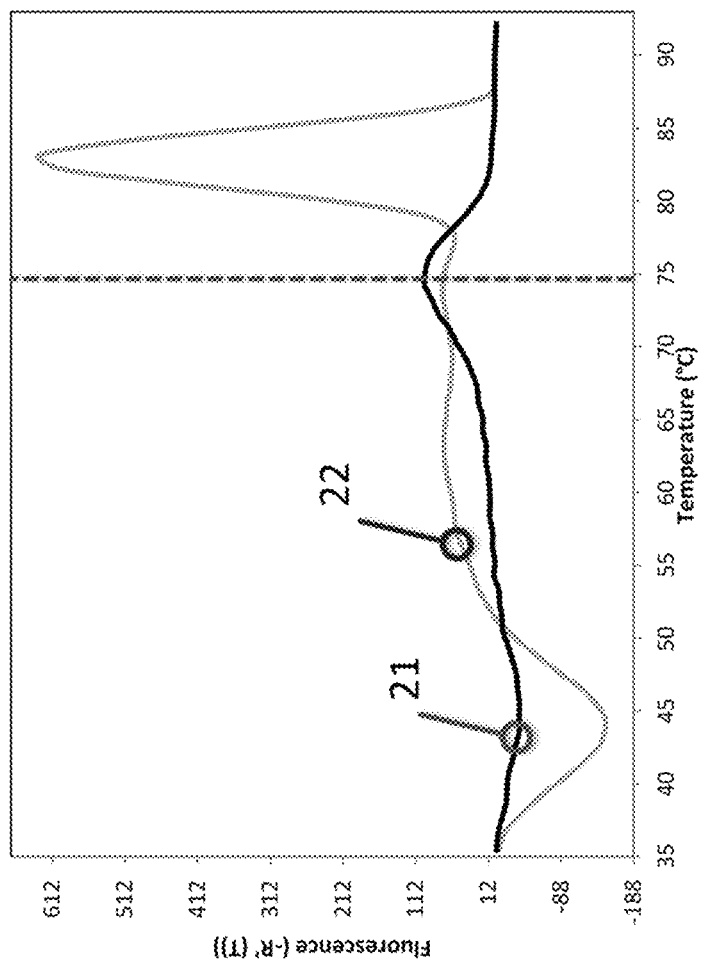
FIG. 51 shows a SYBR Green melting analysis of the $T_m$ of an exemplary multi-stranded mispriming prevention reagent.

In FIGS. 50, 51 and 52, the same assay as depicted in FIG. 49 is used to demonstrate three structural features of the exemplary multi-stranded mispriming prevention reagent.

FIG. 50 shows the effect of various concentrations of multi-stranded mispriming prevention reagent on a different polymerase. A concentration of 50 nM (FIG. 50 panel B), 100 nM (FIG. 50 panel C) and 300 nM (FIG. 50 panel D) multi-stranded mispriming prevention reagent was applied to GoTaq Flexi Polymerase in the presence of 1200 nM single-stranded mispriming prevention reagent to reduce scatter. These reactions were performed in the presence of 3 mM MgCl2, 250 µM dNTPs, and 1× GoTaq Flexi Buffer. The thermocycling profile used was: three minutes at 95° C., followed by ten cycles of 95° C. for ten seconds, 62° C. for thirty seconds, 72° C. for fifteen seconds, and then fifty cycles of 95° C. for one minute, 55° C. for thirty seconds, 72° C. for thirty seconds. Fluorescence was measured from Quasar Fluor 670 labeled probes. FIG. 50 also demonstrates the difference between adding 300 nM multi-stranded mispriming prevention reagent with the terminal modifiers depicted in FIG. 39 panel A (FIG. 50 panel D) and adding 300 nM of the same oligonucleotides without any terminal modifications (FIG. 50 panel E). Chi squared tests for significant change in end point in variation shown in the table in FIG. 50 panel F demonstrates that while even 50 nM of the exemplary single-stranded mispriming prevention reagent is sufficient to significantly reduce scatter, 300 nM of the same oligonucleotides without terminal modifications does not significantly reduce scatter.

FIG. 51 shows a SYBR melt curve analysis with 100 nM of the exemplary multi-stranded mispriming prevention reagent (line 22) and with 500 nM of the exemplary multi-stranded mispriming prevention reagent (line 21). Both conditions were run with about 1000 copies of genomic DNA but only the samples containing 100 nM exemplary multi-stranded mispriming prevention reagent amplified after 60 cycles, indicating that 500 nM of the exemplary multi-stranded reagent was inhibitory for a reaction with only 1.5 units of Promega GoTaq Flexi polymerase. This inhibitory concentration is useful for finding the Tm of the exemplary single-stranded mispriming prevention reagent.

Melt curve 22 shows a specific product peak at about 83° C., and a valley at about 44° C. indicating the presence of 1200 nM of the exemplary single-stranded mispriming prevention reagent TSBQ2BB. Melt curve 21 does not show an obvious SYBR signature from the same amount of TSBQ2BB because not enough specific product was generated for a valley, and the additional 500 nM multi-stranded mispriming prevention reagent spreads out the SYBR dye bound at low temperatures, preventing it from outshining local Black Hole Quenchers. Melt curve 21 does not show a specific product peak, but instead has a hill at 75° C. because not enough product was made to outcompete the 500 nM of exemplary multi-stranded mispriming prevention reagent binding SYBR dye and the single Black Hole Quencher on the exemplary multi-stranded mispriming prevention reagent did not completely quench the SYBR bound to it. Therefore the peak of the hill provides the empirical $T_m$ of the exemplary single-stranded mispriming prevention reagent to be about 75° C.

The table in FIG. 52 demonstrates the importance of the multi-stranded character of the exemplary mispriming prevention reagent. FIG. 50 showed that even 50 nM of the multi-stranded mispriming prevention reagent, or 100 nM of each strand of the multi-stranded mispriming prevention reagent, was sufficient to significantly reduce endpoint fluorescence variation in this assay. Adding 1200 nM of either the upper or lower strand of the multi-stranded mispriming prevention reagent (sequences provided in FIG. 39 panel A) makes no significant change to the endpoint scatter.

Example 19

Figure 53:
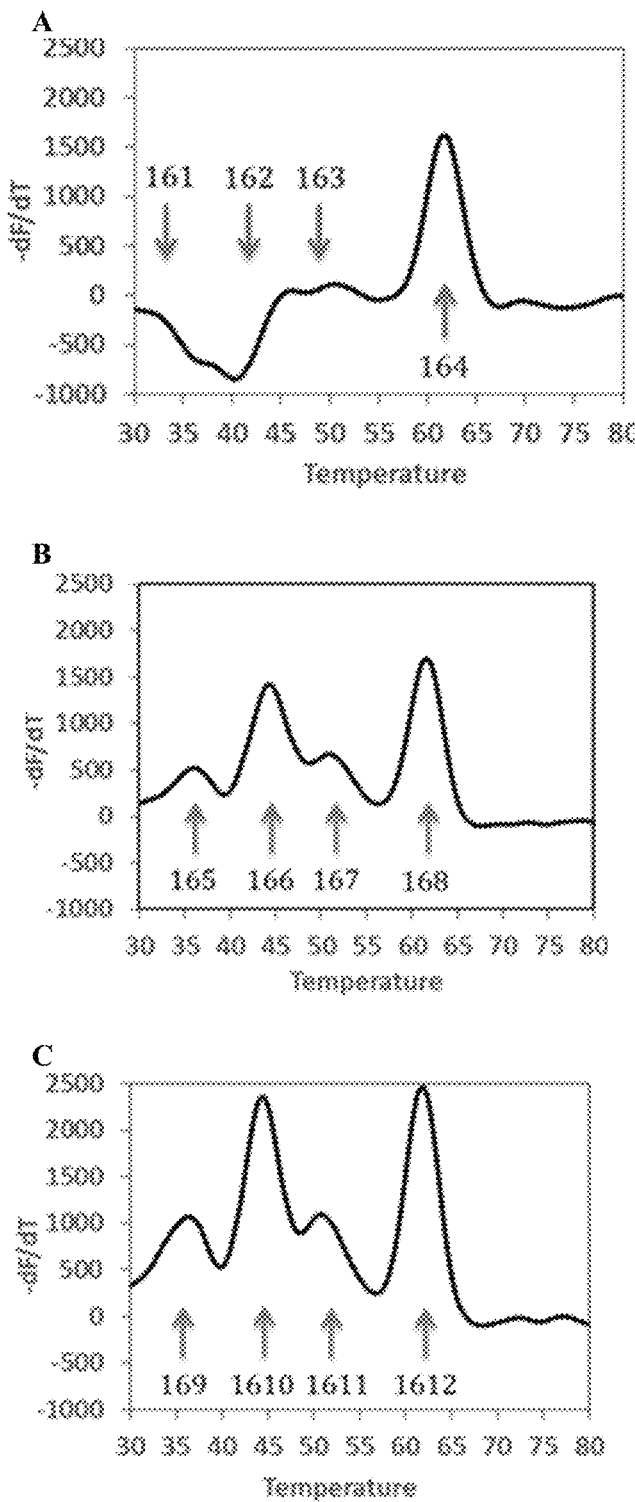
FIG. 53 shows data generated in a multiplex LATE-PCR assay for fourteen different strains of human papillomavirus. 53A without any exemplary reagent, 53B with 5 µM TSBQ2BB, 53C with 45 µM TSBQ2BB and 125 nM TG

Use of Exemplary Multi-Stranded Mispriming Prevention Reagents in Multiplex Amplification Reactions A multiplex LATE-PCR assay for fourteen different strains of Human Papillomavirus was performed (FIG. 53). All three panels of FIG. 53 are melt curve analyses of Cal Fluor Red 610 probes designed to visualize four product peaks representing different types of HPV. FIG. 53 panel A shows the multiplex run without any single-stranded mispriming prevention reagent or multi-stranded mispriming prevention reagent additions. FIG. 53 panel B shows the multiplex run with 5 µM single-stranded mispriming prevention reagent but no multi-stranded mispriming prevention reagent. FIG. 53 panel C shows the multiplex run with 5 µM single-stranded mispriming prevention reagent and 125 nM multi-stranded mispriming prevention reagent. Labels 161, 165, and 169 indicate where a product peak for HPV Type 1 is expected. Labels 162, 166, 1610 indicate where a product peak for HPV Type 2 is expected. Labels 163, 167, 1611 indicate where a product peak for HPV Type 3 is expected. Labels 164, 168, 1612 indicate a product peak for HPV Type 4. Without single-stranded mispriming prevention reagent or multi-stranded mispriming prevention reagent, only HPV Type 4 amplifies correctly to produce a visible product peak. The addition of 5 μM single-stranded mispriming prevention reagent enables all four types of HPV to become visible in the multiplex. Further addition of 125 nM multi-stranded mispriming prevention reagent increases the yield of all four types of HPV, including Type 4 which was unaffected by the addition of single-stranded mispriming prevention reagent. This figure demonstrates that multi-stranded mispriming prevention reagent adds cumulatively to the benefits of single-stranded mispriming prevention reagent and both reagents working together can maximize specific product yield. The reaction contained 5 units of hot-start Taq from Hain Lifescience. These results (see FIG. 53 panel A as compared to FIG. 53 panel B) also demonstrate that Hain Lifescience hot-start Taq is not fully inactivated by its chemical modification.

Figure 54:
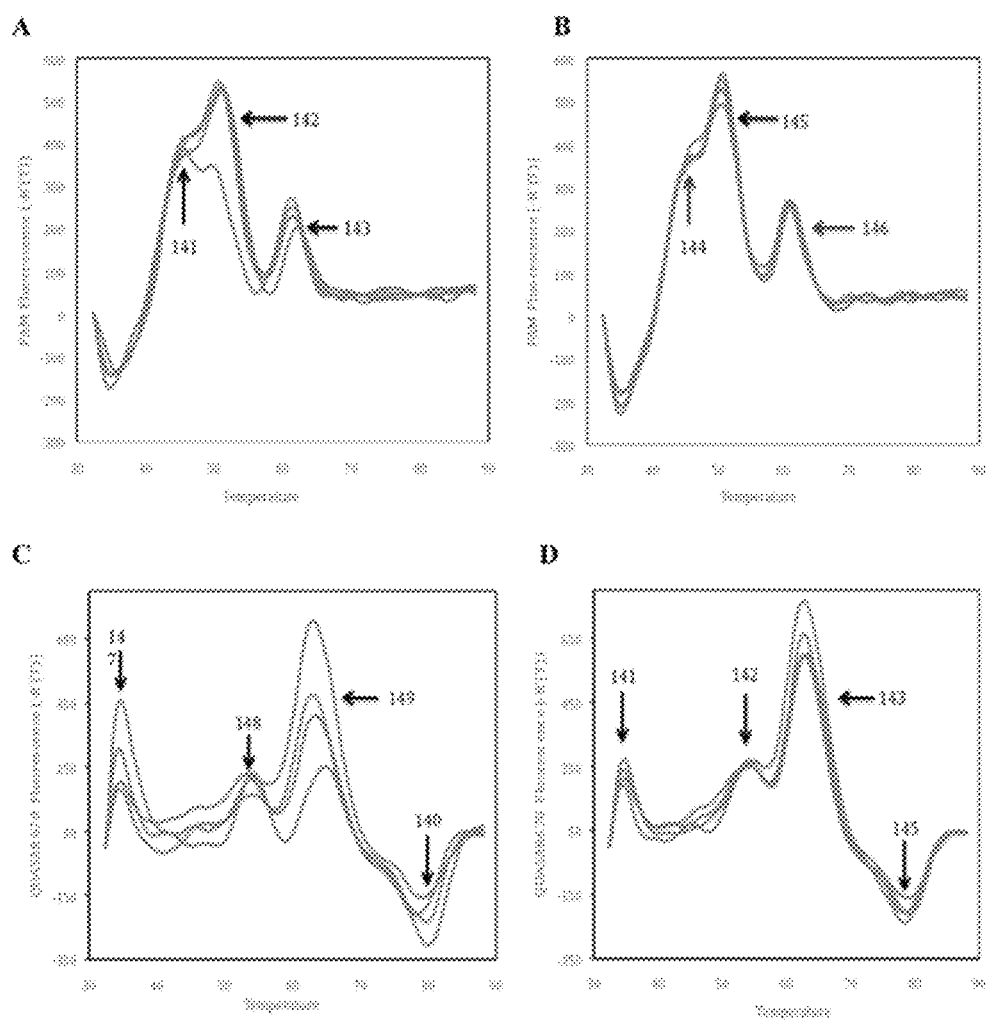
FIG. 54 shows a seven-plex for STIs as measured with FAM dual labeled linear probes (FIG. 54 panels A and B) and Quasar Fluor 670 dual labeled linear probes (FIG. 54 panels C and D). The multiplex was amplified in the presence of only 600 nM of an exemplary single-stranded mispriming prevention reagent (FIG. 54 panels A and C) or in the presence of both 600 nM of an exemplary single-stranded mispriming prevention reagent and 100 nM of an exemplary multi-stranded mispriming prevention reagent (FIG. 54 panels B and D).

This result is confirmed in FIG. 54, which shows the results of a seven-plex amplification for STIs as detected by FAM labeled probes (FIG. 54 panels A and B) and Quasar Fluor 670 labelled probes (FIG. 54 panels C and D). The multiplex was amplified in the presence of only 600 nM single-stranded mispriming prevention reagent (FIG. 54 panels A and C) and in the presence of both 600 nM single-stranded mispriming prevention reagent and 100 nM multi-stranded mispriming prevention reagent (FIG. 54 panels B and D).

Example 20

Figure 55:
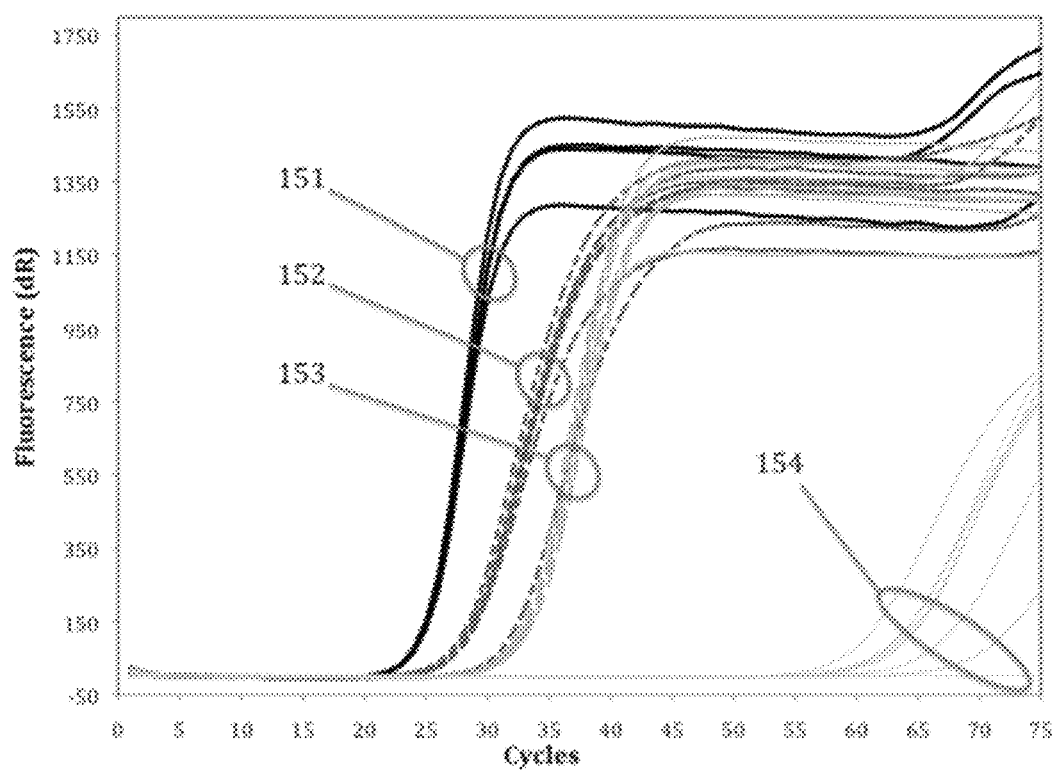
FIG. 55 shows amplification curves for the polymerase fidelity assay. Solid black lines (151) indicate the control samples using human DNA that has no mutations in the Kras gene. Dark grey dotted lines (152) indicate samples containing 100 nM of an exemplary multi-stranded mispriming prevention reagent and 1000 nM of an exemplary single-stranded mispriming prevention reagent. Light grey dotted lines (153) indicate samples containing only the blocker. The solid light grey lines (154) indicate samples containing the blocker, an exemplary multi-stranded mispriming prevention reagent (100 nM), and of an exemplary single-stranded mispriming prevention reagent (1000 nM).

Effect of Exemplary Multi-Stranded Mispriming Prevention Reagents on Polymerase Fidelity Taq polymerase is known to exhibit relatively low fidelity in that it introduces sequence changes approximately once every 10,000 incorporated nucleotides. The effect of an exemplary multi-stranded mispriming prevention reagent on polymerase fidelity was tested (FIG. 55). In this assay, a blocker (present during all thermal cycles) has been designed to prevent amplification of a product from the wild-type human Kras gene unless the polymerase introduces a sequence error in the region to which the blocker is supposed to bind, thereby preventing the blocker binding. Solid black lines (151) indicate the control samples. Dark grey dotted lines (152) indicate samples containing 100 nM multi-stranded mispriming prevention reagent and 1000 nM single-stranded mispriming prevention reagent. Light grey dotted lines (153) indicate samples containing only the blocker. The solid light grey lines (154) indicate samples containing the blocker, multi-stranded mispriming prevention reagent (100 nM), and single-stranded mispriming prevention reagent (1000 nM). As seen in FIG. 55, adding the blocker delays normal amplification by about 6 Cts (151 to 153). Adding multi-stranded mispriming prevention reagent and single-stranded mispriming prevention reagent in addition to the blocker delays amplification by about 31 Cts (two samples did not amplify at all), suggesting that single-stranded mispriming prevention reagent and multi-stranded mispriming prevention reagent are greatly increasing the fidelity of Platinum Taq.

Incorporation by Reference

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A mispriming prevention reagent comprising a nucleic acid molecule comprising, in 5' to 3' order:
   (i) a first condition-dependent stem region comprising a 5' terminal covalently linked moiety and a first stem nucleic acid sequence, wherein the first stem nucleic acid sequence is at least 6 nucleotides in length and wherein the 5' terminal covalently linked moiety comprises a cyclic or polycyclic planar moiety that does not have a bulky portion;
   (ii) a condition-dependent loop region comprising a loop nucleic acid sequence of at least 3 nucleotides in length; and
   (iii) a second condition-dependent stem region comprising a second stem nucleic acid sequence and a 3' terminal covalently linked moiety, wherein the second stem nucleic acid sequence is at least 6 nucleotides in length and is complementary to the first stem nucleic acid sequence and wherein the 3' terminal covalently linked moiety comprises a cyclic or polycyclic planar moiety that does not have a bulky portion, wherein the 3' terminal covalently linked moiety is non-identical to the 5' terminal covalently linked moiety, and wherein the 3' terminus of the second stem region is non-extendable by a DNA polymerase,
   wherein the first condition-dependent stem region hybridizes to the second condition-dependent stem region in a temperature dependent manner to acquire a stem-loop hairpin conformation, wherein the mispriming prevention reagent acquires a principally stem-loop conformation at temperatures below primer annealing temperature of an amplification reaction.

2. The mispriming prevention reagent of claim 1, wherein the loop nucleic acid sequence is a single nucleotide repeat sequence.

3. The mispriming prevention reagent of claim 2, wherein the single nucleotide repeat sequence is a poly-cytosine sequence.

4. The mispriming prevention reagent of claim 1 wherein the loop nucleic acid sequence is between 25 and 40 nucleotides in length.

5. The mispriming prevention reagent of claim 4, wherein the loop nucleic acid sequence is 28 nucleotides in length.

6. The mispriming prevention reagent of claim 1, wherein the first condition-dependent stem region hybridizes to the second condition-dependent stem region with a melting temperature of between 40° C. and 71° C.

7. The mispriming prevention reagent of claim 6, wherein the first condition-dependent stem region hybridizes to the second condition-dependent stem region with a melting temperature of between 40° C. and 55° C.

8. The mispriming prevention reagent of claim 1, wherein the first stem nucleic acid sequence and the second stem nucleic acid sequence are no more than 14 nucleotides in length.

9. The mispriming prevention reagent of claim 1, wherein the first stem nucleic acid sequence and the second stem nucleic acid sequence are each at least 8 nucleotides in length.

10. The mispriming prevention reagent of claim 9, wherein the first stem nucleic acid sequence and the second stem nucleic acid sequence are each 11 nucleotides in length.

11. The mispriming prevention reagent of claim 1, wherein the stem-loop hairpin conformation comprises a 5' or 3' overhang.

12. The mispriming prevention reagent of claim 1, wherein the stem-loop hairpin conformation comprises a blunt end.

13. The mispriming prevention reagent of claim 1, wherein:
   (a) the most 3' nucleic acid of the first stem nucleic acid sequence is cytosine and the most 5' nucleic acid of the second stem nucleic acid sequence is guanine; or
   (b) the most 3' nucleic acid of the first stem nucleic acid sequence is guanine and the most 5' nucleic acid of the second stem nucleic acid sequence is a cytosine.

14. The mispriming prevention reagent of claim 1, wherein:
   (a) the most 5' nucleic acid of the first stem nucleic acid sequence is cytosine and the most 3' nucleic acid of the second stem nucleic acid sequence is guanine; or
   (b) the most 5' nucleic acid of the first stem nucleic acid sequence is guanine and the most 3' nucleic acid of the second stem nucleic acid sequence is a cytosine.

15. The mispriming prevention reagent of claim 1, wherein the 5' terminal covalently linked moiety comprises a dabcyl moiety.

16. The mispriming prevention reagent of claim 1, wherein the 3' terminal covalently linked moiety comprises a coumarin moiety.

17. The mispriming prevention reagent of claim 16, wherein the coumarin moiety is selected from the group consisting of Coumarin 39, Coumarin 47 and Biosearch Blue.

18. The mispriming prevention reagent of claim 17, wherein the coumarin moiety is Biosearch Blue.

19. The mispriming prevention reagent of claim 1, wherein the 3' terminal covalently linked moiety comprises a dabcyl moiety.

20. The mispriming prevention reagent of claim 1, wherein the 5' terminal covalently linked moiety comprises a coumarin moiety.

21. The mispriming prevention reagent of claim 20, wherein the coumarin moiety is selected from the group consisting of Coumarin 39, Coumarin 47 and Biosearch Blue.

22. A reaction mixture comprising:
(a) a first nucleic acid primer that hybridizes to a 3' region of a target nucleic acid sequence with a first primer melting temperature;
(b) a second nucleic acid primer that hybridizes to a 3' region of the complement of the target nucleic acid sequence with a second primer melting temperature; and
(c) a mispriming prevention reagent, wherein the mispriming prevention reagent comprises a nucleic acid molecule comprising, in 5' to 3' order:
(i) a first condition-dependent stem region comprising a 5' terminal covalently linked moiety and a first stem nucleic acid sequence, wherein the first stem nucleic acid sequence is at least 6 nucleotides in length and wherein the 5' terminal covalently linked moiety comprises a cyclic or polycyclic planar moiety that does not have a bulky portion;
(ii) a condition-dependent loop region comprising a loop nucleic acid sequence of at least 3 nucleotides in length; and
(iii) a second condition-dependent stem region comprising a second stem nucleic acid sequence and a 3' terminal covalently linked moiety, wherein the second stem nucleic acid sequence is at least 6 nucleotides in length and is complementary to the first stem nucleic acid sequence, wherein the 3' terminal covalently linked moiety comprises a cyclic or polycyclic planar moiety that does not have a bulky portion, wherein the 3' terminal covalently linked moiety is non-identical to the 5' terminal covalently linked moiety, and wherein the 3' terminus of the second condition-dependent stem region is non-extendable by a DNA polymerase, wherein the second stem region hybridizes to the first condition-dependent stem region with a stem melting temperature that is no greater than both the first primer melting temperature and the second primer melting temperature, and wherein hybridization of the first condition-dependent stem region to the second condition-dependent stem region causes the reagent to acquire a stem-loop hairpin conformation, wherein the mispriming prevention reagent acquires a principally stem-loop conformation at temperatures below primer annealing temperature(s) of an amplification reaction.

23. A kit comprising a mispriming prevention reagent of claim 1.

24. A method of creating an amplification product comprising a target nucleic acid sequence or complement thereof, the method comprising:
(a) forming a reaction mixture comprising:
(i) a target nucleic acid molecule comprising the target nucleic acid sequence;
(ii) a first nucleic acid primer that hybridizes to a 3' region of the target nucleic acid sequence with a first primer melting temperature;
(iii) a second nucleic acid primer that hybridizes to a 3' region of the complement of the target nucleic acid sequence with a second primer melting temperature;
(iv) a thermostable DNA polymerase;
(v) dNTPs; and
(vi) a mispriming prevention reagent comprising a nucleic acid molecule comprising, in 5' to 3' order:
(1) a first condition-dependent stem region comprising a 5' terminal covalently linked moiety and a first stem nucleic acid sequence, wherein the first stem nucleic acid sequence is at least 6 nucleotides in length and wherein the 5' terminal covalently linked moiety comprises a cyclic or polycyclic planar moiety that does not have a bulky portion;
(2) a condition-dependent loop region comprising a loop nucleic acid sequence of at least 3 nucleotides in length; and
(3) a second condition-dependent stem region comprising a second stem nucleic acid sequence and a 3' terminal covalently linked moiety, wherein the second stem nucleic acid sequence is at least 6 nucleotides in length and is complementary to the first stem nucleic acid sequence, wherein the 3' terminal covalently linked moiety comprises a cyclic or polycyclic planar moiety that does not have a bulky portion, wherein the 3' terminal covalently linked moiety is non-identical to the 5' terminal covalently linked moiety, wherein the 3' terminus of the second condition-dependent stem region is non-extendable by the thermostable DNA polymerase, wherein the second condition-dependent stem region hybridizes to the first condition-dependent stem region with a stem melting temperature that is no greater than the first primer melting temperature and the second primer melting temperature, and wherein hybridization of the second condition-dependent stem region to the first condition-dependent stem region causes the reagent to acquire a stem-loop hairpin conformation,
wherein the mispriming prevention reagent acquires a principally stem-loop conformation at temperatures below primer annealing temperature(s) of an amplification reaction; and
(b) incubating the reaction mixture under conditions such that the first primer or second primer is extended by the thermostable DNA polymerase to create an amplification product comprising the target nucleic acid sequence or complement thereof.

* * * * *

SEQUENCE LISTING

```
<160> NUMBER OF SEQ ID NOS: 49

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctccagccag gcacgctcac gtgacagacc g                                          31

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acgtggaggc gatcacaccg cagacgtt                                              28
```

```
<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-BHQ2 modified
<220> FEATURE:
<223> OTHER INFORMATION: 3'-C3 spacer modified

<400> SEQUENCE: 3
ctggttggtg cagaag                                                   16

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-Quasar 670 modified
<220> FEATURE:
<223> OTHER INFORMATION: 3'-BHQ2 modified

<400> SEQUENCE: 4
tcaggtccat gaattggctc aga                                           23

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-BHQ2 modified
<220> FEATURE:
<223> OTHER INFORMATION: 3'-C3 spacer modified

<400> SEQUENCE: 5
cagcgggttg tt                                                       12

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-BHQ2 modified
<220> FEATURE:
<223> OTHER INFORMATION: 3'-Quasar 670 modified

<400> SEQUENCE: 6
atgcgcttgt tggtcaaccc cgat                                          24

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-Quasar 670 modified
<220> FEATURE:
<223> OTHER INFORMATION: 3'-BHQ2 modified
```

```
<400> SEQUENCE: 7
aagccccagc gccgacagtc gtt                                              23

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 3'-BHQ2 modified

<400> SEQUENCE: 8
acagaccgcc gg                                                          12

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agcgcccact cgtagccgta caggatctcg aggaaac                               37

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcttgggctg gaagagctcg tatggcac                                         28

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-QSR670 modified
<220> FEATURE:
<223> OTHER INFORMATION: 3'-BHQ2 modified

<400> SEQUENCE: 11
actcgcgtcc ttacccaaaa aaaaaaaaaa                                       30

<210> SEQ ID NO 12
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 3'-BHQ2 modified

<400> SEQUENCE: 12
atgtcggtgg tga                                                         13
```

```
<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ttccggtaac caggactgaa cgggatacga atgggggttt gg                          42

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tcgcagccac gttacgctcg tggacatac                                         29

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-BHQ2 modified
<220> FEATURE:
<223> OTHER INFORMATION: 3'-QSR670 modified

<400> SEQUENCE: 15
aaaaaaaaaa aaaaaggcag tcatcccgtt                                        30

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-BHQ2 modified
<220> FEATURE:
<223> OTHER INFORMATION: 3'-C3 spacer modified

<400> SEQUENCE: 16
ttacagccta tcgcctcgc                                                    19

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ttcggcgcac aaagtgtctc tggctgttgt                                        30

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 18
ttggcacgat gctcccacat tgcgacttc                                29

<210> SEQ ID NO 19
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
ggcacgatgc tcccacattg cgacttctgc ccttgatagt tatattgaaa gtaaatagta      60
gatagtagat gatgatataa acaacagcca gagacacttt gtgcgccgaa               110

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-QSR670A modified
<220> FEATURE:
<223> OTHER INFORMATION: 3'-BHQ2 modified

<400> SEQUENCE: 20
ttctattatt tattttcat                                                  19

<210> SEQ ID NO 21
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 3'-BHQ2 modified

<400> SEQUENCE: 21
atcattattt acta                                                       14

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-QSR670 modified
<220> FEATURE:
<223> OTHER INFORMATION: 3'-C3 spacer modified

<400> SEQUENCE: 22
cagctgcact gggaagggtg cagtctgacc                                      30

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: 3'-BHQ2 modified

<400> SEQUENCE: 23
ggtcagactg cacccttccc agtgcagctg                                    30

<210> SEQ ID NO 24
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Dabcyl modified
<220> FEATURE:
<223> OTHER INFORMATION: 3'-Dabcyl modified

<400> SEQUENCE: 24
gaataatata gcccccccccc cccccccccc ccctatatt attc                    44

<210> SEQ ID NO 25
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-BHQ2 modified
<220> FEATURE:
<223> OTHER INFORMATION: 3'-Biosearch Blue modified

<400> SEQUENCE: 25
gaataatata gcccccccccc cccccccccc cccccccccc tatattattc             50

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aaggtctttc gcaacccaac gcta                                          24

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gactgggtcc tttcttgga                                                19

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-Cal Red 610 modified
<220> FEATURE:
<223> OTHER INFORMATION: 3'-BHQ2 modified -continued

```
<400> SEQUENCE: 28
tcggctagta gtcttgtgg                                                  19

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ctttcgcaac ccaacgcta                                                  19

<210> SEQ ID NO 30
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
gaauaauaua gccccccccc cccccccccc cccccccccc uauauuauuc                50

<210> SEQ ID NO 31
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 31
gaauaauaua gccccccccc cccccccccc cccccccccc uauauuauuc                50

<210> SEQ ID NO 32
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(11)
<223> OTHER INFORMATION: 2'-O-methyl RNA nucleotide
<220> FEATURE:
<221> NAME/KEY: modified_base
<222> LOCATION: (40)..(50)
<223> OTHER INFORMATION: 2'-O-methyl RNA nucleotide

<400> SEQUENCE: 32
gaauaauaua gccccccccc cccccccccc cccccccccc uauauuauuc                50

<210> SEQ ID NO 33
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide
<220> FEATURE:
<221> NAME/KEY: modified_base
<222> LOCATION: (1)..(10)
<223> OTHER INFORMATION: 2'-O-methyl RNA nucleotide
<220> FEATURE:
<221> NAME/KEY: modified_base
<222> LOCATION: (45)..(54)
<223> OTHER INFORMATION: 2'-O-methyl RNA nucleotide

<400> SEQUENCE: 33
uaauaauaua cccccccccc cccccccccc cccccccccc cccuauauu auua          54

<210> SEQ ID NO 34
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(10)
<223> OTHER INFORMATION: 2'-O-methyl RNA nucleotide
<220> FEATURE:
<221> NAME/KEY: modified_base
<222> LOCATION: (45)..(54)
<223> OTHER INFORMATION: 2'-O-methyl RNA nucleotide

<400> SEQUENCE: 34
uaauagugua cccccccccc cccccccccc cccccccccc cccuguauu auua          54

<210> SEQ ID NO 35
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(10)
<223> OTHER INFORMATION: 2'-O-methyl RNA nucleotide

<400> SEQUENCE: 35
uaauaauaua cccccccccc cccccccccc cccccccccc cccctatatt atta          54

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ccttctctct gccccctggt                                                20

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 37
ctgtttgaga gttaaatgat gtc                                              23

<210> SEQ ID NO 38
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gggcacccta ctatgtg                                                     17

<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cactccctga aagagga                                                     17

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ggattatgcc tggcaccat                                                   19

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
aggggttcca ctacgtaga                                                   19

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
acacctcagc atataacaa                                                   19

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gccgcattgt ataagtaga                                                    19

<210> SEQ ID NO 44
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cccaagctcc ttcttct                                                      17

<210> SEQ ID NO 45
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Dabcyl modified
<220> FEATURE:
<223> OTHER INFORMATION: 3'-Coumarin modified

<400> SEQUENCE: 45
gaataatata gccccccccc cccccccccc ccctatatt attc                          44

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3'-Coumarin modified

<400> SEQUENCE: 46
gagcagactc gcactgaggt a                                                 21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-BHQ2 modified
<220> FEATURE:
<223> OTHER INFORMATION: 3'-Coumarin modified

<400> SEQUENCE: 47
tacctcagtg cgagtctgct c                                                 21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-carbon spacer modified
<220> FEATURE:
<223> OTHER INFORMATION: 3'-Biosearch Blue modified

```
<400> SEQUENCE: 48
gagcagactc gcactgaggt a                                              21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-BHQ2 modified
<220> FEATURE:
<223> OTHER INFORMATION: 3'-Biosearch Blue modified

<400> SEQUENCE: 49
tacctcagtg cgagtctgct c                                              21
```